US008012958B2

(12) United States Patent
Sabnani et al.

(10) Patent No.: US 8,012,958 B2
(45) Date of Patent: Sep. 6, 2011

(54) METHODS FOR TREATING ANXIETY RELATED DISORDERS

(75) Inventors: Sanjay Sabnani, Northridge, CA (US); Donald Wesson, Oakland, CA (US)

(73) Assignee: Hythlam, Inc., Los Angeles, CA (US)

( * ) Notice: Subject to any disclaimer, the term of this patent is extended or adjusted under 35 U.S.C. 154(b) by 698 days.

(21) Appl. No.: 11/910,967

(22) PCT Filed: Apr. 7, 2006

(86) PCT No.: PCT/US2006/013152
§ 371 (c)(1),
(2), (4) Date: Apr. 22, 2008

(87) PCT Pub. No.: WO2006/110580
PCT Pub. Date: Oct. 19, 2006

(65) Prior Publication Data
US 2008/0280885 A1 Nov. 13, 2008

Related U.S. Application Data

(60) Provisional application No. 60/728,979, filed on Oct. 21, 2005, provisional application No. 60/729,013, filed on Oct. 21, 2005, provisional application No. 60/669,033, filed on Apr. 7, 2005.

(51) Int. Cl.
*A01N 43/62* (2006.01)
*A61K 31/55* (2006.01)
(52) U.S. Cl. .................................. 514/218; 514/220
(58) Field of Classification Search ................ 514/218
See application file for complete search history.

(56) References Cited

U.S. PATENT DOCUMENTS

| | | | |
|---|---|---|---|
| 4,595,684 | A | 6/1986 | Bennett et al. |
| 5,512,590 | A | 4/1996 | George et al. |
| 2001/0020002 | A1 | 9/2001 | Lederman et al. |
| 2004/0235844 | A1 | 11/2004 | Goodacre |
| 2005/0176680 | A1* | 8/2005 | Lalji et al. ............... 514/58 |
| 2008/0207601 | A1 | 8/2008 | Sabnani |
| 2008/0255097 | A1 | 10/2008 | Sabnani et al. |

FOREIGN PATENT DOCUMENTS

| | | |
|---|---|---|
| EP | 1374952 B1 | 9/2006 |
| EP | 1378267 B1 | 6/2007 |
| WO | WO-9961014 | 12/1999 |

OTHER PUBLICATIONS

Arborelius et al. (The role of corticotropin-releasing factor in depression and anxiety disorders; Journal of Endocrinology (1999) 160, 1-12).*
Briley et al. (Milestone in Drug Therapy Anxiolytics (2000)).*
Shannon et al.( Safety and efficacy of flumazenil in the reversal of benzodiazepine induced conscious sedation;The Journal of Pediatrics vol. 131, Issue 4, Oct. 1997, pp. 582-586.*
EP06740761 Supplementary Search Report dated Oct. 6, 2009.
File, et al., "Effects of Nitrendipine Chlordiazepoxide, Flumazenil and Baclofen on the Increased Anxiety Resulting from Alcohol Withdrawal," Prog. Neuro-Psychopharmacol. & Biol-Psychiat., 1992, vol. 16, pp. 87-93.
Gulinello et al., "Progesterone Withdrawal Increases the Alpha4 Subunit of the GABAA Receptor in Male Rats in Association with Anxiety and Altered Pharmacology: A Comparison with Female Rats," Neuropharmacology, Sep. 2002, vol. 43, pp. 701-714.
Gulinello et al., "Progesterone Withdrawal Increases the Anxiolytic Actions of Gaboxadol: Role of Alpha4betadelta GABAA Receptors," Developmental Neuroscience, NeuroReport, vol. 14, No. 1, Jan. 20, 2003, pp. 43-46.
Khemraj, et al, "Potential Role of Neurosteroid Allopregnenolone in Anxiolytic Action of Ethanol and Withdrawal-Induced Anxiety," Abstract from Indian Journal of Pharmacology, 2003, vol. 35, p. 129.
PCT/US06/13152 International Preliminary Report on Patentability dated Oct. 18, 2007.
PCT/US06/13152 International Search Report and Written Opinion dated Apr. 27, 2007.
Smith et al., "Effects of a Low Dose of Ethanol in an Animal Model of Premenstrual Anxiety," Alcohol, 2004, vol. 33, pp. 41-49.
Belzung, et al., "Flumazenil Induces Benzodiazepine Partial Agonist-Like Effects in BALB/c but not C57BL/6 Mice", Psychopharmacology, Jan. 31, 2002, vol. 148, No. 1, pp. 23-32.
Office Action, Chinese Patent Application No. 200680020240.1, Mar. 11, 2010.
Britan, et al., Anxiolytic Effect of Progesterone is Medicated by the Neurosteroid Allopregnanolone at Brain GABAA Receptors, J. Neuroendocrinol., Mar. 1995, vol. 7, No. 3, pp. 171-177.
Office Action, Russian Patent Application No. 2007141204/15, Nov. 9, 2009.
Oliver, "Animal Models in Obsessive Compulsive Disorder", International Clinical Psychopharmacology, Clinical Neuroscience Publishers, London, GB, vol. 7, No. Suppl. 1, pp. 27-29, Jun. 1, 1992.
Office Action, European Patent Application No. 06740761.9 , Feb. 10, 2010.
"Flumazenil Antidotes", Drug Facts 1997 , 3373-3379.
Altemus, Margaret et al., "Changes in Cerebrospinal Fluid Neurochemistry During Treatment of Obsessive-compulsive Disorder with Clomipramine", Arch Gen Psychiatry 1994, 51:794-803.
Altemus, M.D., Margaret et al., "Abnormalities in the Regulation of Vasopressin and Corticotropin Releasing Factor Secretion in Obsessive-Compulsive Disorder", Arch Gen Psychiatry 1992, vol. 49: 9-20.
Argyropoulos, Spilios V. et al., "Peptide receptors as targets for anxiolytic drugs", Anxiolytics 2000, 151-175.

(Continued)

*Primary Examiner* — Sreeni Padmanabhan
*Assistant Examiner* — Layla Soroush
(74) *Attorney, Agent, or Firm* — Genga & Associates P.C.; Don C. Moody, Esq.

(57) ABSTRACT

The present invention relates to methods of and compositions for treating and relieving symptoms and disease associated with indications caused by a physiological drive to alleviate a sensation of anxiety. In one treatment method, methods of, and compositions for, modulating the expression of certain GABAA receptor subunits are used to treat anxiety-related disorders and depressive disorders associated with physiological tolerance to endogenous neurosteroids.

5 Claims, 6 Drawing Sheets

OTHER PUBLICATIONS

Ibanez, Juan Jose L. "U.S. Patent Office Action", Office Action in U.S. Appl. No. 11/615,460 May 13, 2010.
Kapczinski, F. et al., "Flumazenil has an anxiolytic effect in simulated stress", Psychopharmacology 1994, 114(1):187-9.
Kunovac, J.L. et al., "Future directions in anxiolytic pharmacotherapy", Psychiatr Clin North Am 1995, 18(4):895-909.
Strohle, Andreas et al., "Flumazenil attenuates the pituitary response to CRH in healthy males", European Neuropsychopharmacology 1996, 6: 323-325.
Examiner's Report, Australian Patent Application No. 2006235257, mailed Sep. 14, 2009.
Examiner's Report, Australian Patent Application No. 2006235257, mailed Jan. 19, 2010.
"American Psychiatric Association Work Group on Eating Disorders. Practice Guideline for the Treatment of Patients with Eating Disorders (Revision)", Am J Psychiatry, 2000, (1 Suppl):1-39.
"National Collaborating Centre for Mental Health. Eating Disorders. Core Interventions in the Treatment and Management of Anorexia Nervosa, Bulimia Nervosa and Related Eating Disorders", Leicester (UK): British Pyschological Society 2004, 260.
"Practice Guideline for the Treatment of Patients with Acute Stress Disorder and Posttraumatic Stress Disorder.", American Psychiatric Association Arlington (VA) 2004, 57.
Astolfi, Helen et al., "Cannabis Dependence and Treatment", GP Drug and Alcohol Supplement No. 10, Central Coast Area Health Service Publication 1998.
Banerjee, et al., "Alterations in GABA-A Receptor $\alpha 1$ and $\alpha 4$ Subunit mRNA Levels in Thalamic Relay Nuclei Following Absence-Like Seizures in Rats", Experimental Neurology 154 1998, 213-223.
Barbaccia, et al., "Stress and Neurosteroids in Adult and Aged Rats", Experimental Gerontology, vol. 33 Nos. 7/8 1998, 697-712.
Barbaccia, et al., "The Effects of Inhibitors of GABAergic Transmission and Stress on Brain and Plasma Allopregnanolone Concentrations", British Journal of Pharmacology 1997, 120, 1582-1588.
Bernadi, F. et al., "Disadaptive Disorders in Women: Allopregnanolone, A Sensitive Steroid", Gynecological Endocrinology, vol. 19 No. 6 2004, 344-353(10).
Bhatia, et al., "Diagnosis and Treatment of Premenstrual Dysphoric Disorder", American Family Physician, vol. 66, No. 7 2002.
Biggio, et al., "GABA-A Receptor Plasticity During Long-Term Exposure to and Withdrawal from Progesterone", Int. Rev. Neurobiol 2001, 46:207-41.
Buckley et al., "GABA (A) Receptor $\beta$ Subunit mRNA Expression in the Human Alcoholic Brain", Neurochemistry International, vol. 45 2004, 1011-1020.
Burt, D.R. "Alpha Subunit Position and GABA Receptor Function", Science's STKE, No. 270, PE5 2005, pp. 1-2.
Casasola, et al., "Hyperexcitability Induced by GABA Withdrawal Facilitates Hippocampal Long-Term Potentiation", Neuroscience, vol. 126 2004, 163-171.
Clark, Mike "Sensitivity of the Rat Hippocampal GABA-A Receptor $\alpha 4$ Subunit to Electroshock Seizures", Neuroscience Letters 250 1998, 17-20.
Concas, et al., "Caffeine-Induced Increases in the Brain and Plasma Concentrations of Neuroacitve Steroids in the Rat", Pharmacol. Biochem Behav vol. 66(1) 2000, 39-45.
Concas, et al., "Nicotine-Induced Changes in Cerebrocortical Neuroactive Steroids and Plasma Corticosterone Concentration in the Rat", Pharmacology Biochemistry, and Behavior, vol. 74 2003, 683-690.
Concas, et al., "Physiological Modulation of GABA-A Receptor Plasticity by Progesterone Metabolites", European Journal of Pharmacology 1999, 225-235.
Criswell, Hugh E. et al., "A Conceptualization of Integrated Actions of Ethanol Contributing to its GABAmimetic Profile: A Commentary", Neuropsychopharmacology vol. 30 2005, 1407-1425.
Damianisch, Katrin "The Influence of Subchronic Administration of the Neurosteroid Allopregnanolone on Sleep in the Rat", Neuropsychopharmacology vol. 25 No. 4 2001, 576-584.
Follesa, et al., "Allopregnanolone Synthesis in Cerebellar Granule Cells: Roles in Regulation of GABA-A Receptor Expression and Function During Progesterone Treatment and Withdrawal", Molecular Pharmacology 2000, vol. 57, 1262-1270.
Follesa, et al., "Changes in GABA-A Receptor Gene Expression Induced by Withdrawal of, but not by Long-Term Exposure to Zaleplon or Zolpidem", Neuropharmacology 42 2002, 191-198.
Follesa, et al., "Increase in expression of the GABA-A Receptor Alpha-4 Subunit Gene Induced by Withdrawal of, but not by Long-Term Treatment with, Benzodiazepine Full or Partial Agonists", Molecular Brain Research vol. 92 2001, 138-148.
Follesa, et al., "Modulation of GABA-A Receptor Gene Expression by Allopregnanolone and Ethanol", European Journal of Pharmacology 500 2004, 413-425.
Follesa, et al., "Gamma-Hydroxybutric Acid and Diazepam Antagonize a Rapid Increase in GABA-A Receptors a4 Subunit mRNA Abundance Induced by Ethanol Withdrawal in Cerebellar Granule Cells", Mol Pharmacol 2003, 63:96-907.
Ford, Matthew et al., "Treatment with and Withdrawal from Finasteride Alter Ethanol Intake Patterns in Male C57BL/6J mice: Potential Role of Endogenous Neurosteroids", Alcohol vol. 37 2005, 23-33.
Frostholm, et al., "Harmaline-Induced Changes in Gamma Amino Butyric-Acid-A Receptor Subunit mRNA Expression in Murine Olivocerebellar Nuclei", Molecular Brain Research 85 2000, 200-208.
Frye, Gerald et al., "Binge Ethanol Exposure Delays Development of GABAergic Miniature Postsynaptic Currents in Septal Neurons", Developmental Brain Research, vol. 152 2004, 199-212.
Girdler, Susan "Allopregnanolone Levels and Reactivity to Mental Stress Premenstrual Dysphoric Disorder", Biological Psychiatry, vol. 49, Issue 9 2001, 788-797.
Gulinello, et al., "Progesterone Withdrawal Increases the a4 Subunit of the GABA Receptor in Male Rats in Association with Anxiety and Altered Pharmacology—A Comparison With Female Rats", Neuroparmacology. vol. 43, (4) 2002, 701-714 (Abstract Only).
Idrissi, A. et al., "Decreased GABA-A Receptor Expression in the Seizure-Prone Fragile X Mouse", Neuroscience Letters 377 2005, 141-146.
Jain, et al., "Reversal of Caffeine-Induced Anxiety by Neurosteroid 3-Alpha-Hydroxy-5-Alpha-Pregnane-20-One in Rats", Neuropharmacology vol. 48 2005, 627-638.
Johnston, Graham, "GABA-A Receptor Pharmacology." Current Pharmaceutical Design, 2005,11, 1867-1885.
Johnston, et al., "Flavonoids: Some of the Wisdom of Sage?", British Journal of Pharmacology, vol. 142 2004, 809-810.
Khemraj, H. et al., "Anticonvulsant Activity of Fluoxetine: Involvement of GABAergic Neuroactive Steroid Allopregnenolone", Abstract From XXXV Annual Conference of the Indian Pharmacological Society, Gwalior, Nov. 2002.
Khemraj, H. et al., "Potential Role of Neurosteroid Allopregnenolone in Anxiolytic Action of Ethanol and Withdrawal-Induced Anxiety", Abstract from XXXV Annual conference of the Indian Pharmacological Society, Gwalior, Nov. 2002.
Knapp, D.J. et al., "SB242084, Flumazenil and CRA1000 Block Ethanol Withdrawal-Induced Anxiety in Rats", Alcohol, vol. 32 2004, pp. 101-111.
Kokate, Tushar G. et al., "Finasteride, $5\alpha$-Reductase Inhibitor, blocks the Anticonvulsant Activity of Progesterone in Mice", Journal of Pharmacology and Experimental Therapeutics, vol. 288 1999, 679-684.
Krogsgaard-Larsen, et al., "GABA-A Agonists and Partial Agonists: THIP (Gaboxadol) as a Non-Opioid Analgesic and a Novel Type of Hypnotic", Biochemical Pharmacology, vol. 68 2004, 1573-1580.
Le Melledo, Jean-Michael et al., "Role of Progesterone and Other Neuroactive Steroids in Anxiety Disorders", Expert Review of Neurotherapeutics, vol. 4 No. 5 Sep. 2004, 851-860.
Lovick, et al., "Changes in GABA-A Receptor Subunit Expression in the Midbrain During the Oestrous Cycle in Wistar Rats", Neuroscience 131 2005, 397-405.
Lujan, R. et al., "Glutamate and GABA Receptor Signaling in the Developing Brain", Neuroscience, vol. 130 2005, 567-580.

Maitra, et al., "Modulation of GABA-A Receptor Function by Neuroactive Steroids: Evidence for Heterogeneity of Steroid Sensitivity of Recombinant GABA-A Receptor Isoforms", Canadian Journal of Physiology and Pharmacology, 76(9) 1998, 909-920.

Mann, K. "Pharmacotherapy of Alcohol Dependence", CNS Drugs, vol. 18, No. 8 2004, pp. 485-504.

Mayo, et al., "Premenstrual Syndrome: A Natural Approach to Management", Applied Nutritional Science Reports, vol. 5 No. 6 1999.

McIntosh, et al., "Clinical Guidelines for the Management of Anxiety. Management of Anxiety Panic Disorder (with or without Agoraphobia) and Generalized Anxiety Disorder in Adults in Primary, Secondary and Community Care.", London (UK) National Institute for Clinical Excellence (NICE) Dec. 2004, 165.

Morrow, Leslie A. et al., "Neuroactive Steroid 3alpha-Hydroxy-5alpha-Pregnan-20-One Modulates Electrophysiological and Behavioral Actions of Ethanol", The Journal of Neuroscience vol. 20(5), 2000, 1982-1989.

Moy, et al., "Enhanced Ultrasonic Vocalization and FoS Protein Expression Following Ethanol Withdrawal: Effects of Flumazenil", Psychopharmacology, vol. 152 2000, 208-215.

Moy, et al., "Flumazenil Blockade of Anxiety Following Ethanol Withdrawal in Rats", Psychopharmacology, vol. 131 1997, 354-360.

Muller, et al., "Glycine Receptors and GABA-A Receptor α1 and Gamma 2 Subunits During the Development of Mouse Hypoglossal Nucleus", European Journal of Neuroscience, vol. 20 2004, 3286-3300.

Olsen, et al., "Alcohol Effects on Gamma-Aminobutyric Acid Type A Receptors: Are Extrasynaptic Receptors in the Answer?", Life Sciences 76 2004, 1-8.

Przewlocki, R et al., "Effects of Morphine on Gene Expression in the Rat Amygdala", Journal of Neurochemistry, vol. 91 2004, 38-48.

Purdy, Robert H. "Stress-Induced Elevations of gamma-Aminobutyric Acid Type A Receptor-Active Steroids in the Rat Brain", Proc. Natl. Acad. Sci. vol. 88 May 1991, 4553-4557.

Reddy, Doodipala "Anxiolytic Activity of Progesterone in Progesterone Receptor Knockout Mice", Neuropharmacology vol. 48 2005, 14-24.

Reddy, Doodipala S. "Stress-Induced Deoxycorticosterone Derived Neurosteroids Modulate GABA-A Receptor Function and Seizure Susceptibility", The Journal of Neuroscience vol. 22(9) May 1, 2002, 3795-3805.

Rissman, et al., "Subregional Analysis of GABA-A Receptor Subunit in mRNAs in the Hippocampus of Older Persons with and without Cognitive Impairment", Journal of Chemical Neuroanatomy 28 2004, 17-25.

Rouge-Pont, et al., "The Neurosteroid Allopregnanolone Increases Dopamine Release and Dopaminergic Response to Morphine in the Rat Nucleus Accumbens", European Journal of Neuroscience, vol. 16, 169 (Abstract Only), 2002.

Sanna, et al., "Changes in GABA-A Receptor Gene Expression Associated with Selective Alterations in Receptor Function and Pharmacology after Ethanol Withdrawal", The Journal of Neuroscience 17, (2003), 23(37)11711-11724.

Savic, I. et al., "Feasibility of Reversing Benzodiazepine Tolerance with Flumazenil", Lancet, 0099-5355, vol. 337 1991, 133-137.

Sieghart, et al., "Affinity of Various Ligands for GABA-A Receptors containing α4β3γ2α4γ2α1β3γ2 Subunits", European Journal of Pharmacology vol. 304 1996, 155-162.

Smith, et al., "GABA-A Receptor Alpha-4 Subunit Suppression Prevents Withdrawal properties of an Endogenous Steroid", Nature vol. 392 (1998), 926-930.

Smith, et al., "Hormonally Regulated α4β2δ GABA-A Receptors are a Target for Alcohol", Nature Neuroscience vol. 5, No. 8 Aug. 2002, 721-722.

Smith, S.S. et al., "Neurosteroid Administration and Withdrawal Alter GABA(A) Receptor Kinetics in CA1 Hippocampus of Female Rats", J. Physiol., vol. 564, Pt. 2 2005, pp. 421-436 (Abstract Only).

Smith, S.S. et al., "Progesterone Withdrawal Increases the α4 Subunit of the GABA-A Receptor in Male Rats in Association with Anxiety and Altered Pharmacology—A Comparison With Female Rats", Neuropharmcology, vol. 43, Issue 4 Sep. 2002, 701-714.

Smith et al., "Steroid Withdrawal in the Mouse Results in Anxiogenic Effects of 3α,5β-THP: A Possible Model of Premenstrual Dysphoric Disorder", Psychopharmacology (2006) 186:3, 323-33 (Abstract only).

Smith, et al., "Withdrawal from 3α-OH-5α-Pregnan-20-One Using a Pseudopregnancy Model Alters the Kinetics of Hippocampal GABA-Gated Current and Increases the GABA Receptor a4 Subunit in Association with Increased Anxiety", The Journal of Neuroscience 1998, 18(14):5275-5284.

Smith, et al., "Withdrawal Properties of a Neuroactive Steroid: Implications for GABA-A Receptor Gene Regulation in the Brain and Anxiety Behavior", Steroids 67 2002, 519-528.

Smith S. S., et al., "Allopregnanolone Levels and Symptom Improvements in Severe Premenstrual Syndrome", J Clin Psychopharmacol 2002, (5):516-520 (Abstract Only).

Snow, V. et al., "Pharmacologic Management of Acute Attacks of Migraine and Prevention of Migraine Headache", Ann Intern Med 2002, 137(10):840-52.

Strohle, et al., "GABA-A Receptor-Modulating Neuroactive Steroid Composition in Patients with Panic Disorder Before and During Paroxetine Treatment", Am. J. Psychiatry vol. 159 2002, 145-147.

Weiland, et al., "Estrogen and Progesterone Regulate Opiate Receptor Densities in Multiple Brain Regions", Endocrinology, vol. 126 1990, 804-808.

Williams, et al., "Effects of Repeated Inhalation of Toluene on Ionotropic GABA-A and Glutamate Receptor Subunit Levels in Rat Brain", Neurochemistry International, vol. 46 2005, 1-10.

* cited by examiner

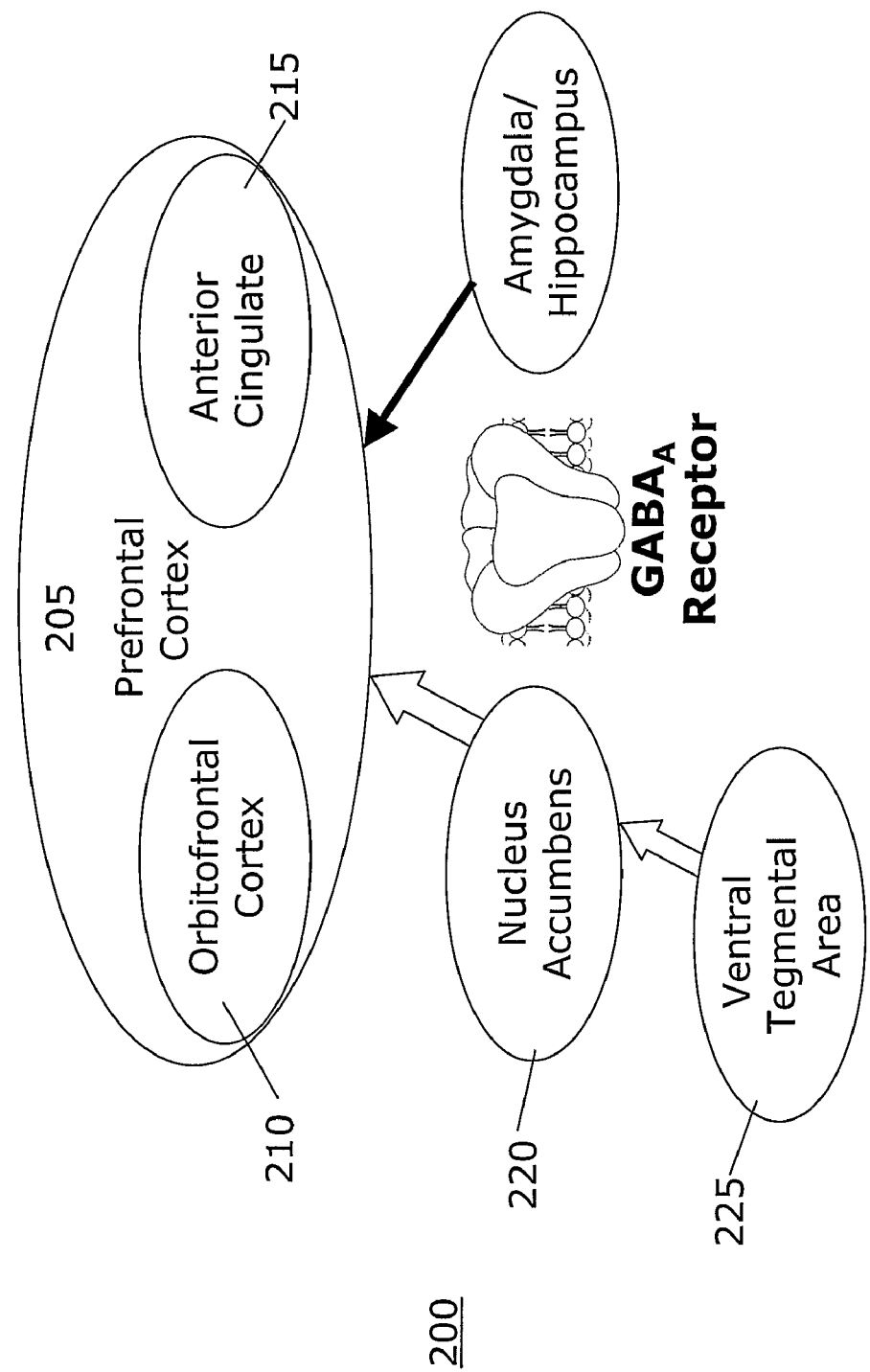

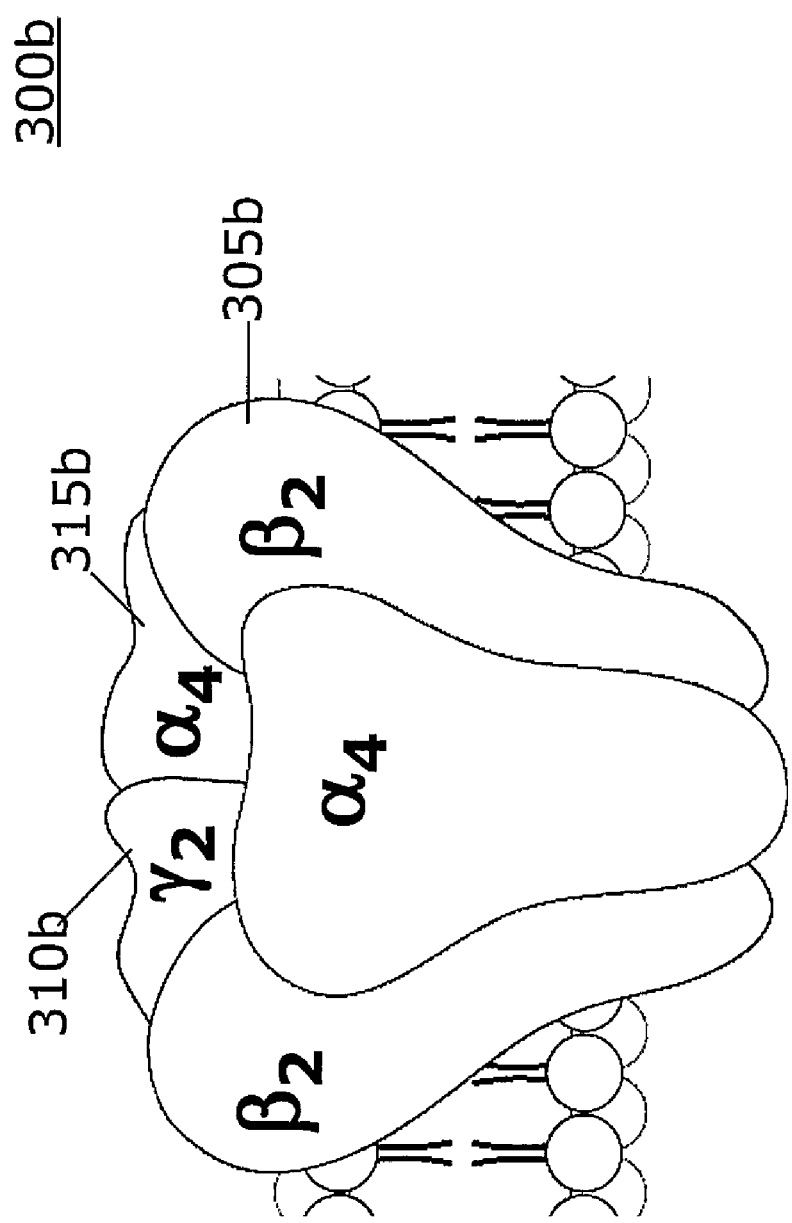

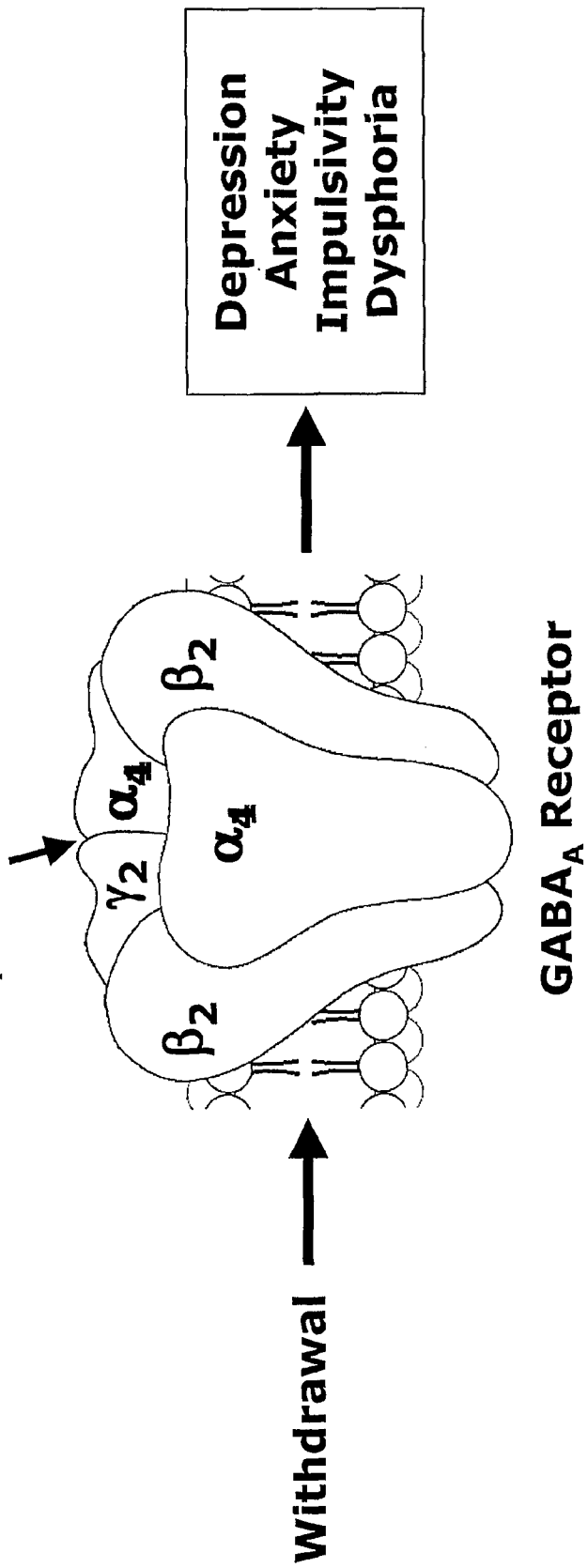

METHODS FOR TREATING ANXIETY RELATED DISORDERS

CROSS-REFERENCE TO RELATED APPLICATIONS

The present invention is the U.S. national phase application of PCT/US2006/013152 filed on Apr. 7, 2006, which claims priority to U.S. Provisional Patent Application No. 60/669,033, filed on Apr. 7, 2005, U.S. Provisional Patent Application No. 60/728,979 filed on Oct. 21, 2005, and U.S. Provisional Patent Application No. 60/729,013 filed on Oct. 21, 2005.

FIELD OF THE INVENTION

The present invention relates to methods of and compositions for treating and relieving symptoms and disease associated with indications caused by a physiological drive to alleviate a sensation of anxiety. More specifically, the present invention relates to methods of and compositions for treating and relieving symptoms associated with endogenous neurosteroid withdrawal.

The present invention is also relates to a methodology for diagnosing a person in an altered $GABA_A$ receptor state. In particular, the methodology is directed toward determining the relative receptivity of a patient to the treatment methodologies of the present invention by qualitatively or quantitatively measuring progesterone levels in a patient, or, more preferably, the allopregnanolone levels within a patient's brain.

The present invention also relates to a treatment methodology that, in a first stage, improves a patient's physiological receptivity to treatment. In particular, the methodology is directed toward preventing the up-regulation of endogenous neuroactive steroids or actively down-regulating the production of endogenous neuroactive steroids to avoid cross-tolerance. The present invention also relates to optionally employing conventional treatment programs in combination with the methods of and compositions of the present invention in a comprehensive treatment plan.

The present invention also relates to a treatment methodology that, in a second stage, employs methods of and compositions for modulating the expression of certain $GABA_A$ receptor subunits, thus treating the withdrawal symptoms, such as, but not limited to, anxiety-related disorders and depressive disorders associated with physiological tolerance to endogenous neurosteroids in a comprehensive treatment plan.

More specifically, the present invention relates to methods of, devices for, and treatment protocols for using pharmaceutical compositions from a class of compounds that directly or indirectly modulates $GABA_A$ by modulating the expression of the $GABA_A$ receptor $\alpha_4$ subunit relative to the $GABA_A$ receptor $\alpha_1$ subunit.

The present invention also relates to a class of compounds, and methods of identifying such compounds, that modulates the expression of certain $GABA_A$ receptor subunits. More specifically, the compound of choice is one that a) acts as a partial agonist of $GABA_A$; b) inhibits the upregulation of the $GABA_A$ receptor $\alpha_4$ subunit and/or increases the relative ratio of the $GABA_A$ receptor $\alpha_1$ subunit to the $GABA_A$ receptor $\alpha_4$ subunit; and c) does not cause the upregulation of the $GABA_A$ receptor $\alpha_4$ subunit and/or does not cause the decrease of the relative ratio of the $GABA_A$ receptor $\alpha_1$ subunit to the $GABA_A$ receptor $\alpha_4$ subunit once the composition is no longer present in the patient's system.

BACKGROUND OF THE INVENTION

While most anxiety disorders and depressive respond well to treatment, long-term treatment is conventionally required to prevent recurrence and maintain anxiety levels. The standard current approach to treating most anxiety disorders is a combination of cognitive-behavioral therapy (CBT) with pharmacological compounds. Typically, the compounds include selective serotonin reuptake inhibitors (SSRIs) or tricyclic anti-depressants. Lifestyle changes may include exercise, adequate rest, and proper nutrition, in addition to measures for relieving anxiety.

Drug therapy is sometime disadvantageous because the patient becomes dependent upon the drug treatment of choice, such as benzodiazepines or selective serotonin reuptake inhibitors, thus enhancing stress-related withdrawal symptoms. Also, conventional methods of treatment fail in that they do not address the physiochemical changes that occur with anxiety-related diseases.

What is therefore needed are improved methods of, compositions for, and treatment protocols for treating anxiety-related disorders.

What is also needed are improved methods of, compositions for, and treatment protocols for treating anxiety-related disorders, in which the underlying pathology of the disorder is addressed.

SUMMARY OF THE INVENTION

The present invention relates to methods of and compositions for treating and relieving symptoms and disease associated with indications caused by a physiological drive to alleviate a sensation of anxiety. In one treatment method, methods of, and compositions for, modulating the expression of certain $GABA_A$ receptor subunits are used to treat or ameliorate anxiety-related disorders and depressive disorders associated with physiological tolerance to endogenous neurosteroids.

More specifically, the present invention relates to methods of, devices for, and treatment protocols for using pharmaceutical compositions from a class of compounds that modulates $GABA_A$ by modulating the expression of the $GABA_A$ receptor $\alpha_4$ subunit relative to the $GABA_A$ receptor $\alpha_1$ subunit. The treatment of choice is one that resets the compositional profile of the GABA receptor, and more specifically, the $GABA_A$ subunits, into a normal or a pre-tolerance state.

The multiple phase treatment methodology of the present invention employs one or more compounds to reset physiochemical changes, and thus alleviate a disease state, that are caused by the brain's unconscious drive to alleviate anxiety arising from the dysregulation of endogenous neurosteroids.

In one embodiment, the present invention is directed towards treating indications that arise from the drive to address an endogenous neurosteroid "withdrawal". Specifically, diseases such as generalized anxiety disorder; panic disorder; specific and social phobias; obsessive compulsive disorder; post-traumatic stress disorder; and eating disorders, including anorexia nervosa, bulimia nervosa, and binge eating disorder, have, as part of their cause, a biologically detrimental physiological and psychological response to addressing anxiety brought on by endogenous neurosteroid withdrawal.

The present invention also provides methods that, in a first stage, improve an individual's physiological receptivity to treatment. In particular, the methodology is directed toward preventing the up-regulation of endogenous neuroactive steroids or actively down-regulating the production of endogenous neuroactive steroids to avoid cross-tolerance.

The present invention also provides methods that, in a second stage, employs methods of, and compositions for, modulating the expression of certain $GABA_A$ receptor subunits, thus treating the withdrawal symptoms associated with psychological and physiological addiction and dependence in a comprehensive treatment plan. The present invention also relates to optionally employing conventional treatment programs in combination with the methods of and compositions of the present invention in a comprehensive treatment plan.

Methods are provided for treating an anxiety disorder by administering a compound from the class of compounds that modulates $GABA_A$ receptor expression.

In one embodiment, the method includes the steps of assessing a patient for treatment compatibility; preparing a patient for treatment; and administering a compound from the class of compounds that modulates $GABA_A$ receptor expression to a patient.

Methods are also provided for treating obsessive compulsive disorder by administering a compound from the class of compounds that modulates $GABA_A$ receptor expression.

Methods are also provided for treating an eating disorder by administering a compound from the class of compounds that modulates $GABA_A$ receptor expression.

The present invention also provides a class of compounds, and methods of identifying such compounds, that modulates the expression of certain $GABA_A$ receptor subunits. More specifically, the compound of choice is one that a) acts as a partial agonist of $GABA_A$; b) inhibits the upregulation of the $GABA_A$ receptor $\alpha_4$ subunit and/or increases the relative ratio of the $GABA_A$ receptor $\alpha_1$ subunit to the $GABA_A$ receptor $\alpha_4$ subunit; and c) does not cause the upregulation of the $GABA_A$ receptor $\alpha_4$ subunit and/or does not cause the decrease of the relative ratio of the $GABA_A$ receptor $\alpha_1$ subunit to the $GABA_A$ receptor $\alpha_4$ subunit once the composition is no longer present in the patient's system.

It is therefore an object of the invention to provide methods and compositions for inhibiting the formation of neurosteriods.

It is another object of the invention to provide methods and compositions for modulating chloride channels such as $GABA_A$ receptors.

It is another object of the invention to provide methods and compositions for treating symptoms of anxiety-related disorders.

Another object of the invention is to provide for the use of a $GABA_A$ receptor modulator in the preparation of a medicament to treat an anxiety disorder, obsessive compulsive disorder or an eating disorder.

Another object of the invention is to provide for the use of a neurosteroid production inhibitor in the preparation of a medicament to treat an anxiety disorder, obsessive compulsive disorder or an eating disorder.

These and other objects, features and advantages of the present invention will become apparent after a review of the following detailed description of the disclosed embodiments and claims, and the drawings provided.

BRIEF DESCRIPTION OF THE DRAWINGS

The Detailed Description should be considered in light of the drawings, as briefly described below:

FIG. 2 illustrates the internal thought filtering mechanism in a person's brain;

FIG. 3b is a second schematic presentation of a plurality of $GABA_A$ receptor subunits;

FIG. 3c is an illustration of the insensitivity of the modulated $GABA_A$ receptor to benzodiazepines. Note the $\alpha 1$ subunit: $\alpha 1 \beta 2 \gamma 2$-containing $GABA_A$ receptors are the most common GABA receptors in the brain.

DETAILED DESCRIPTION OF THE INVENTION

I. Introduction

Figure 1:
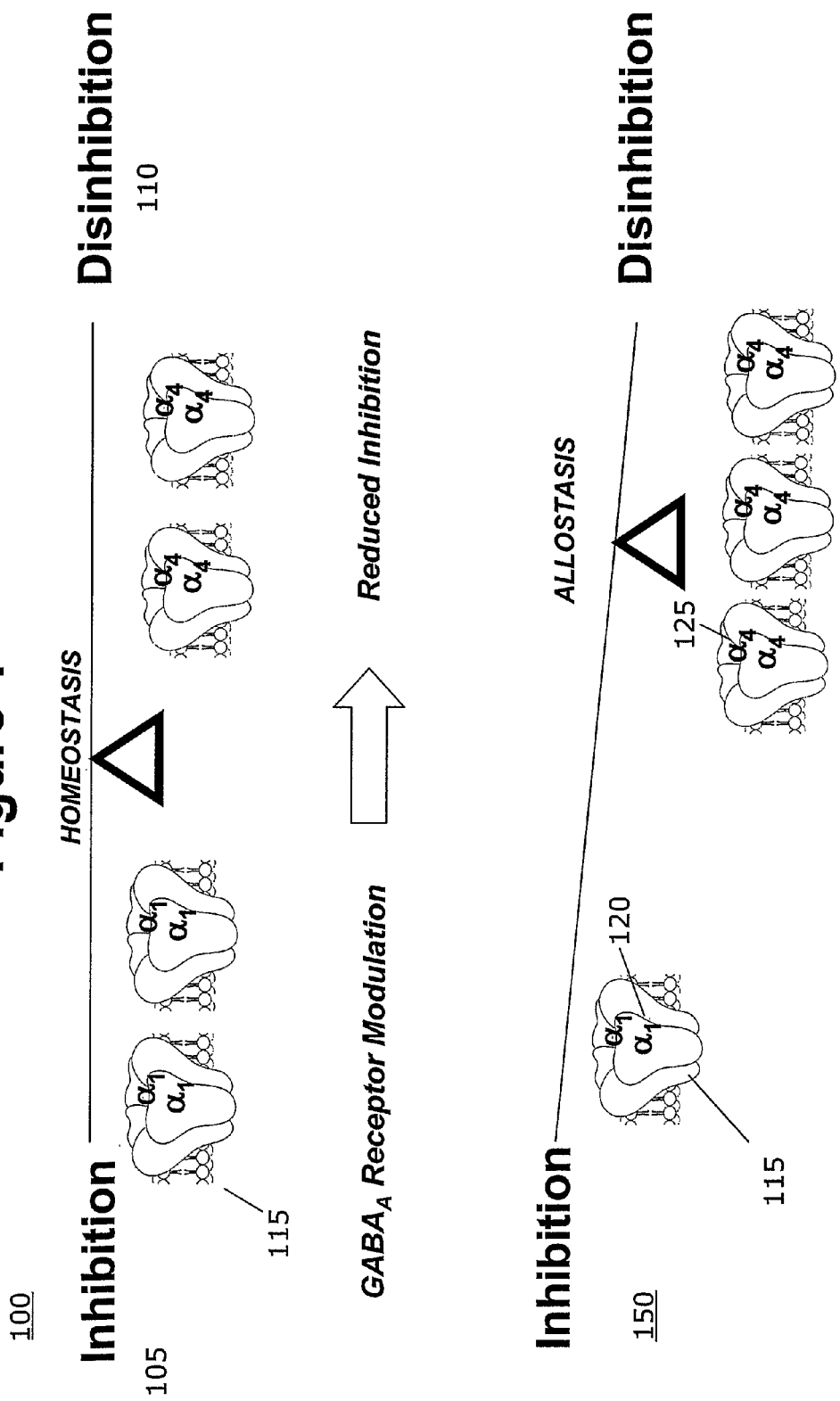
FIG. 1 illustrates the spectrum between inhibition and substantially or completely reduced inhibition via the direct and/or indirect allosteric modulation of $GABA_A$.

Anxiety-related diseases are caused by behavior that arises from an intense desire to manage and/or avoid anxiety experienced during endogenous neurosteroid withdrawal. More specifically, the endogenous neurosteroid allopregnanolone is implicated in the development and course of various mental and maladaptive disorders. Allopregnanolone modulates behavioral and biochemical responses to acute and chronic stress, anxiety, depression, aggressiveness, convulsions, anesthesia, sleep, memory, pain and feeling, similar to the effect of GABA. Allopregnanolone acts via at least two mechanisms, including indirectly by upregulating GABA-binding to the $GABA_A$ receptor, thus increasing the flow of chloride ions into the ion channel, or by directly increasing the flow of chloride ions into the ion channel. The mechanism is described in greater detail below.

One method of addressing endogenous neurosteroid withdrawal is to engage in activities which increase endogenous neurosteroid production, such as activities which cause stress. Stress activates adaptive responses and disrupts homeostasis—the brain's internal balance. Homeostasis can either self-correct allowing the brain to regain its normal equilibrium, or cause the brain to be in either an over-aroused or under-aroused state. Allostasis is the term used to describe these adaptive responses and is further characterized by the brain's ability to maintain stability or homeostasis through change. When the systems involved in allostasis do not shut off when not needed, or do not activate when needed, the brain experiences a drive to address this inactive or constantly active state, often exhibited in the form of anxiety or cravings.

An increase in stress has been shown to increase levels of endogenous neurosteroids in the body and can sometimes result in tolerance to the neurosteroid. Anxiety is the result of the subsequent withdrawal from this increased level of neurosteroids. While engaging in activities that cause stress do increase the level of endogenous neurosteroids, this phenomenon can have detrimental effects on the rest of the body, particularly if the induced stress is physiologically dangerous, i.e. starvation in the case of anorexia or vomiting in the case of bulimia. Consequently, numerous stress-related, anxiety-related or depressive diseases and disorders may be more accurately characterized as diseases further characterized and caused by an individual's need to avoid adverse effects. This loss of inhibitory control contributes to craving and irrational behavior to engage in activities regardless of consequences.

It has been demonstrated that withdrawal from the neurosteroid $3\alpha,5\alpha$-allopregnanolone after chronic administration of progesterone, increases anxiety and up-regulates the $\alpha_4$ subunit expression of the $GABA_A$ receptor. In a non-tolerant subject, the most common $GABA_A$ receptor in the brain is the $\alpha_1 \beta_2 \gamma_2$ receptor, also referred to as a benzodiazepine sensitive receptor. Upon endogenous neurosteroid withdrawal or a decrease in the level of progesterone, the amount $\alpha_1$ subunits decrease relative to the amount of $\alpha_4$ subunits. Withdrawal from the endogenous neurosteroid often causes symptoms of depression, anxiety and impulsivity, as GABA uptake is decreased due to the reduced number of $GABA_A$ receptor $\alpha_1$ subunits relative to $GABA_A$ receptor $\alpha_4$ subunits. Thus, endogenous neurosteroid regulation, and more specifically, the fluctuation of allopregnanolone, is implicated in a variety of anxiety disorders and depressive disorders.

In one embodiment, the present invention is directed towards treating indications that arise from the drive to address an endogenous neurosteroid "withdrawal". Specifically, diseases such as generalized anxiety disorder; panic disorder; specific and social phobias; obsessive compulsive disorder; post-traumatic stress disorder; eating disorders, including anorexia nervosa, bulimia nervosa, and binge eating disorder; polycystic ovary syndrome and its related disease states; and metabolic syndrome and its related disease states, have, as part of their cause, a biologically detrimental physiological and psychological response to addressing anxiety brought on by endogenous neurosteroid withdrawal.

As mentioned above, certain depressive disorders, including but not limited to major depressive disorder, dysthymic disorder, and seasonal affective disorder (SAD), can also be linked to the fluctuation of allopregnanolone, and have, as part of their cause, a biologically detrimental physiological and psychological response to addressing anxiety brought on by endogenous neurosteroid withdrawal.

Thus, when the $GABA_A$ receptor is dysregulated, the clinical manifestation of this dysregulation is initially anxiety. In addition, the anxiety is often accompanied by compulsive behavior. Certain compulsive behaviors, such as but not limited to drug abuse, gambling, compulsive sexual activity, compulsive eating, and compulsive video game playing, can lead to increased euphoria, neurosteroid production and brain simulation. Subsequent discontinuation of these activities can result in withdrawal syndrome that manifests itself through heightened anxiety and $GABA_A$ regulator dysregulation.

Compulsive eating habits may lead to obesity. The compulsion to eat excessive amounts of food can be attributed, in part, to the consumption of certain CNS stimulating foods. CNS stimulating foods result in increased endogenous neurosteroid levels. Both tolerance to certain foods and subsequent discontinuation of compulsive eating habits can result in withdrawal syndrome that manifests itself through heightened anxiety and $GABA_A$ regulator dysregulation. The tolerance is also associated with an increased need for a particular food or group of foods to provide CNS stimulation to increase neurosteroids. It may be possible to effectively reduce or eliminate this tolerance to certain foods by treating the anxiety associated with the withdrawal of a particular food or group of foods. The result of this would be a decreased need for food which would be beneficial for weight loss.

Additionally, in treating anxiety associated with caloric restrictive diets, it may be possible to structure a diet treatment protocol that enables greater patient compliance. For example, but not limited to such example, strict dieting guidelines are often an important component of maintenance treatment post-bariatric surgery. Bariatric surgery does not address the underlying physiology behind compulsive eating, but rather, the physical symptomatology. Reducing or eliminating the tolerance associated with certain foods by treating the anxiety associated withdrawal from these foods is one method of maintaining patient compliance post-bariatric surgery.

In addition, certain neurodegenerative disorders can be related to $GABA_A$ receptor dysregulation. $GABA_A$ receptor dysregulation, in one embodiment, causes the amount of the $\alpha_4$ subunit to increase relative to the amount of the $\alpha_1$ subunit. The $\alpha_4$ subunit-containing $GABA_A$ receptor is less sensitive to the effects of GABA. As a result, tonic levels of GABA may increase, leading to neuronal apoptosis and deafferation of specialized brain cells. The result may be a neurodegenerative disorder, including, but not limited to Alzheimer's disease, age-related dementia, schizophrenia, and Parkinson's disease.

The present invention is thus directed towards methods of and compositions for treating and relieving symptoms and disease associated with indications caused by a physiological drive to alleviate a sensation of anxiety. More specifically, the present invention is directed towards methods of and compositions for treating and relieving symptoms associated with endogenous neurosteroid withdrawal.

The present invention is also directed towards a methodology for diagnosing a person in an altered $GABA_A$ receptor state. In particular, the methodology is directed toward determining the relative receptivity of a patient to the treatment methodologies of the present invention by qualitatively or quantitatively measuring progesterone levels in a patient, or, more preferably, the allopregnanolone levels within a patient's brain.

The present invention is also directed towards a treatment methodology that, in a first stage, improves a patient's physiological receptivity to treatment. In particular, the methodology is directed toward preventing the up-regulation of endogenous neuroactive steroids or actively down-regulating the production of endogenous neuroactive steroids to avoid cross-tolerance.

In one embodiment the present invention is directed towards optionally employing conventional treatment programs prior to or in conjunction with the methods of and compositions of the present invention in a comprehensive treatment plan.

The present invention is also directed towards a treatment methodology that, in a second stage, employs methods of and compositions for modulating the expression of certain $GABA_A$ receptor subunits, thus treating the withdrawal symptoms, such as anxiety-related disorders and depressive disorders, associated with physiological tolerance to endogenous neurosteroids.

More specifically, the present invention is directed towards methods of, devices for, and treatment protocols for using pharmaceutical compositions from a class of compounds that directly or indirectly modulates $GABA_A$ by modulating the expression of the $GABA_A$ receptor $\alpha_4$ subunit relative to the $GABA_A$ receptor $\alpha_1$ subunit.

The present invention is also directed towards a class of compounds, and methods of identifying such compounds, that modulates the expression of certain $GABA_A$ receptor subunits. More specifically, the compound of choice is one that a) acts as a partial agonist of $GABA_A$; b) inhibits the upregulation of the $GABA_A$ receptor $\alpha_4$ subunit and/or increases the relative ratio of the $GABA_A$ receptor $\alpha_1$ subunit to the $GABA_A$ receptor $\alpha_4$ subunit; and c) does not cause the upregulation of the $GABA_A$ receptor $\alpha_4$ subunit and/or does not cause the decrease of the relative ratio of the $GABA_A$ receptor $\alpha_1$ subunit to the $GABA_A$ receptor $\alpha_4$ subunit once the composition is no longer present in the patient's system.

II. The GABAergic System a. Gamma-Aminobutyric Acid (GABA)

GABA is a neurotransmitter that acts at inhibitory synapses in the brain and spinal cord. The GABA system is found, among other places, in the hippocampus, an area of the brain associated with memory formation. Glutamic acid, or glutamate, is important in brain function, as an excitatory neurotransmitter and as a precursor for the synthesis of GABA in GABAergic neurons. Glutamate activates both ionotropic and metabotropic glutamate receptors, described in further detail below. GABA signals interfere with registration and consolidation stages of memory formation.

b. GABA Receptor Types

The GABA receptors are a group of receptors with GABA as their endogenous ligand. Several classes of GABA receptors are known, including ionotropic receptors, which are ion channels themselves, and metabotropic receptors, which are G-protein coupled receptors that open ion channels via intermediaries. Glutamate and GABA mediate their actions by the activation of their receptors.

The ionotropic GABA receptors ($GABA_A$ receptors) are based on the presence of eight subunit families consisting of 21 subunits ($\alpha_{1-6}$, $\beta_{1-4}$, $\gamma_{1-4}$, $\delta$, $\epsilon$, $\pi$, $\theta$, $\rho_{1-3}$) and display an extraordinarily structural heterogeneity. $GABA_A$ receptors are composed of five circularly arranged, homologous subunits and are important sites of drug action. Most often, the $GABA_A$ receptor isomers comprise two $\alpha$ subunits, two $\beta$ subunits and one $\gamma$ subunit. The metabotropic GABA receptors ($GABA_B$ receptors) consist of two subunits: $GABA_{B1}$ and $GABA_{B2}$. Physiological responses following activation of $GABA_B$ receptors require the co-assembly of $GABA_{B1}$ and $GABA_{B2}$. $GABA_C$ receptors also exist natively.

c. $GABA_A$ Receptor Subunits

The $GABA_A$ receptor system is implicated in a number of central nervous system disorders, making $GABA_A$ receptor ligands potential therapeutic agents. $GABA_A$ receptors are ligand-gated ion channels that belong to the same super family of receptors as glycine, nicotinic cholinergic, and serotonin $5HT_3$ receptors. Enhanced function of several $GABA_A$ receptors accounts for the major actions of benzodiazepines, described in greater detail below. In addition, a number of compounds have exhibited functional selectivity for $GABA_A$ receptors.

The $GABA_A$ receptor complex is a pentameric receptor protein structure formed by co-assembly of subunits from seven different classes. Five subunits are situated in a circular array surrounding a central chloride-permeable pore. It has been suggested that the mechanism for ligand-induced channel opening in nicotinic acetylcholine receptors involves rotations of the subunits in the ligand binding domain. Assuming that $GABA_A$ receptors utilize a similar mechanism for channel opening, since $GABA_A$ receptors belong to the same super family as the nicotinic acetylcholine receptors, large substituents may interfere with the channel opening (steric hindrance) resulting in antagonistic effects of certain compounds. In addition, the activation of GABA receptors will influence several other systems, ultimately resulting in a general acute modification of the overall function of the central nervous system.

The particular combination of subunits yields receptors with different pharmacological and physiological properties, however, the $GABA_A$ receptor composition is not immutable. Withdrawal from anxiolytic benzodiazepines, which produce their effects by facilitating $GABA_A$ receptor mediated inhibition, yields an increase in the steady state mRNA levels of $\alpha_4$ and $\beta_1$ subunit mRNA in both the cortex and hippocampus. It should be noted that the $\delta$ subunit is often associated with $GABA_A$ receptor subtypes containing the $\alpha_4$ subunit.

GABA and $GABA_A$ receptors are involved in disease states such as seizures, depression, anxiety and sleep disorders. GABA and some of the other indirectly or directly acting $GABA_A$ receptor agonists (GABA-mimetics), including allopregnanolone and tetrahydrodeoxycorticosterone respectively, bind specifically to a recognition site located at the interface between an $\alpha$ and a $\beta$ subunit. The classical benzodiazepines, however, such as diazepam and flunitrazepam, bind to an allosteric site located at the interface between an $\alpha$ and a $\gamma$ subunit.

More specifically, GABA binds to the cleft between $\alpha$ and $\beta$ subunits, an action which gates open the chloride channel to allow for the influx of chloride ions into the cell. This typically hyperpolarizes the cell, having an inhibitory action on neuronal activity, by making the membrane potential of the cell more negative, and consequentially, increases the depolarization threshold to generate an action potential.

Most depressant and sedative drugs such as the benzodiazepine tranquilizers, barbiturates, anesthetics and alcohol are believed have a modulatory effect on the $GABA_A$ receptor at unique sites where they can enhance the actions of GABA in accumulating negatively charged chloride ions into the cell, inducing sedative or anesthetic effects.

The conformational restriction of various parts of the molecule of GABA and biosteric replacements of the functional groups of the amino acid leads to a broad spectrum of specific $GABA_A$ agonists. Some of these molecules have played a key role in the understanding of the pharmacology of the $GABA_A$ receptor family.

The absence or presence of a particular $\alpha$ subunit isoform in the $GABA_A$ receptors confers selectivity for certain drugs. Different $\alpha$ subunits also mediate distinct pharmacological actions of benzodiazepines, including sedative-hypnotic and anxiolytic effects. Long-term administration of benzodiazepines results in the development of tolerance to some of the effects of these drugs, thus reducing their clinical efficacy. While the molecular basis for these dependencies remains unclear, tolerance and dependence appear to be related to the pharmacodynamics of benzodiazepines.

Long-term administration of benzodiazepines modifies the expression of genes that encode various $GABA_A$ subunits. These changes in gene expression alter the sensitivity of $GABA_A$ receptors to their pharmacological modulators and thereby underlie the development of tolerance to or dependence on these drugs. The subunit composition of $GABA_A$ receptor determines their affinity for benzodiazepine receptor ligands as well as the efficacy of these ligands. For example, classical benzodiazepine agonists (e.g. diazepam), imidazopyridines, imidazoquinolones and pyrazolopyrimidines show no affinity for or efficacy at $GABA_A$ receptors that contain $\alpha_4$ or $\alpha_6$ subunits.

The subunit composition of native $GABA_A$ receptors plays an important role in defining their physiological and pharmacological function. It is possible to characterize the physiological, pharmacological, and pathological roles of $GABA_A$ receptors by understanding the mechanisms by which the subunit composition of $GABA_A$ receptors is regulated. Thus, the expression of specific $GABA_A$ receptor subunit genes may be affected by various physiological and pharmacological modulators, including but not limited to, pharmacological agents, endogenous neurosteroids, and food.

For example, long-term exposure to and subsequent withdrawal of benzodiazepines, zalpelon, zolpidem, or neurosteroids result in selective changes in the expression of specific $GABA_A$ receptor mRNA, including an increase of the $\alpha_4$ subunit mRNA, and polypeptide subunits and in $GABA_A$ receptor function in cultured cells. Withdrawal from diazepam or imidazenil was associated with both a reduced ability of diazepam to potentiate GABA action and the ability of flumazenil to potentiate GABA action. Chronic benzodiazepine treatment and subsequent withdrawal lead to a change in the receptor subunit composition, and these new synthesized receptors are less responsive to benzodiazepines. The up-regulation of the $\alpha_4$ subunit, however, may be necessarily coupled with the down-regulation of other subunits for the development of benzodiazepine dependence.

Withdrawal of zalpelon or zolpidem, like that of diazepam, induced a marked increase in the amount of $\alpha_4$ subunit mRNA. These effects of zalpelon and zolpidem on $GABA_A$ receptor gene expression are consistent with the reduced tolerance liability of these drugs, compared with that of diazepam, as well as with their ability to induce both physical dependence and withdrawal syndrome.

Ethanol withdrawal-induced increases in the amounts of $\alpha_4$ subunit mRNA and protein are associated with reduced sensitivity of $GABA_A$ receptors to GABA and benzodiazepines. The effects of alcohol are similar to those of drugs that enhance the function of $GABA_A$ receptors, which gate the Cl— currents that mediate most inhibitory neurotransmission in the brain, as described above. Acutely high doses of alcohol potentiate GABA-gated currents at both native and recombinant $GABA_A$ receptors, and chronically alter $GABA_A$ receptor expression. Ethanol elicits its central effects through modulation of neurotransmission mediated by various receptors, especially that mediated by $GABA_A$ receptors. It has been shown that long-term ethanol administration also affects the subunit composition and, consequently, the functional properties of native $GABA_A$ receptors. The pharmacological profile of ethanol is similar to that of benzodiazepine and also results in the development of cross-tolerance and dependence.

Exposure to diazepam at the time of ethanol withdrawal antagonizes the withdrawal-induced increase in the abundance of the $\alpha_4$ subunit mRNA. The replacement of ethanol with diazepam also blocked the ethanol withdrawal-induced impairment in cellular metabolism. Cells exposed to GHB at the time of ethanol withdrawal results in an inhibition in the increase in the abundance of the $\alpha_4$ subunit mRNA.

The modulatory action of flumazenil in cells that are exposed to ethanol is similar to that measured in cells not exposed to ethanol. In contrast, however, in ethanol withdrawn cells, 3 µM flumazenil potentiates the GABA evoked Cl— current consistent with the ethanol withdrawal-induced up-regulation of the $\alpha_4$ subunit in these cells. The substitution of 10 µM diazepam or 100 mM GHB for ethanol negated the positive modulation of 3 µM flumazenil induced by ethanol withdrawal.

The presence of the $\alpha_4$ subunit in recombinant $GABA_A$ receptors is associated with a reduced sensitivity to classical benzodiazepine agonists and to zolpidem as well as with a distinct pattern of regulation (positive rather than no allosteric modulation) by flumazenil.

In general, chronic treatment with agonists that act at different sites of the $GABA_A$ receptor results in changes in the biochemical and functional properties of the receptor that are accompanied by changes in the abundance of specific receptor subunit mRNAs. In addition, chronic treatment with substances that modulate $GABA_A$ function via a neurosteroid pathway results in changes in the biochemical and functional properties of the receptor that are accompanied by changes in the abundance of specific receptor subunit mRNAs. The observation that the ethanol withdrawal-induced increase in the expression of the $\alpha_4$ subunit gene in cultured cerebellar granule cells is prevented by diazepam is consistent with the fact that benzodiazepine treatments are effective in treating alcohol withdrawal symptoms in humans. Thus, a rapid and marked increase in the abundance of the $\alpha_4$ subunit induced by ethanol withdrawal might therefore contribute to the development of diazepam-sensitive withdrawal symptoms in humans.

III. GABA and Neurosteroids

Characterizations of the role of $GABA_A$ receptors require an understanding of the mechanisms by which subunit composition is regulated. The long-term administration of sedative-hypnotic, anxiolytic, or anticonvulsant drugs can affect expression of $GABA_A$ receptor subunit genes as well as the drug sensitivity and function of these receptors, suggesting that the mechanisms responsible for such changes might also underlie the physiological modulation of $GABA_A$ receptors by endogenous compounds such as neurosteroids.

The neuroactive steroids 3α-hydroxy-5α-pregnan-20-one (allopregnanolone) and 3α,21-dihydroxy-5α-pregnan-20-one (allotetradihydrodeoxycorticosterone, or THDOC) induce anxiolytic, sedative, hypnotic, and anticonvulsant effects similar to benzodiazepines and other anxiolytic drugs. The concentrations of these neurosteroids are increased in the brain of humans both in response to treatment with anxiogenic, antidepressant or antipsychotic drugs as well as physiological or pathological conditions (such as depression, stress, the luteal phase of the menstrual cycle, and pregnancy) that affect mood and emotional state. Additional studies implicate endogenous allopregnanolone as a physiological regulator of both basal and stress-induced dopamine release in the rat brain.

Steroid metabolites react with the GABA receptor complex to alter brain excitability. Several of these steroids accumulate in the brain after local synthesis or after metabolism of adrenal steroids. Neurosteroids are synthesized in the peripheral and central nervous system, from cholesterol or steroidal precursors imported from peripheral sources. Both progesterone and estrogen alter excitability of neurons of the central nervous system. For example, estrogen reduces inhibition at the $GABA_A$ receptor, enhances excitation at the glutamate receptor, and increases the number of excitatory neuronal synapses. In contrast, progesterone enhances GABA-mediated inhibition, increases GABA synthesis, and increases the number of $GABA_A$ receptors. In particular, progesterone and its metabolites have been demonstrated to have profound effects on brain excitability. The levels of progesterone and its metabolites vary with the phases of the menstrual cycle, decreasing prior to the onset of menses. Progesterone is readily converted to allopregnanolone (3α-OH-5α-pregnan-20-one or 3α,5α-THP) in human brains. Allopregnanolone-induced $GABA_A$ receptor dysregulation has been closely linked to major anxiety-related diseases, thus linking anxiety to allopregnanolone "withdrawal".

Neurosteroids rapidly alter neuronal excitability thorough interaction with neurotransmitter-gated ion channels. Allopregnanolone is a positive potent modulator of the $GABA_A$ receptor and enhances the action which gates open the chloride channel to allow influx of chloride ions into the cell. This typically hyperpolarizes the cell, having an inhibitory action on neuronal activity, and thus allopregnanolone acts as a sedative or anxiolytic agent and decreases anxiety.

$GABA_A$-modulatory allopregnanolone, as described above, is also responsible for producing anxiogenic withdrawal symptoms. The withdrawal profile shown therein is similar to that reported for other $GABA_A$-modulatory drugs such as the benzodiazepines, barbiturates, and ethanol. Thus, the actions of neuroactive steroids on traditional transmitter receptor in the brain lead to alterations in the $GABA_A$ receptor subunit composition that result in changes in the intrinsic channel properties of the receptor and behavioral excitability. Changes are also associated with significant increases in both the mRNA and protein for the $\alpha_4$ subunit of the $GABA_A$ receptor in the hippocampus. It has also been demonstrated that chronic administration of progesterone inhibits the upregulation of the $\alpha_4$ subunit of the $GABA_A$ receptor and/or suppresses receptor activity.

Thus, the endogenous neurosteroid allopregnanolone exhibits withdrawal properties, similar to GABA-modulators such as tranquilizers and alcohol, as described above, increasing anxiety susceptibility following abrupt discontinuation after chronic administration. The increase in neuronal excitability has been attributed to upregulation of the $GABA_A$ $\alpha_4$ subunit. Thus, the $\alpha_4\beta_2\gamma$ is preferentially expressed following hormone withdrawal. Blockade of the $\alpha 4$ gene transcript prevents withdrawal properties.

The increase in expression of the $GABA_A$ receptor $\alpha_4$ subunit relative to the $GABA_A$ receptor $\alpha_1$ subunit can thus be attributed to many factors. These include, but are not limited to 1) compositions, both endogenous and exogenous, which, upon withdrawal, increase the $GABA_A$ receptor $\alpha_4$ subunit relative to the $GABA_A$ receptor $\alpha_1$ subunit; and 2) compositions, both exogenous or endogenous that result in the increase of expression of the $GABA_A$ receptor $\alpha_4$ subunit or the decrease of expression of the $GABA_A$ receptor $\alpha_1$ subunit.

Certain substances, both endogenous and exogenous, can cause modifications in the allostatic control of $GABA_A$, directly or indirectly, via an endogenous neurosteroid pathway. Most substances that cross the blood-brain barrier in sufficient quantity can stimulate a neuroprotective, neurosteroid response. In general, the more neuroexcitatory the substance, the more neurosteroid response is achieved. With the up-regulation of neurosteroids, $GABA_A$ receptor activity is enhanced, causing a constant state of activation which, over time, may cause neurosteroid tolerance. Therefore, once the neuroexcitatory substance is no longer present, the brain's neurosteroid levels will decrease to natural levels, causing the individual to go through a state of "withdrawal" from the neurosteroid.

In the course of this "withdrawal", certain $GABA_A$ receptor subunits may be expressed, or suppressed, in a manner that causes the person's brain to be susceptible to greater feelings of anxiety. In particular, his brain's $GABA_A$ receptor $\alpha_1$ subunits decrease in relative amounts to $GABA_A$ receptor $\alpha_4$ subunits. As a result of neurosteroid "withdrawal" and the subsequent up-regulation of $\alpha_4$ subunits relative to $\alpha_1$ subunits, the GABA receptor is no longer effectively modulated by GABA, and, therefore, results in the person experiencing a greater sense of anxiety.

In one embodiment, an individual's lowered degree of inhibitory control over his thoughts is caused by the modification of the receptivity of the synaptic $GABA_A$ receptors to the neurotransmitter GABA in the individual's brain. For example, substance abuse diminishes GABA receptivity; thus, the exogenous substance or "drug" modulates the $GABA_A$ receptor. When the user ceases consumption of the exogenous substance, due to changes in the $GABA_A$ receptor composition upon withdrawal (i.e. increased relative amount of $GABA_A$ receptor $\alpha_4$ subunits compared to $GABA_A$ receptor $\alpha_1$ subunits), the receptor is not effectively modulated by GABA, thus causing anxiety.

FIG. 1 illustrates the spectrum between inhibition and disinhibition via the direct and/or indirect allosteric modulation of $GABA_A$. Spectrum 100 further depicts the range between inhibition 105 and disinhibition 110. An increase in an exogenous or endogenous substance that directly or indirectly enhances the function of GABA or the $GABA_A$ receptor 115 can result in an increase in GABA agonism and thus an increase in inhibition, anxiolysis, amnesia, and sedation, and even a comatose state.

However, as mentioned in greater detail above, stress, drug use, and even behavior activates these adaptive responses and disrupts homeostasis—the brain's internal balance. Upon withdrawal of both endogenous and exogenous substances, there is a marked increase in the $\alpha_4$ subunit 120 of relative to the $\alpha_1$ subunit 125 of the $GABA_A$ receptor 115, as shown in spectrum 150. The increase of the $\alpha_4$ subunit 120 of the $GABA_A$ receptor 115 causes the receptor to become insensitive to benzodiazepines and other compositions that act upon and/or enhance the function of GABA and the $GABA_A$ receptor. Therefore, when the systems involved in allostasis do not self-regulate (i.e. do not shut off when not needed or do not activate when needed), the brain experiences a compensatory drive to address this inactive or constantly active state, often exhibited in the form of anxiety or cravings.

IV. Anxiety and Inhibition

Anxiety may be defined in a plurality of ways, including a vague unpleasant emotion that is experienced in anticipation of some, often ill-defined misfortune, a complex combination of the feeling of fear, apprehension and worry often accompanied by physical sensations such as palpitations, chest pain and/or shortness of breath, a feeling of apprehension, fear, nervousness, or dread accompanied by restlessness or tension, and/or a debilitating condition of fear, which interferes with normal life functions. Anxiety is evaluated clinically using diagnostic inventories such as the Hamilton Anxiety Rating Scale (Guy, William, "048 HAMA Hamilton Anxiety Scale," ECDEU Assessment Manual, U.S. Department of Health and Human Services, Public Health Service—Alcohol, Drug Abuse, and Mental Health Administration, Rev. 1976, pp. 194-198) or the Beck Anxiety Inventory (Encephale. 1994 January-February; 20(1): 47-55), which are herein incorporated by reference.

In one embodiment, anxiety comprises a physiological state in which an individual has a lowered degree of inhibitory control over his thoughts, as described above with respect to FIG. 1. Such lowered degree of inhibitory control may be caused by the turning off, inhibition, or otherwise downmodulation of an internal thought filtering mechanism in the person's brain. Referring to FIG. 2, the internal thought filtering mechanism 200 comprises certain centers within a person's prefrontal cortex 205, including the orbitofrontal cortex 210, which is considered responsible for exerting control, and the anterior cingulate 215, which is considered responsible for motivation and drive impulses. These brain centers are substantially affected by certain physiological inputs, such as a reward circuit that comprises the nucleus accumbens 220 and ventral tegmental 225 areas of the brain.

When normally regulated, the orbitofrontal cortex 210 can exert control over a person's thoughts and avoid having an individual feel "overwhelmed" by vague, unpleasant emotions and feelings of fear, apprehension and worry. If $GABA_A$ receptor functionality is somehow impaired, however, GABA dysregulation occurs and can result in an impaired ability of the orbitofrontal cortex 210 to exert control over a person's thoughts and, therefore, a lowered degree of inhibitory control.

Consequently, the individual becomes compulsively driven to "address" this anxiety by making sure he obtains whatever substance, or engage in whatever activity, his brain believes it needs in order to eliminate the feelings of anxiety, e.g. regain inhibitory control over his thoughts. Therefore, it is the physiological drive to address feelings of anxiety that causes an individual to consciously engage in behavior which could be classified as self-destructive, such as substance abuse.

In the absence of a solution to address anxiety, a person is in a constant stress response state which, both psychologically and physiologically, directs the person to search for and obtain a solution to the anxiety. Many indications are implicated as being caused by the physiological drive to address feelings of anxiety. As discussed below, certain indications are caused by the psychological addiction and physiological dependence upon various substances, both exogenous and endogenous.

Exogenous substances, such as opioids, benzodiazepines, cannabis, caffeine, nicotine, and other drugs, directly or indirectly affect $GABA_A$ receptor functionality and, when those exogenous substances are withheld from an individual, cause the expression of the $GABA_A$ receptor $\alpha_4$ subunit (hereinafter generally referred to as the $\alpha_4$ subunit) to increase relative to the expression of the $\alpha_1$ subunit.

In particular, during use, such substances may directly or indirectly stimulate $GABA_A$ via a neurosteroid mediated pathway. When those substances are later withheld, the amount of $\alpha_4$ subunits relative to $\alpha_1$ subunits increases. This ratio change is often temporary and is subject to reversal. However, a distinct pathophysiology emerges when it becomes non-reversing, namely when $\alpha_4$ subunits no longer down-regulate relative to $\alpha_1$ subunits. As described above, when such pathophysiology gets established, the $GABA_A$ receptor therefore becomes less sensitive to benzodiazepines and effectively, modulation by the neurotransmitter GABA, and is less capable of exerting inhibitory control over an individual's thoughts and behavior.

In one embodiment, it is possible to calculate a GABA-active steroid score ("GS Score") for nearly all substances. For every substance that crosses the blood brain barrier, or is active on the central nervous system, there is a minimum threshold level needed of that particular substance to effectively raise levels of GABA-active steroids. Thus, the GS Score correlates direct agonism of $GABA_A$ and the indirect modulation of $GABA_A$ via a neurosteroid mediated pathway, such as, but not limited to allopregnanolone. For example, but not limited to such example, cocaine has a lower GS Score than aspartame, since cocaine is more potent and it takes a lower threshold dose of cocaine to raise levels of GABA-active steroids. The GS Score is a methodology for measuring and assigning a numeric value to the relative addictive properties of substances.

Figure 3A:
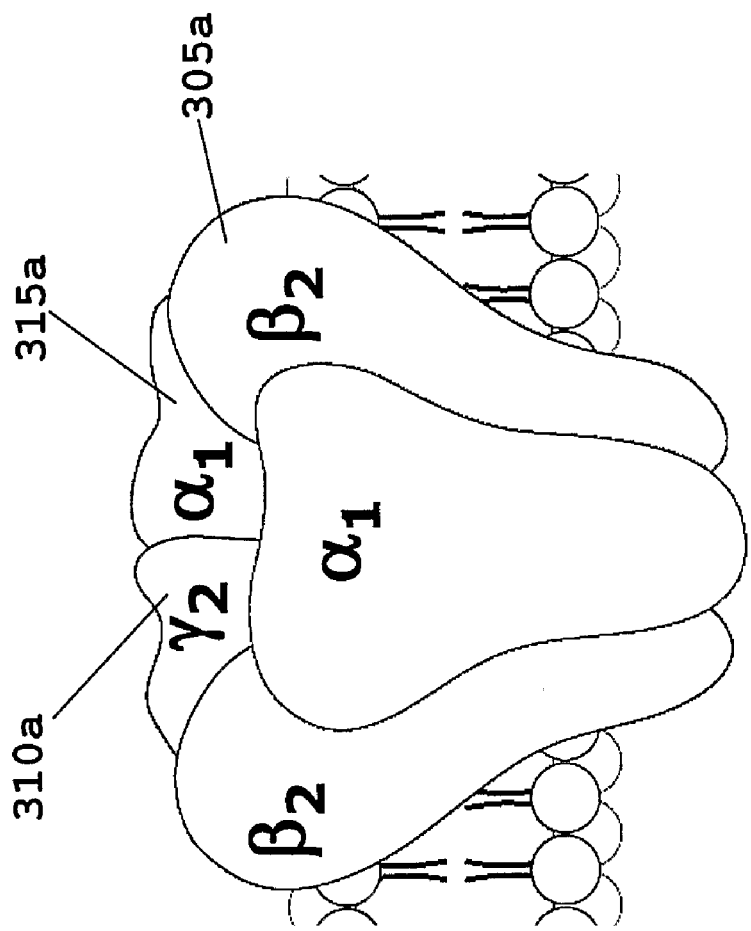
FIG. 3a is a first schematic presentation of a plurality of $GABA_A$ receptor subunits.

Referring to FIG. 3a, a benzodiazepine sensitive $GABA_A$ receptor 300a is shown. The $GABA_A$ receptor comprises a plurality of subunits, including two $\beta_2$ subunits 305a, a $\gamma_2$ subunit 310a, and two $\alpha_1$ subunits 315a. By affecting the functionality and expression of receptor subunit mRNAs, certain endogenous and exogenous substances cause the expression of the $GABA_A$ receptor $\alpha_4$ subunit to increase relative to the expression of the $\alpha_1$ subunit. Referring to FIG. 3b, the modified $GABA_A$ receptor 300b comprises a plurality of subunits, including two $\beta_2$ subunits 305b, a $\gamma_2$ subunit 310b, and two $\alpha_4$ subunits 315b. As shown in FIG. 3c, the $GABA_A$ receptor therefore becomes less sensitive to benzodiazepines and effectively, modulation by the neurotransmitter GABA, and is less capable of exerting inhibitory control over an individual's thoughts and behavior.

Endogenous substances may also have similar effects. Specifically, GABA-modulatory steroids, such as progesterone and deoxycorticosterone (DOC) and their metabolites allopregnanolone and tetrahydrodeoxycorticosterone respectively, affect $GABA_A$ receptor functionality and thus, when progesterone or DOC is decreased or "withdrawn" in an individual, cause the expression of the $GABA_A$ receptor $\alpha_4$ subunit to increase relative to the expression of the $\alpha_1$ subunit.

In addition, an increase in the level of endogenous neurosteroid is associated with tolerance. Thus, engaging in activities that increase neurosteroid production is an often temporary solution, because as described above, a distinct pathophysiology emerges and when it becomes non-reversing, namely when $\alpha_4$ subunits no longer down-regulate relative to a1 subunits. This loss of inhibitory control impairs an individual's ability to act on cravings and thus contributes to irrational behavior to engage in activities regardless of consequences.

Many systems within the body are subject to inhibitory control via GABAergic neurons located in the brain. In the event that an endogenous system is subject to inhibitory feedback by GABA, then the dysregulation of GABAa receptors can result in reduced inhibition or disinhibition of that particular system. Thus, it can be determined whether a primary system is dysregulated, and thus disinhibited, often noted because a patient exhibits a particular indication or disease state, and more specifically, a disease state where higher levels of an endogenous marker are present. For example, but not limited to such example, abnormal cholesterol levels are indicative of dysregulation of a primary system. If, however, a primary system is not dysregulated, then it can be determined whether an inhibitory system is disinhibited or dysregulated, and whether that inhibitory system is restored in the presence of endogenous neurosteroids, such as allopregnanolone and progesterone.

For example, but not limited to such example, prolactin inhibits dopamine, and thus when a patient presents with lower levels of dopamine, it is suggested that prolactin is not being subjected to inhibitory feedback, resulting in increased levels of prolactin. Increased levels of prolactin may be, at least in part, due to $GABA_A$ receptor dysregulation, and thus disinhibition.

V. Compositions Used in the Novel Treatment Methodologies of the Present Invention The compositions described herein, and the compounds identified through the screening methodologies described herein, are intended to be used as drugs in the treatment methodologies described below. As used in this description, the term drug is used to refer to prescription or non-prescription pharmaceutical compositions and/or medications that include an active ingredient and, optionally, non-active, buffering, or stabilizing ingredients, including pharmaceutically acceptable carriers or excipients suitable for the form of administration of said pharmaceutical compositions. It should be appreciated that the administration of the drug may be achieved through any appropriate route of administration, for example, orally, inhaled, anally, sublingual, bucally, transdermally, nasally, implant or parenterally, for which it will be formulated using the appropriate excipients for the form of administration.

Table 1 offers an exemplary listing of pharmacological compounds in the classes of compounds described herein. It should be noted however, that Table 1 is not an exhaustive list of all of the compositions that can be used with the present invention and that the present invention is not limited to the use of such compounds.

a. Compounds that Inhibit Neurosteroid Production

In one embodiment, the present invention is directed towards a method of using a compound from a class of compounds that inhibit neurosteroid production ("Inhibitors of Neurosteroid Production"). In one embodiment, the compound is one that inhibits the conversion of progesterone to its metabolite allopregnanolone. In another embodiment, the compound is one that inhibits the conversion of progesterone metabolite 5α-dihydroprogesterone into allopregnanolone.

Figure 4:
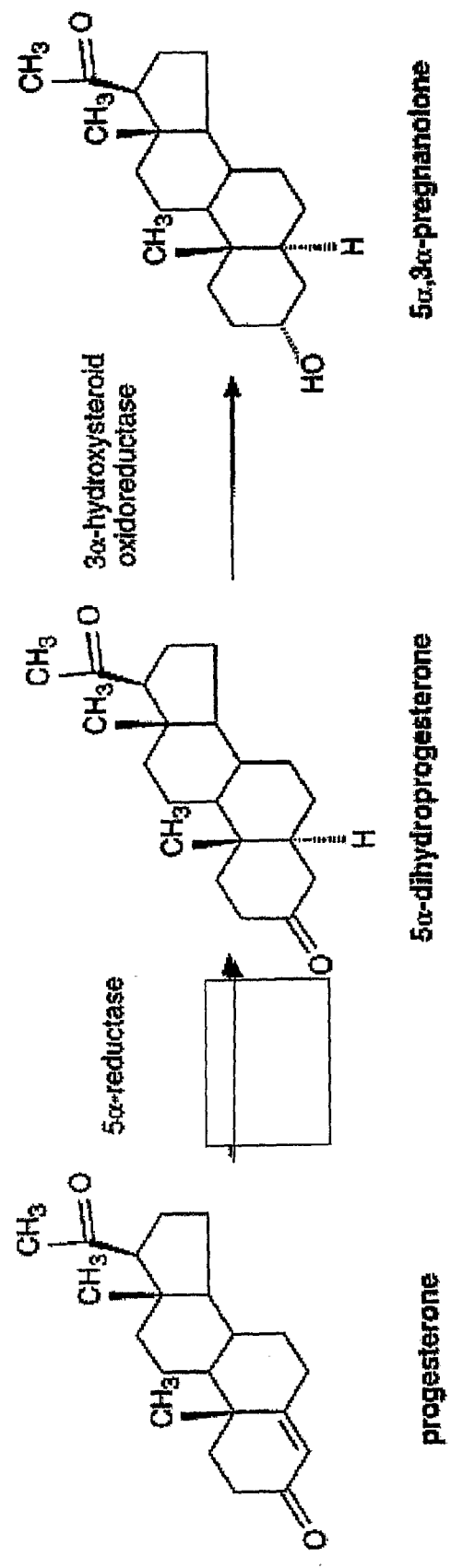
FIG. 4 is a chemical diagram of the blockade of the conversion of progesterone to allopregnanolone via inhibitors of neurosteroid production.

As shown in FIG. 4, progesterone is first converted to 5α-dihydroprogesterone via an enzyme called 5α-reductase. 5α-dihydroprogesterone is then converted to 5α,3α-pregnanolone (allopregnanolone) via the 3α-hydroxysteroid oxidoreductase enzyme.

Reference will now be made to specific classes of inhibitors of neurosteroid production for use in the present invention. While the classes and inhibitors of neurosteroid production are described generally herein, it should be understood to those of ordinary skill in the art that any number of inhibitors of neurosteroid production that prevent the conversion of progesterone into its metabolite allopregnanolone can be used in the present invention and that the list is not exhaustive.

In one embodiment, an individual is administered a therapeutically effective amount of a 5-alpha-reductase inhibitor which blocks the conversion of progesterone into allopregnanolone. One exemplary 5-alpha-reductase inhibitor is finasteride or analogs or derivatives thereof. Preferably, the 5α-reductase inhibitor is capable of acting as a Type I inhibitor, a Type II inhibitor, or a combination thereof, and inhibits the 5α-reductase enzyme from converting progesterone to 5α-dihydroprogesterone and thus from creating progesterone metabolite allopregnanolone.

There are currently accepted dosing regimens for 5-alpha-reductase inhibitors. The present invention contemplates operating within the maximum limits of currently accepted dosing regimens in order to maximally decrease the production of allopregnanolone and make the individual most receptive to treatment.

In one embodiment, an individual is administered a therapeutically effective amount of a 3-alpha-hyrodxysteroid oxidoreductase inhibitor which blocks the conversion of progesterone metabolite 5α-dihydroprogesterone into allopregnanolone. One exemplary 3-alpha-hyrodxysteroid oxidoreductase is indomethacin or analogs or derivatives thereof. There are currently accepted dosing regimens for 3-alpha-hyrodxysteroid oxidoreductase inhibitors. The present invention contemplates operating within the maximum limits of currently accepted dosing regimens in order to effectively decrease the production of allopregnanolone and make the individual most receptive to treatment.

Bitran et al (1995) have demonstrated that treatment with a 5-alpha-reductase inhibitor prevents the conversion of progesterone to allopregnanolone and eliminates the anxiolytic activity of progesterone. In addition, it has been suggested that the anxiogenic withdrawal properties of allopregnanolone can be prevented by previous administration of a 3α-hydroxysteroid oxidoreductase blocker such as indomethacin.

i. 5α-Reductase Inhibitors

The 5α-reductase inhibitors are a group of drugs with anti-androgenic activity that effectively decrease the amount of the 5α-reductase enzyme and thus inhibit neurosteroid production.

1. Finasteride

Finasteride is a synthetic 4-azasteroid compound, and is a 5alpha-reductase inhibitor. Finasteride is 4-azaandrost-1-ene-17-carboxamide, N-(1,1-dimethylethyl)-3-oxo-,(5α,17β)-. The empirical formula of finasteride is $C_{23}H_{36}N_2O_2$ and its molecular weight is 372.55.

Finasteride is a competitive and specific 5α-reductase inhibitor. Finasteride has no affinity for the androgen receptor and has no androgenic, antiandrogenic, estrogenic, antiestrogenic, or progestational effects.

Progesterone is metabolically converted to the $GABA_A$ receptor-potentiating neuroactive steroid allopregnanolone by 5α-reductase isoenzymes followed by 3α-hydroxysteroid oxidoreduction. Finasteride acts as a competitive 5α-reductase inhibitor and thus blocks the production of allopregnanolone from progesterone.

In one embodiment, finasteride is delivered using at least one oral tablet with a total daily dose of less than 10 mg, preferably less than 5 mg. It should be appreciated that, to the extent approved by regulatory authorities, finasteride can also be delivered in gel capsules or via injection or infusion. Finasteride should not be used by women of childbearing age. Finasteride's side effects include breast enlargement and tenderness, skin rash, swelling of lips, abdominal pain, back pain, decreased libido, decreased volume of ejaculate, diarrhea, dizziness, headache, impotence, and testicular pain.

2. Dutasteride

Dutasteride is a synthetic 4-azasteroid compound that is a selective inhibitor of both the Type I and Type II isoforms of the steroid 5α-reductase, an intracellular enzyme. Dutasteride is chemically designated as (5α,17β)-N-{2,5 bis(trifluoromethyl)phenyl}-3-oxo-4-azaandrost-1-ene-17-carboxamide. The empirical formula of dutasteride is $C_{27}H_{30}F_6N_2O_2$, representing a molecular weight of 528.5.

As a competitive Type I and Type II 5α-reductase inhibitor, dutasteride inhibits the conversion of progesterone to allopregnanolone. Dutasteride does not bind to the human androgen receptor.

In one embodiment, dutasteride is delivered using at least one capsule with a total daily dose of less than 10 mg, preferably less than 0.5 mg. It should be appreciated that, to the extent approved by regulatory authorities, dutasteride can also be delivered in tablets or via injection or infusion. Dutasteride should not be used by women of childbearing age. Dutasteride's side effects include cough, difficulty swallowing, dizziness, fast heartbeat, hives or welts, itching skin, puffiness or swelling of the eyelids or around the eyes, face, lips, or tongue, redness of skin, shortness of breath, skin rash, swelling of face, fingers, feet, and/or lower legs, tightness in chest, unusual tiredness or weakness, wheezing, abnormal ejaculation, decreased interest in sexual intercourse, decreased sexual performance or desire, impotence, inability to have or keep an erection, loss in sexual ability, desire, drive, or performance, or swelling of the breasts or breast soreness.

3. Other 5α-Reductase Inhibitors

The present invention also encompasses the use of other 5-alpha reductase inhibitors, including a) 4-aza-4-methyl-5 alpha-pregnane-3,20-dione (AMPD), which inhibits pituitary progesterone 5-alpha reduction, b) cyproterone acetate, and c) spironolactone, which is a diuretic that blocks two pathways to the production of androgens, or male hormones, one of which is the inhibition of 5α-reductase.

The present invention also encompasses the use of organic sources of 5-alpha reductase inhibition, including organic sources such as saw palmetto. Saw palmetto (Serenoa repens) is a natural source of a 5α-reductase inhibitor. Some studies suggest that it may be comparable to finasteride if taken for six months. Saw Palmetto is advantageous because it is 1) substantially free of side effects and 2) cost effective.

ii. Other Inhibitors of Neurosteroid Production

The present invention further includes the use of 3α-hydroxysteroid oxidoreductase blockers. Gallo and Smith (1993) suggest that the anxiogenic withdrawal property of progesterone could be prevented by previous administration of a 3α-hydroxysteroid oxidoreductase blocker. In one embodiment, indomethacin is used. Indomethacin is a non-steroidal anti-inflammatory drug (NSAID) that reduces fever, pain and inflammation. It is similar to ibuprofen and naproxen. Indomethacin is effective in reducing the production of prostaglandins.

It should be appreciated that any composition that can be used to inhibit neurosteroid production can be used in the present invention. In one embodiment, compounds are preferably screened to determine whether they can be used in the treatment methodologies of the present invention.

Specifically, an appropriate cellular model is used to model the inhibition of neurosteroid production. The efficacy of the composition is measured by measuring the relative levels of progesterone and allopregnanolone in a model prior to the administration of the composition and after the administration of the composition. In cases where the relative levels of progesterone and allopregnanolone decrease after administration, the composition may be suitable as an inhibitor to neurosteroid production.

b. Compounds that Modulate the Expression of Certain $GABA_A$ Receptor Subunits

Molecular biology studies have revealed a high degree of structural heterogeneity of the $GABA_A$ receptors. Development of subtype selective or specific compounds is of key importance for the understanding of the physiological and pathological roles of different GABA receptor subtypes and may lead to valuable therapeutic agents. It has been shown that functional selectivity is obtainable for a number of $GABA_A$ agonists.

Characterizations of the role of $GABA_A$ receptors require an understanding of the mechanisms by which subunit composition is regulated. The long-term administration of sedative-hypnotic, anxiolytic, or anticonvulsant drugs can affect expression of $GABA_A$ receptor subunit genes as well as the drug sensitivity and function of these receptors, suggesting that the mechanisms responsible for such changes might also underlie the physiological modulation of $GABA_A$ receptors by endogenous compounds such as neurosteroids.

The level of efficacy of a partial agonist/antagonist depends upon the disease or dependence in question. Thus, by measuring the level of efficacy or activity of a partial agonist/antagonist at a receptor site, it is possible to determine what the disease state is and determine what conformational changes have occurred in the $GABA_A$ receptor subunits. Based upon this information, certain compositions can be classified according to the changes they cause in $GABA_A$ subunits. In addition, since the GABA binding site in the $GABA_A$ receptor is located at the interface between α and β subunits, the $GABA_A$ antagonists can bind to and stabilize a distinct inactive receptor conformation.

The present invention is thus directed towards a class of compounds that modulates the expression of certain $GABA_A$ receptor subunits. More specifically, the compound is one that serves as an agonist at the $GABA_A$ receptor, and more specifically, at either the $α_4$ subunit or $α_6$ subunit, and is capable of positively potentiating GABA current.

Still more specifically, the compound of choice is one that a) acts a partial agonist of $GABA_A$; b) inhibits the up-regulation of the $α_4$ subunit and/or increases the amount of the $α_1$ subunit relative to the amount of the $α_4$ subunit; and c) does not cause the up-regulation of the $α_4$ subunit and/or does not cause the amount of the $α_4$ subunit to increase relative to the amount of the $α_1$ subunit once the compound is no longer present in the patient's system.

The changes in expression of the $GABA_A$ receptor $α_4$ subunit relative to the $GABA_A$ receptor $α_1$ subunit can be attributed to many factors. These include, but are not limited to 1) compositions, both endogenous and exogenous, that transform the $GABA_A$ receptor $α_4$ subunit relative to the $GABA_A$ receptor $α_1$ subunit and vice versa; 2) compositions that result in the decrease of expression of the $GABA_A$ receptor $α_4$ subunit or the increase of expression of the $GABA_A$ receptor $α_1$ subunit; and 3) compositions that do not modify existing subunit levels, but rather prevent the upregulation of $GABA_A$ receptor $α_4$ subunit.

Thus, the compound of choice is one that effectuates an increase in the expression of the $GABA_A$ receptor $α_1$ subunit relative to the expression of the $α_4$ subunit. This increase in expression of the $α_1$ subunit may be effectuated by one or more of the following: a) upregulating the expression of $α_1$ subunits; b) downregulating the expression of $α_4$ subunits; c) masking $α_4$ subunits; or d) preventing the upregulation of the $α_4$ subunit.

The focus is thus on using a compound from the class of compounds that modulates the expression of certain $GABA_A$ receptor subunits, and more specifically, moves the relative balance of the $α_4$ subunit to the $α_1$ subunit closer to a normal state from an abnormal, allostatic state.

i. Flumazenil

In one embodiment, the present invention relates to the use of a therapeutically effective quantity of a drug, and more specifically, one that modulates the expression of $GABA_A$ subunits, such as, but not limited to, flumazenil, in a methodology for treatment of substance abuse. In one embodiment, the compound may comprise certain imidazobenzodiazepines and derivatives of ethyl 8-fluoro-5,6-dihydro-5-methyl-6-oxo-4H-imidazo-[1,5-a][1,4]benzodiazepine-3-carboxylate, including various substitutions of the carboxylate functional group, such as carboxylic acids, esters, acyl chlorides, acid anhydrides, amides, nitriles, alkyls, alkanes, cycloalkanes, alkenes, alcohols, aldehydes, ketones, benzenes, phenyls, and salts thereof. In another embodiment, the compound comprises flumazenil or carboxylic acids, esters, acyl chlorides, acid anhydrides, amides, nitriles, alkyls, alkanes, cycloalkanes, alkenes, alcohols, aldehydes, ketones, benzenes, phenyls, and salts thereof.

Flumazenil acts a partial agonist of $GABA_A$, inhibits the upregulation of the $α_4$ subunit and/or increases the amount of the $α_1$ subunit relative to the amount of the $α_4$ subunit, and does not cause the upregulation of the $α_4$ subunit and/or does not cause the amount of the $α_4$ subunit to increase relative to the amount of the $α_1$ subunit once the compound is no longer present in the patient's system.

ii. Miltirone

In another embodiment, the compound may comprise miltirone, as described in Mostallino et al., "Inhibition by miltirone of up-regulation of $GABA_A$ receptor $α_4$ subunit mRNA by ethanol withdrawal in hippocampal neurons", European Journal of Pharmacology, 494 (2004) 83-90.

iii. Flavonoids

In another embodiment, the compound may comprise certain flavonoids that act as a partial agonist of $GABA_A$, inhibit the upregulation of the $\alpha_4$ subunit and/or increase the amount of the $\alpha_1$ subunit relative to the amount of the $\alpha_4$ subunit, and does not cause the upregulation of the $\alpha_4$ subunit and/or does not cause the amount of the $\alpha_4$ subunit to increase relative to the amount of the $\alpha_1$ subunit once the compound is no longer present in the patient's system.

It should be appreciated that any composition that can function as described above, can be used in the present invention. In one embodiment, compounds are preferably screened to determine whether they can be used in the treatment methodologies of the present invention. In one embodiment, experiments are conducted to determine whether it functions as a partial agonist of $GABA_A$, inhibits the upregulation of the $\alpha_4$ subunit, and does not cause the upregulation of the $\alpha_4$ subunit once the compound is no longer present in the patient's system. While one of ordinary skill in the art can devise such experiments, an exemplary embodiment of such an experiment is provided in Mostallino et al., "Inhibition by miltirone of up-regulation of $GABA_A$ receptor $\alpha_4$ subunit mRNA by ethanol withdrawal in hippocampal neurons", European Journal of Pharmacology, 494 (2004) 83-90.

VI. Novel Treatment Methodologies

The present invention is directed towards a comprehensive treatment protocol that employs methods of, and compositions for, preparing a patient for treatment and modulating the expression of certain $GABA_A$ receptor subunits. The present invention therefore treats symptoms associated with physiological tolerance to and withdrawal from certain steroids, and in particular endogenous neurosteroids, in the context of a comprehensive treatment plan of behavioral and/or pharmacological treatment.

More specifically, the present invention relates to methods of, devices for, and treatment protocols for using pharmaceutical compositions from a class of compounds that modulates $GABA_A$ by modulating the expression of the $GABA_A$ receptor $\alpha_4$ subunit relative to the $GABA_A$ receptor $\alpha_1$ subunit. The treatment of choice is one that resets the compositional profile of the GABA receptor, and more specifically, the $GABA_A$ subunits, into a normal or a pre-tolerance state.

The multiple phase treatment methodology of the present invention employs one or more compounds to reset physiochemical changes, and thus alleviate a disease state, that are caused by the brain's unconscious drive to alleviate anxiety arising from the dysregulation of endogenous neurosteroids.

In one embodiment, the present invention is directed towards treating indications that arise from the drive to address an endogenous neurosteroid "withdrawal". Specifically, anxiety-related disorders such as generalized anxiety disorder; panic disorder; specific and social phobias; obsessive compulsive disorder; post-traumatic stress disorder; and eating disorders, including anorexia nervosa, bulimia nervosa, and binge eating disorder, have, as part of their cause, a biologically detrimental physiological and psychological response to addressing anxiety brought on by endogenous neurosteroid withdrawal.

Effective treatment of such indications requires addressing the maladaptive behaviors underlying psychological and physiological tolerance to and withdrawal from various endogenous neurosteroids, namely the increased expression of the $GABA_A$ receptor $\alpha_4$ subunit relative to the $\alpha_1$ subunit.

The treatment methodology of the present invention thus incorporates 1) determining if a person is in a receptive state for treatment and/or causing a person to be in a receptive state for treatment and 2) treating a person using appropriate drugs in a comprehensive treatment protocol that includes pre-drug assessment including optional detoxification, treatment, and aftercare. The term "receptive state", as used herein, refers to a physiological state in which the patient is withdrawn from both endogenous and exogenous substances.

As used in this description, the term patient refers to a male or female human being of any race, national origin, age, physiological make-up, genetic make-up, disease predisposition, height, or weight, and having any disease state, symptom or illness.

It should further be appreciated that the methods and processes of the present invention can be implemented in a computer system having a data repository to receive and store patient data, a memory to store the protocol steps that comprise the methods and processes of the present invention, a processor to evaluate patient data in relation to said protocol steps, a network interface to communicate via a network with other computing devices and a display to deliver information to users. In one embodiment, specific protocol steps are stored in said memory and compared against patient data, including behavioral, psychological or physiological profiles, to determine which protocol steps should be applied. Results of the comparison are communicated to a user via a network and other computing devices or display. The methodologies of the present invention are therefore accessed, tailored, and communicated as a software program operating on any hardware platform.

The exemplary treatment methodology of the present invention comprises pre-treatment, co-treatment, and post-treatment phases further comprising various components of an exemplary methodology. As described herein, reference will be made to specific components of the individual phases of the treatment methodology. It should be noted, however, that the individual components comprising each phase of the methodology—pre-treatment, co-treatment, and post-treatment—are interchangeable and may be performed variably, and should be determined on a per-patient basis. Thus, any reference to administering the individual components of the phases of methodology in a particular order is exemplary and it should be understood to one of ordinary skill in the art that the administration of methodology may vary depending on the assessed needs of the patient. Furthermore, while the invention will be described in conjunction with specific embodiments, it is not intended to limit the invention to one embodiment. In addition, many combinations of the methodology components described above are possible; thus, the invention is not limited to such examples as provided.

a. Pre-Treatment/Patient Assessment Phase

Prior to admittance into the treatment program of the present invention, each patient should undergo a pre-treatment analysis. The pre-treatment analysis may be used to determine whether a patient is a candidate for the treatment methodology of the present invention. In addition, the pre-treatment process may be administered to prepare a patient for admittance into the treatment methodology of the present invention. The pre-treatment phase typically includes, but is not limited to a medical history and physical examination, a psychological and behavioral assessment, a determination of required medications, and detoxification if needed to render the patient in a state receptive to treatment.

The treatment methodology for anxiety-related disorders and disease states has multiple phases and components that, in combination, provide a comprehensive and integrated neurological, physiological, and psychosocial approach for the diagnosed patient. Each component has been selected to address specific criteria for anxiety-related disorders and disease states and the corresponding symptoms of endogenous neurosteroid withdrawal, with the objective of restoring a balance in neurological circuits.

The methodology does not address a treatment protocol for a patient in immediate danger of harm to oneself or others, or a patient experiencing an anxiety-related symptom that requires emergency attention, which may be associated with an anxiety-related disorder or disease state. It is, therefore, essential that each patient be assessed and the appropriate treatments be instituted to address immediate patient need, with due consideration for the potential interaction of any medicaments used for this treatment with those used for the immediate emergency treatment.

While the present methodology can be applied to any patient, it is preferred that the patient be equal to or greater than eighteen years old.

i. Complete Physical Examination

Before starting the treatment, the patient undergoes a medical history, physical examination and laboratory assessment, including but not limited to a complete blood count, a biochemical profile [for example, creatinine, glucose, urea, cholesterol (HDL and LDL), triglycerides, alkaline phosphatase, LDH (lactic dehydrogenase) and total proteins], hepatic function tests [GOT, GPT, GGT, bilirubin], electrocardiogram and, if appropriate, pregnancy test and x-ray examinations. Exclusion criteria are applied to ensure no other acute or uncompensated illness exists within the patient and to ensure that the patient does not require, or is currently not taking, a drug that is contraindicated with the $GABA_A$ receptor modulating compound being used.

It should further be noted that certain exclusion criteria should be applied to the screening of patients. The exclusion criteria may be tailored to an outpatient or inpatient treatment scenario. For example, it is preferred not to treat a patient on an inpatient basis for an anxiety-related disorder where the where the patient has current medical or psychiatric problems that, per the screening physician, require immediate professional evaluation and treatment, has current medical or psychiatric problems that, per the screening physician, render the client unable to work successfully with the methodology or with the staff administering the treatment, or has current benzodiazepine and other sedative-hypnotic-anxiolytic use (urine toxicology must be negative).

If a patient is currently under pharmacological treatment for the anxiety-related disorder, as described in greater detail below, the patient should be safely weaned off of the medication under the supervision of the treating physician.

ii. Diagnosis of Anxiety-Related Disorder

It is preferred that the patient meet at least a portion of recognized criteria for anxiety-related and mental disorders, such the in the Diagnostic and Statistical Manual of Mental Disorders 4th edition (DSM-IV). For example, DSM-IV criteria state that anxiety disorders include not only generalized anxiety disorder (GAD), social anxiety disorder (SAD, also known as social phobia), specific phobia and panic disorder (PD), with and without agoraphobia, but also obsessive-compulsive disorder (OCD) and post-traumatic stress disorder (PTSD). While the DSM-IV criteria are known to those of ordinary skill in the art, they are outlined below with respect to the example treatment protocols below.

b. Preparing a Patient for Treatment with the Protocol of the Present Invention (Receptive State for Treatment)

It should be noted that the individual components comprising the preparation phase of the methodology are interchangeable and may be performed variably, and should be adapted to the patient. Thus, any reference to administering the individual components of the preparation phase of the methodology in a particular order is exemplary and it should be understood to one of ordinary skill in the art that the administration of methodology may vary depending on the assessed needs of the patient. In addition, many combinations of the methodology components described above are possible; thus, the invention is not limited to such examples as provided.

i. Assessing Patient's Current Treatment/Industry-Standard Treatment Approaches

In one embodiment, a patient with an anxiety disorder may already be in the process of treatment with a conventional treatment methodology, including, but not limited to the use of selective serotonin reuptake inhibitors. In another embodiment, the patient may be "pre-treated" with standard and/or industry-accepted treatment protocols. If a patient is currently undergoing conventional treatment for the anxiety disorder with which he is diagnosed, the patient is preferably weaned off of the medication at least two to four weeks prior to beginning treatment with the protocol of the present invention. Preferably, before beginning treatment, the amount of the drug remaining in the patient is substantially small. Thus, it is important to consider the elimination half-life of the medication that the patient is currently taking. With some medications, such as SSRI's, even when dosing is stopped, active drug substance will persist in the body for weeks (primarily depending on individual patient characteristics, previous dosing regimen, and length of previous therapy at discontinuation). It is important that these factors are considered when preparing the patient for the treatment protocol of the present invention.

Several exemplary treatment protocols are briefly described in the sections below. It should be noted, however, that the treatment protocols outlined herein are exemplary and any number of treatment protocols may be used with the present invention provided that they are not contraindicated with the use of any of the pharmacological compounds for use with the treatment protocol of the present invention, including but not limited to a compound from the class of compounds that increases the relative expression of the $\alpha_1$ $GABA_A$ subunit relative to the $\alpha_4$ $GABA_A$ subunit and inhibitors of neurosteroid production.

It should also be noted that the pharmacological compounds described with respect to the conventional treatment protocols should be used according to published FDA dosage guidelines, which are herein incorporated by reference. While dosing parameters are not described in detail below with respect to the example treatment protocols, Table 1 offers some exemplary treatment parameters for many of the pharmacological compounds described herein, and is herein incorporated by reference.

Many of the conventional protocols described herein are adapted by the National Guideline Clearinghouse. The National Guideline Clearinghouse™ (NGC) is a comprehensive database of evidence-based clinical practice guidelines and related documents. NGC is an initiative of the Agency for Healthcare Research and Quality (AHRQ), U.S. Department of Health and Human Services. NGC was originally created by AHRQ in partnership with the Americal Medical Association and the American Association of Health Plans (now America's Health Insurance Plans [AHIP]). The NGC mission is to provide physicians, nurses, and other health professionals, health care providers, health plans, integrated delivery systems, purchasers and others an accessible mechanism for obtaining objective, detailed information on clinical practice guidelines and to further their dissemination, implementation and use.

Certain clinical practice guidelines were also adapted from the Expert Consensus Guidelines are being used throughout the country by clinicians, policy-makers, administrators, case managers, mental health educators, patient advocates, and clinical and health services researchers.

As mentioned above, the use of industry-accepted treatment protocols is optional.

ii. Placing a Patient in a State of Withdrawal

After a patient is diagnosed and optionally treated with a conventional treatment protocol for treating an anxiety disorder, the patient is placed in a state of withdrawal. As used herein, the term "withdrawal" refers to a physiological state in which an individual has begun to have adverse psychological and/or physiological effects from not having a bioavailable amount of particular substance or from having a decreasing bioavailable amount of a particular substance. In one embodiment, the particular substance is an endogenous neurosteroid. In another embodiment, the particular substance is allopregnanolone. More specifically, withdrawal can be attributed to an increase in the $GABA_A$ receptor $\alpha_4$ subunit expression relative to the $GABA_A$ receptor $\alpha_1$ subunit.

The treatment methodologies of the present invention include a first step of placing a patient in a state of withdrawal. In one embodiment, a person is placed in a receptive state for treatment by actively inhibiting the upregulation of endogenous neurosteroids and/or causing the downregulation of endogenous neurosteroids. The upregulation of neurosteroids could be caused by a number of external factors, including the ingestion or administration of certain substances, such as caffeine or nicotine, or psychological stress. The present invention therefore includes the step of avoiding all such activities that could result in the upregulation of an individual's neurosteroid level.

In another embodiment, a person is placed in a receptive state for treatment by actively causing the downregulation of endogenous neurosteroids, such as allopregnanolone, through the administration of inhibitors of neurosteroid production that block the production of endogenous neurosteroids and/or their metabolites. The present invention also includes the inhibition of the modulatory effects of neurosteroids on $GABA_A$. By doing so, one accelerates the exposure or upregulation of $\alpha_4$ subunits relative to $\alpha_1$ subunits and ensures that a substantial number of $\alpha_4$ subunits are exposed and available to enhance the efficacy of subsequent treatment steps.

The present invention further includes the step of actively causing the downregulation of endogenous neurosteroids, such as allopregnanolone, through the administration of agents that block the production of endogenous neurosteroids and/or their metabolites. The present invention also includes the inhibition of the modulatory effects of neurosteroids on $GABA_A$. By doing so, one accelerates the exposure or upregulation of $\alpha_4$ subunits relative to $\alpha_1$ subunits and ensures that a substantial number of undesirable subunits are exposed and available for enhanced pharmacotherapeutic efficacy.

Particular methods for baselining endogenous neurosteroid production to a consistent level in the pre-treatment portion of the protocol are discussed below, but the treatment protocol is not limited to such methods. For the methods listed below, the present invention contemplates operating in a dosing range of established safety and efficacy in order to maximally decrease the production of progesterone and make the individual most receptive to treatment.

1. Avoid Stress-Inducing Activities

In one embodiment, the present invention includes the step of avoiding all such activities that could result in the upregulation of an individual's neurosteroid level and the step of actively causing the downregulation of endogenous neurosteroids, such as allopregnanolone. It should be noted that stress-inducing activities depend upon the patient and the patient's general condition. Thus, individual recommendations may be made by the treating physician.

2. Avoid Neurosteroid Production Enhancing Activities

The patient is advised to not engage in activities, or ingest any substances, that could likely increase neurosteroid production. Such activities include sex, stressful activities, fighting, or intense arguing. Such substances include chocolate, illegal drugs, prescription drugs, or over the counter medicines.

Although not preferred because these compositions may serve to increase neurosteroid production, in certain cases, it may be necessary to administer a composition to reduce stress.

In one embodiment, the stress-reducing composition is gabapentin. Gabapentin is an anxiolytic and anticonvulsant medication typically prescribed to patients suffering from epilepsy (effectively lowers brain glutamate concentrations) and has also been used in the treatment of anxiety disorders such as social anxiety disorder and obsessive-compulsive disorder. Prior to administering gabapentin to a patient, it is essential to assess the patient for interactions and contraindications. Gabapentin is to be used in adjunctive therapy in the treatment of epilepsy seizures (partial) and for the management of postherpetic neuralgia. Gabapentin is not appreciably metabolized and is excreted unchanged with an elimination half-life of 5-7 hours. Possible side effects from the use of gabapentin are dizziness, somnolence, other symptoms/signs of CNS depression, nausea, ataxia, tremor, and peripheral edema. In persons with epilepsy, abrupt discontinuation may increase seizure frequency. No clinically significant drug interactions have been reported in the literature.

In another embodiment, the stress-reducing composition is a H1 histamine receptor agonist, such as, but not limited to hydroxyzine. Hydroxyzine is indicated for treatment of generalized anxiety disorder symptoms and for use in the management of withdrawal from substance dependence during both the initial phase of inpatient treatment and post-discharge care (as necessary). It also has anti-emetic and skeletal muscle relaxation benefits and can be used as a sedative. This sedative effect can be useful for treating the sleep-disordered breathing and increased periodic leg movements that contribute to the insomnia often seen in patients recovering from alcohol dependency. This helps address on-going insomnia which, for some patients is significantly associated with subsequent alcoholic relapse.

Hydroxyzine is rapidly absorbed and yields effects within 15-30 minutes after oral administration. In addition, hydroxyzine aids the substance withdrawal process through anxiolytic, anti-nausea, relaxant, and various other properties. It should be noted that the effects of other sedating or tranquilizing agents may be synergistically enhanced with the administration of hydroxyzine. Exemplary trade names of these drugs include Atarax and Vistaril.

3. Avoid Heightened Progesterone Levels In Patient

In an optional embodiment, it is possible to minimize endogenous neurosteroid production by timing the treatment in a manner that avoids heightened progesterone cycles.

In women, progesterone levels are low during the pre-ovulatory phase of the menstrual cycle, rise after ovulation, and are elevated during the luteal phase. Specifically, progesterone levels tend to be <2 ng/ml prior to ovulation, and >5 ng/ml after ovulation. If pregnancy occurs, progesterone levels are maintained at luteal levels initially. With the onset of the luteal-placental shift in support of the pregnancy, progesterone levels start to rise further and may reach 100-200 ng/ml at term. After delivery of the placenta and during lactation, progesterone levels are low.

For example, but not limited to such example, since progesterone levels are highest during the luteal phase of the menstrual cycle, it is preferred not to treat a woman during this time window. Conversely, it is preferred to treat a woman during the pre-ovulatory phase of the menstrual cycle, when progesterone levels are low.

Progesterone levels are low in children, men, and post-menopausal women.

4. Actively Modulate a Woman's Progesterone Levels

In another embodiment, a woman's progesterone is actively modulated by the administration of prescription hormones, such as, but not limited to, contraception with progesterone, that keeps the woman on a constant progesterone level. Such contraception includes progestin implants and levonorgestrel implants. Administration of these compositions will effectively make a woman's progesterone levels constant.

Upon withdrawal of these contraception compositions, the woman's hormone level will decrease, thereby "unmasking" its $\alpha_4$ receptor subunits and placing a woman in a state most receptive to treatment.

The present invention advantageously uses the time gap between when administered progesterone leaves the system and when endogenous progesterone production resumes. In one embodiment, this minimal progesterone point window is preferably when the treatment protocol of the present invention should begin.

In one embodiment, progesterone can be delivered orally, sublingually, via vaginal suppositories, via injection, topically, transdermally, or by implant. The rate of absorption of progesterone is highly dependent upon the administration route. Irrespective of the type used, progesterone, progestin, or other progesterone-like compounds should be administered in sufficient amounts to attain a heightened level of progesterone and then terminated in sufficient time to allow for the progesterone levels to decrease prior to treatment.

It should again be noted that Table 1 offers an exemplary listing of pharmacological compounds in the classes of compounds described herein. Several examples of contraception and recommended dosing parameters are also listed in Table 1.

5. Actively Modulate a Male's or Female's Progesterone Cycle

As mentioned above, various neurosteroid inhibitors prevent the conversion of progesterone into allopregnanolone. In an endogenous case, allopregnanolone is responsible for the modulation of the $GABA_A$ receptors. By compensating for the effects of anxiety and anxiety-related symptoms, endogenous neurosteroids, when elevated, "mask" $GABA_A$ receptors and prevent flumazenil from being able to "re-set" those receptors. The administration of these drugs can effectively drive down endogenous neurosteroid levels.

In one embodiment, the compound is a 5α-reductase inhibitor. Preferably, the 5α-reductase inhibitor is capable of acting as a Type I inhibitor, a Type II inhibitor or a combination thereof and inhibits the 5α-reductase enzyme from converting progesterone to 5α-dihydroprogesterone and thus from creating progesterone metabolite allopregnanolone. In another embodiment, the compound is a 3α-hydroxysteroid oxidoreductase inhibitor, which prevents the 3α-hydroxysteroid oxidoreductase enzyme from converting 5α-dihydroprogesterone into 5α,3α-pregnanolone (allopregnanolone).

While the class of compounds that inhibit neurosteroid production has been described in detail above, an exemplary list of compounds is described in detail in Table 1. It should be noted, however, that the present invention is not limited to such compounds and any compounds that effectively inhibit endogenous neurosteroid production, and in particular, the conversion of progesterone to its metabolite allopregnanolone, can be used with the present invention.

c. Administration of a Compound from the Class of Compounds that Modulates the Expression of Certain $GABA_A$ Receptor Subunits Whether used independently of, or part of, any other treatment approach, the present invention requires a patient to be administered a compound from the class of compounds that modulates the expression of certain $GABA_A$ receptor subunits, as described above. In one embodiment, the compound serves as an agonist at the $GABA_A$ receptor, and more specifically, at either the $\alpha_4$ subunit or $\alpha_6$ subunit, and is capable of positively potentiating GABA current.

It should be noted, however, that the present invention is not limited to such compounds and any compounds that effectively increase the expression of the $\alpha_1$ $GABA_A$ subunit relative to the $\alpha_4$ $GABA_A$ subunit, in a non-transitory manner, can be used with the present invention.

The present invention is directed towards, in one embodiment, the use of a compound that modulates the expression of certain $GABA_A$ receptor subunits, such as flumazenil, in multiple doses for a predetermined time period as part of the treatment methodology. When administered in accordance with the present invention, a therapeutically effective amount of the drug is maintained in the patient, thereby significantly reducing the upregulation of allopregnanolone. The methodology of the present invention also provides for the administration of a compound that modulates the expression of certain $GABA_A$ receptor subunits, such as flumazenil, without significant side effects.

Thus, in one embodiment, a method is provided for the treatment of anxiety-related disorders and disease states that includes the administration to a patient in need of said treatment of a therapeutically effective quantity of flumazenil in multiple doses during predetermined time periods/intervals, until a therapeutically effective quantity of flumazenil to treat anxiety-related disease states has been reached, as measured by quantitative and/or qualitative assessments of, for example, a patient's blood pressure, heart rate, and feelings of anxiety. Thus, it is possible to administer flumazenil in variable doses to obtain the desired therapeutic response, reducing the risk of secondary effects in the patient (as a result of reducing the quantity of drug administered per dose applied).

In another embodiment, a method is provided for the treatment of anxiety-related disorders and disease states that includes the administration to a patient in need of said treatment of a therapeutically effective quantity of flumazenil, usually between 0.5 mg/day and 20 mg/day, between 0.5 mg/day and 15 mg/day, specifically between 1.0 and 3.0 mg/day, and more specifically between 1.5 and 2.5 mg/day, of flumazenil, broken down into multiple doses of flumazenil between 0.1 and 0.3 mg and intended for administration during predetermined time periods or intervals, until said therapeutically effective quantity of flumazenil to treat the disorder has been reached. In one embodiment, the predetermined time period is in the range of 1 and 15 minutes and the "per dose" quantity of flumazenil is between 0.1 and 0.3 mg.

One of ordinary skill in the art would appreciate that the individual doses can range in amount, and the time interval between the individual doses can range in amount, provided that the total dose delivered is in the range of 1.0 mg/day and 3.0 mg/day and the individual doses are delivered at relatively consistent time intervals. Therefore, the time period intervals can range from 1, 2, 3, 4, 5, 6, 7, 8, 9, 10, 11, 12, 13, 14, 15, 16, 17, 18, 19, 20, 21, 22, 23, 24, or 25 minutes or fractions thereof. Doses delivered at each time period, separated by the time intervals, can be between 0.1 and 0.3 mg, or fractions thereof, keeping in mind the total drug delivered is preferably less than 3.0 mg/day. The present invention therefore provides for the delivery of multiple, sequential doses, delivered at substantially consistent time intervals.

Conventional uses of flumazenil comprise either singular doses or much larger doses over shorter periods of time and are directed toward reversing sedative effects of anesthesia, conscious sedation, or benzodiazepine overdose. Further, Romazicon, a brand name for flumazenil marketed by Roche, is expressly indicated to complicate the management of withdrawal syndromes for alcohol, barbiturates and cross-tolerant sedatives and was shown to have an adverse effect on the nervous system, causing increased agitation and anxiety. For a single dose to address anesthesia and conscious sedation, it is conventionally recommended to use a dose of 0.2 mg to 1 mg of Romazicon with a subsequent dose in no less than 20 minutes. For repeat treatment, 1 mg doses may be delivered over five minutes up to 3 mg doses over 15 minutes. In benzodiazepine overdose situations, a larger dose may be administered over short periods of time, such as 3 mg doses administered within 6 minutes. One of ordinary skill in the art would appreciate that such conventional uses of flumazenil are not directed toward the treatment of substance abuse.

In addition, the administration method of the present invention provides a better use of flumazenil to treat the symptoms of withdrawal and to reduce the unnecessary consumption of said drug, thereby increasing convenience and the quality of life of the patient and reducing cost by treating the patient in a very short period of time.

The method for the treatment of anxiety-related disorders and disease states provided by this invention is applicable to any patient who, when the treatment is to begin, has no medical illnesses that would make treatment with a compound that modulates the expression of certain $GABA_A$ receptor subunits, such as flumazenil hazardous or is taking medication contraindicated with a compound that modulates the expression of certain $GABA_A$ receptor subunits.

In one embodiment, a compound that modulates the expression of certain $GABA_A$ receptor subunits, such as flumazenil, is administered until qualitative and quantitative parameters indicative of an anxiety-related disorder are lowered to acceptable ranges.

In one embodiment, a compound that modulates the expression of certain $GABA_A$ receptor subunits, such as flumazenil, is administered at the latter of a) when the patient starts to feel anxious (this is when receptors are "unmasked" as progesterone is substantially no longer converted to allopregnanolone) or b) when it is safe to administer based upon prior drugs given to the patient.

In one embodiment, a compound that modulates the expression of certain $GABA_A$ receptor subunits, such as flumazenil, is administered at any rate, provided that the rate is not detrimental to the patient, as determined by patient self-report of symptoms, or physiological parameters such as heart rate, heart rhythm, or blood pressure.

d. Additional Treatment Options

In some cases, in may be necessary to use, either during or post-treatment, the following optional components of the treatment protocol. The following optional components are exemplary and are dependent upon a variety of factors, including but not limited to responsiveness of the patient to treatment and if there is an indication of a sustained increase in 5-alpha reductase activity.

i. 5-Alpha Reductase Inhibitor

It may be necessary to continually treat a patient with a 5-alpha reductase inhibitor if there is an indication of a sustained increase in 5-alpha reductase activity. 5-alpha-reductase inhibitors have been described in detail above and will not be repeated herein.

ii. Prolactin

In some cases, it may be necessary to treat a patient to resolve increased production of prolactin, due to an increase of estrogen levels caused by a decline in progesterone feedback. A sustained increase in the levels of prolactin leads to impairment of dopamine functionality, characterized by a higher stimulus threshold for dopamine release. Exemplary drugs include dopamine agonists, such as bromocriptine and prescription amphetamines, such as Ritalin and Adderal.

e. Post-Treatment Phase of Protocol

After a patient successfully completes the treatment phase of the methodology of the present invention, each patient will be prescribed a post-treatment regimen to follow, which includes, but is not limited to, the administration of pharmaceutical compositions, outpatient therapy, a diet program, and an exercise regimen. The components of the post-treatment phase of the methodology of the present invention are described in greater detail below.

Before discharge from the hospital, one or more of the following compositions or drugs may be prescribed: gabapentin and fluoxetine hydrochloride. Preferably, the compositions or drugs can be administered in oral form to enable greater patient compliance and convenience. It should be appreciated that, to the extent any of drugs described herein are not available in the jurisdiction in which this invention is being practiced equivalent functioning drugs may be used.

Psychotherapy/behavioral therapy and counseling may be critical for the success of anxiety-related and/or depressive disorders and disease states when using pharmacological adjuncts. Thus, the methodology also provides for a maintenance program that includes medications and incentives for the patient to continue with their treatment process through continuing care programs. Due to the complexity of anxiety-related disorders and disease states, patients benefit most from a combination of pharmacologic and behavioral interventions.

As part of the treatment program, patients may optionally be instructed to attend the outpatient treatment center for several months with decreasing frequency [i.e., once a week for the first three months, once every two weeks during the second three months, and once a month during the third three months].

Likewise, a semi-structured follow-up of cognitive behavior therapy is optionally implemented. Individual and family psychotherapy is focused on a plurality of interventions, including cognitive restructuring, work therapy, prevention of relapse, and stress reduction, aimed at rehabilitating the social, family, work, personal and leisure life of the patient.

Depending upon the results of the initial examination, a universal or patient-specific diet plan may optionally be administered in conjunction with the methodology. Depending upon the results of the initial examination, a universal or patient-specific exercise programs may optionally be administered in conjunction with the methodology.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

VII. Example 1

Protocol for the Treatment of General Anxiety Disorder

Anxiety disorders are often debilitating and chronic conditions that are exacerbated at high times of stress and may be linked to changes in hormone levels in the body. In order to compensate for these hormonal changes, or to increase progesterone as described above, people tend to create more stress in their lives. GABA-modulatory steroids, such as progesterone and its metabolite allopregnanolone, affect GABA receptor functionality and thus, when progesterone is down-regulated in an individual, such as the case is with certain anxiety disorders, the expression of the $GABA_A$ receptor $\alpha_4$ subunit is increased relative to the expression of the $\alpha_1$ subunit. By resetting $GABA_A$ to normal levels of receptor subunits (decrease the amount of $\alpha_4$ and increase the amount of $\alpha_1$, which is more sensitive to binding of GABA and benzodiazepines) it is possible to treat the underlying disease state.

a. Pre-Treatment/Patient Assessment Phase

As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of General Anxiety Disorder

Generalized anxiety disorder is characterized, according to DSM-IV criteria, by long-lasting anxiety that is not focused on any particular object or situation. People with this disorder feel afraid of something but are unable to articulate the specific fear. Because of persistent muscle tension and automatic fear reactions, they may develop headaches, heart palpitations, dizziness, and insomnia. These physical complaints, combined with the intense, long term anxiety, make it difficult to cope with normal daily activities. Diagnostic criteria include:

Excessive anxiety and worry (apprehensive expectation), occurring more days than not, for at least 6 months, about a number of events or activities (such as work or school performance).

The person finds it difficult to control the worry.

The anxiety and worry are associated with three (or more) of the following six symptoms (with at least some symptoms present for more days than not, for the past 6 months): restlessness or feeling keyed up or on edge; being easily fatigued; difficulty concentrating or mind going blank; irritability; muscle tension; sleep disturbance (difficulty falling or staying asleep, or restless, unsatisfying sleep).

The focus of the anxiety and worry is not confined to features of an Axis I disorder, e.g., the anxiety or worry is not about having a panic attack (as in Panic Disorder), being embarrassed in public (as in social phobia), being contaminated (as in obsessive-compulsive disorder), being away from home or close relatives (as in separation anxiety disorder), gaining weight (as in anorexia nervosa), having multiple physical complaints (as in somatization disorder), or having a serious illness (as in hypochondriasis), and the anxiety and worry do not occur exclusively during post-traumatic stress disorder.

The anxiety, worry or physical symptoms cause clinically significant distress or impairment in social, occupational or other important areas of functioning.

The disturbance is not due to the direct physiological effects of a substance (e.g., a drug of abuse, a medication) or a general medical condition (e.g., hyperthyroidism) and does not occur exclusively during a mood disorder, a psychotic disorder, or a Pervasive Developmental Disorder.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

"Clinical guidelines for the management of anxiety: Management of Anxiety panic disorder, with or without agoraphobia, and generalized anxiety disorder in adults in primary, secondary, and community care." Published by the National Guideline Clearinghouse, is herein incorporated by reference.

Traditional treatments for generalized anxiety disorder include pharmacological treatment options, such as benzodiazepines (such as diazepam, alprazolam, clonazepam, lorazepam, and 2-chlordesmethyldiazepam), buspirone, antidepressants (such as extended release venlafaxine, paroxetine, fluvoxamine, and citalopram) and certain tricyclics (such as imipramine and clomipramine). In severe cases, antipsychotics may be used.

ii. Placing a Patient in a State of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-inducing activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1

Male, 30 years old, under DSM IV criteria, has been diagnosed as having general anxiety disorder.

Patient Preparation Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

g. Hypothetical Treatment Example 2

Male, 30 years old, under DSM IV criteria, has been diagnosed as having general anxiety disorder. He is currently under pharmacotherapy, with medications including paroxetine, 20 mg/day and alprazolam, 0.25 mg/day on an as needed basis (maximum 4 mg in 24 hours).

Patient Preparation Step 1: Six weeks prior to scheduled treatment, patient is instructed to decrease paroxetine dosage 10 mg/day for two weeks. Four weeks prior to scheduled treatment, patient is instructed to cease all medications, including alprazolam and paroxetine.

Patient Preparation Step 2: Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

VIII. Example 2

Protocol for the Treatment of Panic Disorder

Panic disorder is characterized by brief attacks of intense terror and apprehension that cause trembling and shaking, dizziness, and difficulty breathing. Although panic attacks sometimes seem to occur out of nowhere, they generally happen after frightening experiences, prolonged stress, or even exercise.

a. Pre-Treatment/Patient Assessment Phase

As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of Panic Disorder

Diagnostic criteria include: A discrete period of intense fear or discomfort, in which four (or more) of the following symptoms develop abruptly and reach a peak within 10 minutes:

Both (1) and (2):
  (1) Recurrent unexpected panic attacks
  (2) At least one of the attacks has been followed by 1 month (or more) of one or more of the following:
    Persistent concern about having additional panic attacks
    Worry about the implications of the attack or its consequences
    A significant change in behavior related to the attacks
  Presence or absence of agoraphobia
  The panic attacks are not due to the direct physiological effects of a substance (eg, a drug of abuse, a medication) or a general medical condition (eg, hyperthyroidism).
  The panic attacks are not better accounted for by another mental disorder.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

"Clinical guidelines for the management of anxiety: Management of Anxiety panic disorder, with or without agoraphobia, and generalized anxiety disorder in adults in primary, secondary, and community care." Published by the National Guideline Clearinghouse, is herein incorporated by reference.

Traditional treatments for panic disorder include pharmacological treatment options, such as buspirone, antidepressants (such as extended release venlafaxine, paroxetine, fluvoxamine, and citalopram) and certain tricyclics (such as imipramine and clomipramine). In severe cases, antipsychotics may be used.

ii. Placing a Patient in a State of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-including activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1

Male, 32 years old, under DSM IV criteria, has been diagnosed as having panic disorder.

Patient Preparation Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

g. Hypothetical Treatment Example 2

Male, 32 years old, under DSM IV criteria, has been diagnosed as having panic disorder. He is currently receiving paroxetine, 40 mg/day.

Patient Preparation Step 1: Eight weeks prior to scheduled treatment, patient is instructed to decrease paroxetine dosage to 20 mg/day for two weeks. Six weeks prior to scheduled treatment, patient is instructed to further decrease paroxetine dosage to 10 mg/day for two weeks. Four weeks prior to scheduled treatment, patient is instructed to cease all medications, including paroxetine.

Patient Preparation Step 2: Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

IX. Example 3

Protocol for the Treatment of Specific Phobia and Social Phobia (Social Anxiety Disorder)

A phobia is a strong, irrational fear and avoidance of an object or situation. The person knows the fear is irrational, yet the anxiety remains. Phobic disorders differ from generalized anxiety disorders and panic disorders because there is a specific stimulus or situation that elicits a strong fear response.

a. Pre-Treatment/Patient Assessment Phase

As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of Specific Phobia

Marked and persistent fear that is excessive or unreasonable, cued by the presence or anticipation of a specific object or situation.

Exposure to the phobic stimulus almost invariably provokes an immediate anxiety response, which may take the form of a situationally bound or situationally predisposed panic attack. In children, the anxiety may be expressed by crying, tantrums, freezing or clinging.

The person recognizes that the fear is excessive or unreasonable. In children, this may be absent.

The phobic situation (s) is avoided or else is endured with intense anxiety or distress.

The avoidance, anxious anticipation, or distress in the feared situation (s) interferes significantly with the person's normal routine, occupational (or academic) functioning, or social activities or relationships, or there is marked distress about having the phobia.

In individuals under 18 years, the duration is at least 6 months.

The anxiety, panic attacks, or phobic avoidance associated with the specific object or situation are not better accounted for by another mental disorder.

ii. Diagnosis of Social Phobia (Social Anxiety Disorder)

A marked and persistent fear of one or more social or performance situations in which the person is exposed to unfamiliar people or to possible scrutiny by others. The individual fears that he or she will act in a way (or show anxiety symptoms) that will be humiliating or embarrassing.

Exposure to the feared social situation almost invariably provokes anxiety, which may take the form of a situationally bound or situationally predisposed panic attack.

The person recognizes that the fear is excessive or unreasonable. In children, this feature may be absent.

The feared social or performance situations are avoided or else are endured with intense anxiety or distress.

The avoidance, anxious anticipation, or distress in the feared social or performance situation (s) interferes significantly with the person's normal routine, occupational (academic) functioning, or social activities or relationships, or there is marked distress about having the phobia.

For individuals under the age 18 years, the duration is at least 6 months.

The fear or avoidance is not due to the direct physiological effects of a substance (eg, a drug of abuse, a medication) or a general medical condition and is not better accounted for by another mental disorder.

If a general medical condition or another mental disorder is present, the fear in Criterion A is unrelated to it.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

Phobias are most commonly treated using a combination of pharmacotherapy and cognitive therapy. Popular pharmacotherapy treatments include benzodiazepines, beta-blockers, and selective serotonin re-uptake inhibitors. Table 1 provides listings and examples, including dosing information of various compounds in the classes listed above that may be used to treat panic disorder and will not be repeated herein.

ii. Placing a Patient in a State of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-inducing activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1

Male, 26 years old, under DSM IV criteria, has been diagnosed as having a social phobia (or social anxiety disorder).

Patient Preparation Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

g. Hypothetical Treatment Example 2

Male, 26 years old, under DSM IV criteria, has been diagnosed as having social anxiety disorder. He is currently under pharmacotherapy, with medications including paroxetine, 20 mg/day and alprazolam, 0.25 mg/day on an as needed basis (maximum 4 mg in 24 hours).

Patient Preparation Step 1: Six weeks prior to scheduled treatment, patient is instructed to decrease paroxetine dosage 10 mg/day for two weeks.

Four weeks prior to scheduled treatment, patient is instructed to cease all medications, including alprazolain and paroxetine.

Patient Preparation Step 2: Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

X. Example 4

Protocol for the Treatment of Obsessive Compulsive Disorder a. Pre-Treatment/Patient Assessment Phase As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of Obsessive Compulsive Disorder (OCD)

Obsessive compulsive disorder is a type of anxiety disorder characterized by obsessions and/or compulsions. Obsessions are distressing, repetitive thoughts or images that the individual often realizes are senseless. Compulsions are repetitive behaviors that the person feels forced or compelled into doing, in order to relieve anxiety. OCD is characterized by either obsessions or compulsions:

Obsessions as defined by (A), (B), (C) and (D):
    A. Recurrent and persistent thoughts, impulses, or images that are experienced, at some time during the disturbance, as intrusive and inappropriate and that cause marked anxiety or distress.
    B. The thoughts, impulses or images are not simply excessive worries about real-life problems.
    C. The person attempts to ignore or suppress such thoughts, impulses or images, or to neutralize them with some other thought or action.
    D. The person recognizes that the obsessional thoughts, impulses or images area product of his or her own mind (not imposed from without as in thought insertion).

Compulsions as defined by (A) and (3):
    A. Repetitive behaviors (e.g., hand washing, ordering, checking) or mental acts (e.g., praying, counting, repeating words silently) that the person feels driven to perform in response to an obsession, or according to rules that must be applied rigidly.
    B. The behaviors or mental acts are aimed at preventing or reducing distress or preventing some dreaded event or situation; however, these behaviors or mental acts either are not connected in a realistic way with what they are designed to neutralize or prevent, or are clearly excessive.

At some point during the course of the disorder, the person has recognized that the obsessions or compulsions are excessive or unreasonable. Note: This does not apply to children.

The obsessions or compulsions cause marked distress, are time-consuming (more than 1 hour a day), or significantly interfere with the person's normal routine, occupational (or academic) functioning, or usual social activities or relationships.

If another Axis I disorder is present, the content of the obsessions or compulsions is not restricted to it.

5. The disturbance is not due to the direct physiological effects of a substance or a medical condition.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

The following guideline is adapted from "Obsessive-Compulsive Disorder Patient/Family Handout" published at http://www.psychguides.com/oche.php, which is herein incorporated by reference.

OCD is typically treated with cognitive-behavioral psychotherapy (CBT) and medication with pharmacotherapy, usually a selective serotonin re-uptake inhibitor. Popular medications include clomipramine, fluoxetine, fluvoxamine, paroxetine, and sertraline.

It may also be useful to supplement the SSRI with an anxiety-reducing medication, such as clonazepam or alprazolam, in patients with a high level of anxiety. In addition, a high potency neuroleptic, such as haloperidol or risperidone, may be used when tics or thought-disorder symptoms are present.

It is recommended that a patient stop any medication gradually.

ii. Placing a Patient in a State of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-inducing activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1

Female, 27 years old, under DSM IV criteria, has been diagnosed as having Obsessive Compulsive Disorder.

Patient Preparation Six weeks prior to scheduled treatment, female patient is administered oral contraceptives. One week prior to scheduled treatment, the administration of oral contraceptives is terminated. Three days prior to scheduled treatment, the patient is instructed to not engage in any stress-inducing activities or ingest any substances that would likely increase neurosteroid production.

Day 1 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Day 2 of Treatment: Female patient is administered flumazenil, via infusion, at a rate of at least 2.5 mg/day.

Day 3 of Treatment: Female patient is evaluated to determine if a third day of treatment is necessary. If she continues to report feelings of anxiety or cravings, she is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Female patient is instructed to attend the outpatient treatment center for several months with decreasing frequency [i.e., once a week for the first three months, once every two weeks during the second three months, and once a month during the third three months]. If feelings of anxiety return, she is scheduled to repeat at least one day, and up to three days, of flumazenil treatment.

g. Hypothetical Treatment Example 2

Female, 27 years old, under DSM IV criteria, has been diagnosed as having Obsessive Compulsive Disorder. Female patient is currently undergoing cognitive behavioral therapy and pharmacotherapy. She is currently taking paroextine 40 mg per day.

Patient Preparation: Eight weeks prior to scheduled treatment, patient is instructed to decrease paroxetine dosage to 20 mg/day for two weeks. Six weeks prior to scheduled treatment, patient is instructed to further decrease paroxetine dosage to 10 mg/day for two weeks.

Four weeks prior to scheduled treatment, patient is instructed to cease all medications for this course of treatment, including paroxetine.

Additional Patient Preparation: Six weeks prior to scheduled treatment, female patient is administered oral contraceptives. One week prior to scheduled treatment, the administration of oral contraceptives is terminated. Three days prior to scheduled treatment, the patient is instructed to not engage in any stress-inducing activities or ingest any substances that would likely increase neurosteroid production, Day 1 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Day 2 of Treatment: Female patient is administered flumazenil, via infusion, at a rate of at least 2.5 mg/day.

Day 3 of Treatment: Female patient is evaluated to determine if a third day of treatment is necessary. If she continues to report feelings of anxiety or cravings, she is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Female patient is instructed to attend the outpatient treatment center for several months with decreasing frequency [i.e., once a week for the first three months, once every two weeks during the second three months, and once a month during the third three months]. If feelings of anxiety return, she is scheduled to repeat at least one day, and up to three days, of flumazenil treatment.

XI. Example 5

Protocol for the Treatment of Post-Traumatic Stress Disorder (PTSD)/Acute Stress Disorder Developmental research is revealing that many brain and hormonal changes may occur as a result of early, prolonged trauma, and these changes contribute to difficulties with memory, learning, and regulating impulses and emotions. Combined with a disruptive, abusive home environment that does not foster healthy interaction, these brain and hormonal changes may contribute to severe behavioral difficulties (such as impulsivity, aggression, sexual acting out, eating disorders, alcohol/drug abuse, and self-destructive actions), emotional regulation difficulties (such as intense rage, depression, or panic), and mental difficulties (such as extremely scattered thoughts, dissociation, and amnesia). As adults, these individuals often are diagnosed with depressive disorders, personality disorders, or dissociative disorders. Treatment of acute stress disorder often takes much longer than with regular PTSD, may progress at a much slower rate, and requires a sensitive and structured treatment program delivered by a trauma specialist.

Psychiatric disorders that commonly co-occur with PTSD include depression, alcohol/substance abuse, panic disorder, and other anxiety disorders. Although crises that threaten the safety of the survivor or others must be addressed first, the best treatment results are achieved when both PTSD and the other disorder(s) are treated together rather than one after the other. This is especially true for PTSD and alcohol/substance abuse.

a. Pre-Treatment/Patient Assessment Phase

As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of Post-Traumatic Stress Disorder

The person has been exposed to a traumatic event in which both of the following were present:
  The person experienced, witnessed or was confronted with an event that involved actual or threatened death or serious injury, or a threat to the physical integrity of others AND
  The person's response involved intense fear, helplessness or horror. Note: In children, this may be expressed instead by disorganized or agitated behavior.
The traumatic event is persistently re-experienced in one (or more) of the following ways:
  Recurrent and intrusive distressing recollections of the event, including images, thoughts or perceptions. Note: In young children, repetitive play may occur in which themes or aspects of the trauma are expressed.
  Recurrent distressing dreams of the event. Note: In children, there may be frightening dreams without recognizable content.
  Acting or feeling as if the traumatic event were recurring (includes a sense of reliving the experience, illusions, hallucinations and dissociative flashback episodes, including those that occur on awakening or when intoxicated). Note: In young children, trauma-specific reenactment may occur.
  Intense psychological distress at exposure to internal or external cues that symbolize or resemble an aspect of the traumatic event.
  Physiological reactivity on exposure to internal or external cues that symbolize or resemble an aspect of the traumatic event.
Persistent avoidance of stimuli associated with the trauma and numbing of general responsiveness (not present before the trauma), as indicated by three (or more) of the following:
  Efforts to avoid thoughts, feelings or conversations associated with the trauma
  Efforts to avoid activities, places or people that arouse recollections of the trauma
  Inability to recall an important aspect of the trauma
  Markedly diminished interest or participation in significant activities
  Feeling of detachment or estrangement from others
  Restricted range of affect (eg, does not expect to have a career marriage, children or a normal life span)
Persistent symptoms of increased arousal (not present before the trauma) as indicated by two (or more) of the following:
  Difficulty falling or staying asleep
  Irritability or outbursts of anger
  Difficulty concentrating
  Hypervigilance
  Exaggerated startle response Duration of the disturbance (symptoms in Criteria B, C and D) is more than 1 month.
The disturbance causes clinically significant distress or impairment in social, occupational or other important areas of functioning.
Specify whether acute (the duration of the symptoms is less than 3 months), chronic (the duration of symptoms is 3 months or more), with delayed onset (if the onset of symptoms is at least 6 months after the stressor).

ii. Diagnosis of Acute Stress Disorder

The person has been exposed to a traumatic event in which both of the following were present:
  The person experienced, witnessed, or was confronted with an event or events that involved actual or threatened death or serious injury, or a threat the physical integrity of self or others
  The person's response involved intense fear, helplessness or horror
Either while experiencing or after experiencing the distressing event, the individual has three (or more) of the following dissociative symptoms:
  a subjective sense of numbing, detachment or absence of emotional responsiveness
  a reduction in awareness of his or her surroundings (eg, "being in a daze" derealization
  depersonalization
  dissociative amnesia (e.g., inability to recall an important aspect of the trauma)
The traumatic event is persistently re-experienced in at least one of the following ways: recurrent images, thought, dreams, illusions, flashback episodes or a sense of reliving the experience; or distress on exposure to reminders of the traumatic event.
Marked avoidance of the stimuli that arouse recollections of the trauma (e.g., thoughts, feelings, conversations, activities, places, people).
Marked symptoms of anxiety or increased arousal (e.g., difficulty sleeping, irritability, poor concentration, hypervigilance, exaggerated startle response, motor restlessness).
The disturbance causes clinically significant distress or impairment in social, occupational or other important areas of functioning or impairs the individual's ability to pursue some necessary task, such as obtaining necessary assistance or mobilizing personal resources by telling family members about the traumatic experience.
The disturbance lasts for a minimum of 2 days and a maximum of 4 weeks and occurs within 4 weeks of the traumatic event.
The disturbance is not due to the direct physiological effects of a substance (eg, a drug of abuse, a medication) or a general medical condition, is not better accounted for by brief psychotic disorder, and is not merely an exacerbation of a preexisting Axis I or Axis II disorder.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

The following treatment recommendations were adapted from the guidelines provided by the United States Department of Veterans Affairs, National Center for Post-Traumatic Stress Disorder. For more information, please refer to http://www.ncptsd.va.gov/facts/treatment/fs_treatment.html.

The treatment protocol includes psychological and pharmacological treatments. Pharmacotherapy (medication) can reduce the anxiety, depression, and insomnia often experienced with PTSD, and in some cases, it may help relieve the distress and emotional numbness caused by trauma memories. Several kinds of antidepressant drugs have contributed to patient improvement in most (but not all) clinical trials, although no particular drug has emerged as a definitive treatment for PTSD.

Currently, there are no FDA approved medications for acute stress reactions and the only FDA approved medication for PTSD is sertraline. It is also extremely important to consider possible drug interactions for individuals who are taking other prescribed or over-the-counter medications.

In some cases, a clinician may need to prescribe psychotropic medications even before he or she has completed the medical and psychiatric evaluation. The acute use of medications may be necessary when the survivor is dangerous, extremely agitated, or psychotic. In such circumstances, the individual should be taken to an emergency room. In the emergency room, short-acting benzodiazepines (e.g. lorazepam) or high potency neuroleptics (e.g. haldol) with minimal sedative, anticholinergic, and orthostatic side effects may prove effective. Atypical neuroleptics (e.g. risperidone), at relatively low doses, may also be useful in treating impulsive aggression. Pharmacological agents for the treatment of trauma-related arousal include benzodiazepines and antiadrenergic agents such as clonidine, guanfacine and propranolol.

Low doses of propranolol have also been successfully used to combat stage fright and performance anxiety because it modulates physical and cognitive manifestations of stress. However, clinicians should prescribe clonidine, guanfacine and propranolol judiciously for survivors with cardiovascular disease. This is because these medications may reduce blood pressure. In addition, clonidine may induce rebound hypertension if the client's blood levels fall due to infrequent dosing or a sudden discontinuation. Furthermore, these agents should not be prescribed to persons with diabetes as they may interfere with counterregulatory hormone responses to hypoglycemia.

Recent trauma survivors may also suffer from debilitating symptoms of depression. Since all three symptom clusters of PTSD respond to selective serotonin reuptake inhibitors (SSRIs), and because depressive symptoms originating soon after trauma may predict PTSD, it is recommended that SSRIs be considered for persistent posttraumatic depression. In addition, SSRIs may be useful for controlling anxiety and irritability. It is important to note that traumatized women, compared to men, may be particularly responsive to the beneficial effects of SSRIs. SSRIs as well as other antidepressants should be administered in a "start low and go slow" dosing regimen because some individuals may develop increased anxiety or agitation in response to them. In addition, individuals occasionally develop psychotic or manic symptoms in response to SSRIs.

Some individuals have preexisting psychiatric disorders, including preexisting PTSD, at the time that they experience trauma. The most recent trauma may exacerbate these preexisting conditions, making it essential to carefully assess the individual's psychotherapeutic and pharmacological needs. It is imperative that a clinician contact any other current treaters and maintain continuity of care.

ii. Placing a Patient in a state of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-inducing activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1

Male, 47 years old, under DSM-IV criteria, has been diagnosed as having post-traumatic stress disorder (PTSD).

Patient Preparation Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

g. Hypothetical Treatment Example 2

Male, 47 years old, under DSM IV criteria, has been diagnosed as having post-traumatic stress disorder (PTSD). He is currently undergoing cognitive-behavioral and pharmacotherapeutic treatment, current medication is paroxetine 20 mg/day.

Patient Preparation Step 1: Six weeks prior to scheduled treatment, patient is instructed to decrease paroxetine dosage 10 mg/day for two weeks.

Four weeks prior to scheduled treatment, patient is instructed to cease all medications, including alprazolam and paroxetine.

Patient Preparation Step 2: Four weeks prior to scheduled treatment, he is initiated on a scheduled finasteride administration of 5 mg per day. Three days prior to scheduled treatment, the finasteride administration is terminated and the patient is instructed to not engage in any stress-inducing activities or ingest any substances that would likely increase neurosteroid production.

Day 1 of Treatment: Male patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Male patient is administered flumazenil, via infusion, at a rate of at least 2.5 mg/day.

Day 3 of Treatment: Male patient is evaluated to determine if a third day of treatment is necessary. If he continues to report feelings of anxiety or cravings, he is again administered flumazenil, via infusion, at a rate of at least 2.5 mg/day.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Male patient is instructed to attend the outpatient treatment center for several months with decreasing frequency [i.e., once a week for the first three months, once every two weeks during the second three months, and once a month during the third three months]. If feelings of anxiety return, he is scheduled to repeat at least one day, and up to three days, of flumazenil treatment.

XII. Example 6

Protocol for the Treatment of Eating Disorders

Eating disorders, also considered psychological disorders, typically include elements of maladaptive eating patterns. Sufferers may experience withdrawal or withdrawal-like symptoms if they alter their diet suddenly. Anorexia nervosa, bulimia nervosa and other eating disorders, such as binge-eating, may be methods for artificially creating stress in one's system, thus increasing progesterone/allopregnanolone, thereby decreasing anxiety.

The primary physiological characteristics of anorexia nervosa are voluntary starvation and exercise stress. In addition to intentional starvation, subjects will also take part in a high level of physical activity. Anorexia nervosa also has a negative impact on the immune system and the central nervous system (CNS) and is also thought to be linked to serotonin and dopamine abnormalities.

The onset of anorexia may have a genetic component, with a certain gene linked to abnormalities with the neurotransmitter chemical serotonin. Such genetic characteristics might potentially equate to an easier path towards overly high serotonin levels, thus instilling heightened levels of anxiety and stress. Biologically, when a person is in a state of starvation, their levels of serotonin decrease, and thence increase again upon the consumption of food because of the tryptophan amino acids contained therein (tryptophan is used by the body to synthesize serotonin). It is thus hypothesized that the anorectic is conditioned into avoiding food to reduce his or her anxiety. Starvation is thus the stress-inducer, causing an increase in progesterone. Both eating and purging acutely induce stress to normalize anxiety.

Bulimia nervosa is a psychological condition in which the subject engages in recurrent binge eating followed by intentionally doing one or more of the following in order to compensate for the intake of food and prevent weight gain: vomiting; inappropriate use of laxatives, enemas, diuretics or other medication; excessive exercising; and fasting. Purging is a quicker method of increasing stress and thus progesterone. The compulsion to purge results in induced stress and normalized anxiety and thus, a greater feeling of control in the individual.

A person is characterized as bulimic when he or she feels incapable of controlling the urge to binge, even during the binge itself, when he or she consumes a larger amount of food that a person would normally consume at one sitting, and when such behavior occurs at least twice per week for three months. Bulimia is often less about food, and more about dealing with deep psychological issues and profound feelings of lack of control.

The following diagnosis and treatment guidelines are adapted from the National Collaborating Centre for Mental Health (Eating disorders. Core interventions in the treatment and management of anorexia nervosa, bulimia nervosa and related eating disorders. Leicester (UK): British Psychological Society; 2004. 260 p. [408 references]).

a. Pre-Treatment/Patient Assessment Phase

As described above, prior to admittance into the treatment program of the present invention, each patient should undergo a pre-treatment analysis. The pre-treatment analysis may be used to determine whether a patient is an optimal candidate for the treatment methodology of the present invention. In addition, the pre-treatment process may be administered to prepare a patient for admittance into the treatment methodology of the present invention.

i. Diagnosis of Eating Disorders

Assessment of people with eating disorders should be comprehensive and include physical, psychological, and social needs and a comprehensive assessment of risk to self. The level of risk to the patient's mental and physical health should be monitored as treatment progresses because it may change—for example, following weight gain or at times of transition between services in cases of anorexia nervosa.

Target groups for screening should include young women with low body mass index (BMI) compared with age norms, patients consulting with weight concerns who are not overweight, women with menstrual disturbances or amenorrhoea, patients with gastrointestinal symptoms, patients with physical signs of starvation or repeated vomiting, and children with poor growth.

When screening for eating disorders one or two simple questions should be considered for use with specific target groups (for example, "Do you think you have an eating problem?" and "Do you worry excessively about your weight?").

Young people with type 1 diabetes and poor treatment adherence should be screened and assessed for the presence of an eating disorder.

b. Preparing a Patient for Treatment with the Protocol of the Present Invention i. Additional Pre-Treatments If a patient is diagnosed and currently being treated with a conventional treatment for the anxiety disorder, the patient will need to be placed in a state of withdrawal, which includes, but is not limited to, weaning the patient off of any pharmacotherapy prescribed by the conventional treatment protocol. An exemplary protocol is described below, and thus, it should be noted that the invention is not limited to the use of such protocol.

1. Typical Anorexia Nervosa Treatment

There is a very limited evidence base for the pharmacological treatment of anorexia nervosa. A range of drugs may be used in the treatment of comorbid conditions but caution should be exercised in their use given the physical vulnerability of many people with anorexia nervosa.

Medication should not be used as the sole or primary treatment for anorexia nervosa. Caution should be exercised in the use of medication for comorbid conditions such as depressive or obsessive-compulsive features, as they may resolve with weight gain alone.

When medication is used to treat people with anorexia nervosa, the side effects of drug treatment (in particular, cardiac side effects) should be carefully considered because of the compromised cardiovascular function of many people with anorexia nervosa.

Health care professionals should be aware of the risk of drugs that prolong the QTc interval on the electrocardiogram (ECG) (for example, antipsychotics, tricyclic antidepressants, macrolide antibiotics, and some antihistamines). In patients with anorexia nervosa at risk of cardiac complications, the prescription of drugs with side effects that may compromise cardiac functioning should be avoided. If the prescription of medication that may compromise cardiac functioning is essential, ECG monitoring should be undertaken.

All patients with a diagnosis of anorexia nervosa should have an alert placed in their prescribing record concerning the risk of side effects.

In most patients with anorexia nervosa, an average weekly weight gain of 0.5-1 kg in inpatient settings and 0.5 kg in outpatient settings should be an aim of treatment. This requires about 3,500 to 7,000 extra calories a week.

Regular physical monitoring, and in some cases treatment with a multi-vitamin/multi-mineral supplement in oral form, is recommended for people with anorexia nervosa during both inpatient and outpatient weight restoration.

Total parenteral nutrition should not be used for people with anorexia nervosa, unless there is significant gastrointestinal dysfunction.

Pregnant women with either current or remitted anorexia nervosa may need more intensive prenatal care to ensure adequate prenatal nutrition and fetal development.

2. Typical Builimia Nervosa Treatment

As an alternative or additional first step to using an evidence-based self-help program, adults with bulimia nervosa may be offered a trial of an antidepressant drug.

Patients should be informed that antidepressant drugs can reduce the frequency of binge eating and purging, but the long-term effects are unknown. Any beneficial effects will be rapidly apparent.

Selective serotonin reuptake inhibitors (SSRIs) (specifically fluoxetine) are the drugs of first choice for the treatment of bulimia nervosa in terms of acceptability, tolerability, and reduction of symptoms. For people with bulimia nervosa, the effective dose of fluoxetine is higher than for depression (60 mg daily). No drugs, other than antidepressants, are recommended for the treatment of bulimia nervosa.

3. Typical Treatment of Binge Eating Disorder

As an alternative or additional first step to using an evidence based self-help programme, consideration should be given to offering a trial of an SSRI antidepressant drug to patients with binge eating disorder.

Patients with binge eating disorders should be informed that SSRIs can reduce binge eating, but the long-term effects are unknown. Antidepressant drug treatment may be sufficient treatment for a limited subset of patients.

ii. Placing a Patient in a State of Withdrawal

A patient may be placed in a state of withdrawal by actively inhibiting the upregulation of endogenous neurosteroids and/or causing the downregulation of endogenous neurosteroids. As previously described, this treatment step may be achieved by a) avoiding stress-inducing activities, b) avoiding neurosteroid production enhancing activities, c) avoiding heightened progesterone levels in a patient, d) actively modulating a woman's progesterone levels, or e) actively modulating a male's or female's progesterone levels through the administration of a neurosteroid inhibitor.

c. Administration of a Compound from the Class of Compounds that Modulates $GABA_A$ Receptor Expression Once the pre-treatment protocol has been adhered to and completed, a patient is administered a compound from the class of compounds that modulates $GABA_A$ receptor expression, such as flumazenil, as described above in the general treatment methodology.

d. Additional Treatment Options

Once the treatment protocol has been administered, additional treatment options may be administered, as described above in the general treatment methodology.

e. Post-Treatment Phase of Protocol

Once the treatment protocol has been administered, a post-treatment protocol is administered, as described above in the general treatment methodology.

f. Hypothetical Treatment Example 1 Anorexia, Bulimia, or Binge Eating Disorder

Female, 26, under DSM-IV criteria, has been diagnosed as having an eating disorder, and more specifically, anorectic and bulimic episodes.

Patient Preparation: In one embodiment, six weeks prior to scheduled treatment, female patient is administered oral contraceptives. One week prior to scheduled treatment, the administration of oral contraceptives is terminated. Three days prior to scheduled treatment, the patient is instructed to not engage in any stress-inducing activities or ingest any substances that would likely increase neurosteroid production.

In another embodiment, treatment protocol of the present invention is begun when progesterone levels are low in a female patient. Preferably, this time window begins on the day of menstruation and lasts for about ten days. The ideal time window of minimal progesterone levels has been described in detail above. The responsible treating physician should examine each patient individually and determine, using proper diagnostic tests and patient history, when the optimal low progesterone time window is for that particular patient. Thus, the protocol outlined herein is exemplary.

Day 1 of Treatment: Female patient is administered flumazenil, via infusion, at an amount less than 15 mg/day. The patient's heart rate and blood pressure are monitored, along with the patient's own qualitative assessment of his health, including, but not limited to, subjective feelings of anxiety. The total dose and rate are modified by the responsible physician based on an evaluation of the patient's heart rate, blood pressure, and subjective reports.

Day 2 of Treatment: Female patient is administered flumazenil, via infusion, at a rate of at least 2.5 mg/day.

Day 3 of Treatment: Female patient is evaluated to determine if a third day of treatment is necessary. If she continues to report feelings of anxiety or cravings, she is again administered flumazenil, via infusion, at a rate of at least 2.5 mg/day. Patient is then instructed to return to treatment center in 28 days. Again, the treating physician should ensure that the patient is in a minimal progesterone time window.

Day 28+1 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Day 28+2 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Female patient is instructed to attend the outpatient treatment center for several months with decreasing frequency [i.e., once a week for the first three months, once every two weeks during the second three months, and once a month during the third three months]. If feelings of anxiety return, she is scheduled to repeat at least one day, and up to three days, of flumazenil treatment.

g. Hypothetical Treatment Example 2—Bulimia Nervosa

Female, 26, under DSM-IV criteria, has been diagnosed as having an eating disorder, and more specifically, bulimic episodes. She is currently under treatment and taking 60 mg/day fluoxetine hydrochloride, administered in the morning.

Patient Preparation Sixteen weeks prior to scheduled treatment, patient is advised to reduce the dosage of fluoxetine to 30 mg/day for four weeks. Twelve weeks prior to scheduled treatment, the dosage is further lowered to 10 mg/day for four weeks. Eight weeks prior to scheduled treatment, patient is advised to stop taking all medications, including fluoxetine.

Additional Patient Preparation: In one embodiment, six weeks prior to scheduled treatment, female patient is administered oral contraceptives. One week prior to scheduled treatment, the administration of oral contraceptives is terminated. Three days prior to scheduled treatment, the patient is instructed to not engage in any stress-inducing activities or ingest any substances that would likely increase neurosteroid production.

In another embodiment, treatment protocol of the present invention is begun when progesterone levels are low in a female patient. Preferably, this time window begins on the day of menstruation and lasts for about ten days. The ideal time window of minimal progesterone levels has been described in detail above. The responsible treating physician should examine each patient individually and determine, using proper diagnostic tests and patient history, when the optimal low progesterone time window is for that particular patient. Thus, the protocol outlined herein is exemplary.

Day 1 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Day 2 of Treatment: Female patient is administered flumazenil, via infusion, at a rate of at least 2.5 mg/day.

Day 3 of Treatment: Female patient is evaluated to determine if a third day of treatment is necessary. If she continues to report feelings of anxiety or cravings, she is again administered flumazenil, via infusion, at a rate of at least 2.5 mg/day. Patient is then instructed to return to treatment center in 28 days. Again, the treating physician should ensure that the patient is in a minimal progesterone time window.

Day 28+1 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Day 28+2 of Treatment: Female patient is administered flumazenil, via infusion, at an amount less than 15 mg/day. The patient's heart rate and blood pressure are monitored, along with the patient's own qualitative assessment of her health, including, but not limited to, subjective feelings of anxiety. The total dose and rate are modified by the responsible physician based on an evaluation of the patient's heart rate, blood pressure, and subjective reports.

Post-Treatment: Post-completion of treatment phase, patient is prescribed a post-treatment regimen to follow, which includes, but is not limited to, the administration of pharmaceutical compositions, outpatient therapy, a diet program, and an exercise regimen. Female patient is instructed to attend the outpatient treatment center for several months with decreasing frequency [i.e., once a week for the first three months, once every two weeks during the second three months, and once a month during the third three months]. If feelings of anxiety return, she is scheduled to repeat at least one day, and up to three days, of flumazenil treatment.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims. All patents, publications and abstracts cited above are incorporated herein by reference in their entirety.

TABLE 1

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
| --- | --- | --- | --- |
| ANALGESICS (PAINKILLERS) | OPIATES | ALFENTANIL ALFENTA (alfentanil hydrochloride) | FOR USE DURING GENERAL ANESTHESIA SPONTANEOUSLY BREATHING/ASSISTED VENTILATION: Induction of Analgesia: 8-20 mcg/kg; Maintenance of Analgesia: 3-5 mcg/kg q 5-20 min or 0.5 to 1 mcg/kg/min; Total dose: 8-40 mcg/kg ASSISTED OR CONTROLLED VENTILATION: |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | Incremental Injection (to attenuate response to laryngoscopy and intubation): Induction of Analgesia: 20-50 mcg/kg; Maintenance of Analgesia: 5-15 mcg/kg q 5-20 min; Total dose: Up to 75 mcg/kg. Continuous Infusion: (To provide attenuation of response to intubation and incision): Infusion rates are variable and should be treated to the desired clinical effect. Induction of Analgesia: 50-75 mcg/kg; Maintenance of Analgesia: 0.5 to 3 mcg/kg/min (Average rate 1 to 1.5 mg/kg/min); Total dose: Dependent on duration of procedure. Anesthetic Induction: Induction of Analgesia: 130-245 mcg/kg; Maintenance of Analgesia: 0.5 to 1.5 mcg/kg/min or general anesthetic; Total dose: Dependent on duration of procedure. At these doses, truncal rigidity should be expected and a muscle relaxant should be utilized; Administer slowly (over 3 minutes); Concentration of inhalation agents reduced by 30-50% for initial hour. MONITORED ANESTHESIA CARE (MAC) (For sedated and responsive, spontaneously breathing patients): Induction of M.C. 3-8 mcg/kg; Maintenance of M.C. 3-5 mcg/kg q 5-20 min or 0.25 to 1 mcg/kg/min; Total dose: 3-40 mcg/kg |
| | | BUPRENORPHINE | Administered sublingually as a single daily dose in the range of 12 to 16 mg/day. Buprenorphine is also delivered transdermally in 25, 50, and 75 mcg/hour. |
| | | BUTORPHANOL | This formulation of butorphanol is administered every 3-4 hours either as a nasal spray or injected into the buttock or hip muscle or into a vein. The FDA does not regulate Stadol ® in most states. |
| | | CODEINE (also METHYL MORPHINE) | Codeine and codeine-combo preparations are usually taken every 4-6 hours. Adults: 15 to 60 mg every 4 to 6 hours (usual adult dose, 30 mg). Children: 1 Year of Age and Older - 0.5 mg/kg of b.d. weight or 15 mg/m2 of b.d. surface every 4 to 6 hours. 200 mg (oral) of codeine is about equal to 30 mg (oral) of morphine. |
| | | CODEINON See Hydrocodone for details. | |
| | | PROPOXYPHENE (DARVOCET) | Acetaminophen (Tylenol) and propoxyphene. It is formulated as a tablet taken every 4 hours by mouth. |
| | | DEXTROPROPOXYPHENE | Oral analgesic potency is one-half to one-third that of codeine, with 65 mg approximately equivalent to about 600 mg of aspirin. Dextropropoxyphene is prescribed for relief of mild to moderate pain. |
| | | HEROIN (DIACETYLMORPHINE) | ILLICIT SUBSTANCE/NO APPROVED DOSING |
| | | DIHYDROCODEINE | Dihydrocodeine is approximately twice as potent as codeine; this is taken into consideration while dosing dihydrocodeine. Codeine Dosage: For the treatment of mild pain to moderate pain: Adults: 15-60 mg PO (oral) every 4-6 hours. For the treatment of non-productive cough: Adults: 10-20 mg PO (oral) every 4-6 hours. For the treatment of diarrhoea: Adults: 30 mg PO (oral) |
| | | FENTANYL | Route of administration: patch, injected, oral transmucosal. The patch is usually changed every 72 hours or as directed by physician. Fentanyl (DURAGESIC ®) should ONLY be used in patients who are already receiving opioid therapy, who have demonstrated opioid tolerance, and who require a total daily dose at least equivalent to DURAGESIC ® 25 mcg/h. Patients who are considered opioid-tolerant are those who have been taking, for a week or longer, at least 60 mg of morphine daily, or at least 30 mg of oral oxycodone daily, or at least 8 mg oral hydromorphone daily, or an equianalgesic dose of another opioid. |
| | | HYDROCODONE DIHYDROCODEINONE | Five mg of hydrocodone is equivalent to 30 mg of codeine when administered orally. Also, a dose of 15 mg (¼ gr) of hydrocodone is equivalent to 10 mg (⅙ gr) of morphine. The typical therapeutic dose of 5 to 10 mg is pharmacologically equivalent to 30 to 60 mg of oral codeine. |
| | | HYDROMORPHONE | Dilaudid ® is formulated as oral tablets and liquid, rectal suppository, intra-muscular (buttock or hip muscle) injection, and intravenous (I.V.) solution. Dosing is every 4-6 hours for the oral forms and every 6-8 hours for the suppository. An I.V. drip allows for continuous administration and around-the-clock pain relief. It can be given intravenously, intramuscularly, rectally, or orally. |
| | | LAAM Levomethadyl Acetate Hydrochloride, also known as Levo-alpha-acetylmethadol or Levacetylmethadol (LAM) | The initial dose street addicts should be 20 to 40 mg. Each subsequent dose, administered at 48- or 72-hour intervals, may be adjusted in increments of 5 to 10 mg until a pharmacokinetic and pharmacodynamic steady-state is reached. Patients dependent on methadone may require higher initial doses. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | METHADONE | It comes as tablets, dispersible tablets, liquid, and liquid concentrate. Patients take it every 3-4 hours for severe pain and every 6-8 hours for chronic pain. |
| | | MORPHINE and MORPHINONE | NO APPROVED DOSING FOR PURE MORPHINE. SEE SALTS. |
| | | MORPHINE SULFATE | MS Contin ® comes in the form of tablets, capsules, liquid, and rectal suppository, which are taken every 4 hours. Long-acting tablets and capsules can be taken every 8-12 hours or 1-2 per day, respectively. |
| | | OPIUM (NATURAL) | ILLEGAL - NO FDA RECOMMENDED USAGE |
| | | OXYCODONE | OxyContin ® comes in liquid and tablet forms taken every 6 hours. Long-acting tablets are available to take every 12 hours. |
| | | OXYMORPHONE | Injection: Subcutaneous or intramuscular administration: initially 1 mg to 1.5 mg, repeated every 4 to 6 hours as needed. Intravenous: 0.5 mg initially. For analgesia during labor 0.5 mg to 1 mg intramuscularly is recommended. Rectal Suppositories: One suppository, 5 mg, every 4 to 6 hours. |
| | | PETHIDINE (MEPERIDINE) | Adults: The usual dosage is 50 mg to 150 mg intramuscularly, subcutaneously, or orally, every 3 or 4 hours as necessary. Children: The usual dosage is 0.5 mg/lb to 0.8 mg/lb intramuscularly, subcutaneously, or orally up to the adult dose, every 3 or 4 hours as necessary. |
| | | REMIFENTANIL | During Induction of Anesthesia: ULTIVA should be administered at an infusion rate of 0.5 to 1 mcg/kg/min with a hypnotic or volatile agent for the induction of anesthesia. If endotracheal intubation is to occur less than 8 minutes after the start of the infusion of ULTIVA, then an initial dose of 1 mcg/kg may be administered over 30 to 60 seconds. For exact dosing for induction, maintenance and continuation of general anesthesia, including special cases, please refer to FDA Documents. |
| | | SUFENTANIL | Not more than 3 total doses. Each dose must be at least one hour apart. |
| | | THEBAINE | Thebaine is not used therapeutically, but is converted into a variety of compounds including codeine, hydrocodone, hydromorphone, oxycodone, oxymorphone, nalbuphine, naloxone, naltrexone, buprenorphine and etorphine. It is controlled in Schedule II of the Controlled Substances Act as well as under international law. |
| | | TRAMADOL | Tramadol is approximately 10% as potent as morphine, when given by the IV/IM route. Oral doses range from 50-400 mg daily, with up to 600 mg daily when given IV/IM. |
| | TETRAHYRDOC ANNIBINOL/ THC THC and some other cannibinoids, have analgesic properties. | MARINOL | Marinol: widely available through prescription. It comes in the form of a pill and is also being studied by researchers for suitability via other delivery methods, such as an inhaler or patch. The active ingredient of Marinol is synthetic THC, which has been found to relieve the nausea and vomiting associated with chemotherapy and the loss of appetite associated with various other disease states. |
| | | THC - Herbal and Synthetic | ILLICIT SUBSTANCE - NO FDA-APPROVED DOSAGE |
| | | KETAMINE | Intravenous Route: The initial dose of ketamine administered intravenously may range from 1 mg/kg to 4.5 mg/kg (0.5 to 2 mg/lb). The average amount required to produce five to ten minutes of surgical anesthesia has been 2 mg/kg (1 mg/lb). Intramuscular Route: The initial dose of ketamine administered intramuscularly may range from 6.5 to 13 mg/kg (3 to 6 mg/lb). A dose of 10 mg/kg (5 mg/lb) will usually produce 12 to 25 minutes of surgical anesthesia. |
| BARBITURATES | | ALLOBARBITAL | MRTD (Maximum Recommended Therapeutic Dose) - 3.33000 mg/kg-body weight (bw)/day based upon an average adult weighing 60 kg. |
| | | AMOBARBITAL | Defined Daily Dose - 0.1 g, No data available from FDA. |
| | | APROBARBITAL | MRTD (Maximum Recommended Therapeutic Dose) - 2.67000 mg/kg-body weight (bw)/day based upon an average adult weighing 60 kg. For trouble in sleeping: Adults-40 to 160 milligrams (mg) at bedtime. For daytime sedation: Adults-40 mg three times a day. |
| | | BARBEXACLONE | 100 mg of barbexaclone is equivalent to 60 mg of phenobarbital. |
| | | BARBITAL (VERONAL) | MRTD (Maximum Recommended Therapeutic Dose) in mg/kg-body weight (bw)/day based upon an average adult weighing 60 kg- 10.00000 |
| | | BUTABARBITAL | Butabarbital Oral is used to treat the following: Severe Anxiety, Additional Agent to Induce General Anesthesia, Abnormal Trouble Sleeping |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | MRTD (Maximum Recommended Therapeutic Dose) in mg/kg-body weight (bw)/day based upon an average adult weighing 60 kg - 2.000 |
| | | BUTALBITAL Butalbital, 5-allyl-5-isobutylbarbituric acid. | MRTD (Maximum Recommended Therapeutic Dose) in mg/kg-body weight (bw)/day based upon an average adult weighing 60 kg - 5.000 COMMON COMBINATIONS INCLUDE: Butalbital and acetaminophen butalbital, acetaminophen, and caffeine butalbital and aspirin butalbital, aspirin, and caffeine |
| | | BUTOBARBITAL (SONERYL) | 50 mg of Butobarbital is equivalent to 10 mg of Diazepam; Acc. to Nordic Statistics on Medicines, the Defined Daily Dose of Butobarbital is 150 mg. No data available from FDA. |
| | | CYCLOBARBITAL | MRTD (Maximum Recommended Therapeutic Dose) in mg/kg-body weight (bw)/day based upon an average adult weighing 60 kg - 6.67000 |
| | | ETHALLOBARBITAL | N.A. |
| | | HEPTABARBITAL | Defined Daily Dose - 0.2 g, No data available from FDA. |
| | | HEXOBARBITAL | MRTD (Maximum Recommended Therapeutic Dose) in mg/kg-body weight (bw)/day based upon an average adult weighing 60 kg - 8.33000 |
| | | MEPHOBARBITAL (METHYLPHENOBARBITAL) | Epilepsy: Average dose for adults: 400 mg to 600 mg daily; children under 5 years: 16 mg to 32 mg three or four times daily; children over 5 years: 32 mg to 64 mg three or four times daily. Sedation: Adults: 32 mg to 100 mg optimum dose, 50 mg three to four times daily. Children: 16 mg to 32 mg three to four times daily. |
| | | METHARBITAL | |
| | | METHOHEXITAL | For induction of anesthesia, a 1% solution is administered at a rate of about 1 mL/5 seconds. The dose required for induction may range from 50 to 120 mg or more but averages about 70 mg. The usual dosage in adults ranges from 1 to 1.5 mg/kg. Maintenance of anesthesia may be accomplished by intermittent injections of the 1% solution or, more easily, by continuous intravenous drip of a 0.2% solution. Intermittent injections of about 20 to 40 mg (2 to 4 mL of a 1% solution) may be given as required, usually every 4 to 7 minutes. For continuous drip, the average rate of administration is about 3 mL of a 0.2% solution/minute (1 drop/second). |
| | | PENTOBARBITAL | The usual adult dosage of NEMBUTAL Sodium Solution is 150 to 200 mg as a single IM injection; the recommended pediatric dosage ranges from 2 to 6 mg/kg as a single IM injection not to exceed 100 mg. The rate of IV injection should not exceed 50 mg/min for pentobarbital sodium. |
| | | PHENOBARBITAL | Pediatric Oral Dosage (as recommended by the American Academy of Pediatrics): Preoperative: 1 to 3 mg/kg. Adult Oral Dosage: Daytime sedative: 30 to 120 mg daily in 2 to 3 divided doses. Bedtime hypnotic: 100 to 320 mg. Anticonvulsant: 50 to 100 mg 2 to 3 times daily. |
| | | PRIMIDONE | Adult Dosage: Patients 8 years of age and older who have received no previous treatment may be started on primidone according to the following regimen using Primidone 250 mg tablets. Days 1-3: 100 to 125 mg at bedtime; Days 4-6: 100 to 125 mg b.i.d.; Days 7-9: 100 to 125 mg t.i.d.; Day 10-maintenance; 250 mg t.i.d. For most adults and children 8 years of age and over, the usual maintenance dosage is three to four 250 mg primidone tablets daily in divided doses (250 mg t.i.d. or q.i.d.). If required, an increase to five or six 250 mg tablets daily may be made but daily doses should not exceed 500 mg q.i.d. Pediatric Dosage: For children under 8 years of age, the following regimen may be used: Days 1-3: 50 mg at bedtime; Days 4-6: 50 mg b.i.d.; Days 7-9: 100 mg b.i.d.; Day 10-maintenance: 125. mg t.i.d. to 250 mg t.i.d. For children under 8 years of age, the usual maintenance dosage is 125 to 250 mg three times daily, or 10-25 mg/kg/day in divided doses. |
| | | SECOBARBITAL | For oral dosage form (capsules): For trouble in sleeping: Adults-100 milligrams (mg) at bedtime. Children-Dose must be determined by your doctor. For daytime sedation: Adults-30 to 50 mg three or four times a day. Children-Dose is based on body weight or size and must be determined by your doctor. The usual dose is 2 mg per kilogram (kg) (0.9 mg per pound) of body weight three times a day. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | For sedation before surgery: Adults-200 to 300 mg one or two hours before surgery. Children-Dose is based on body weight and must be determined by your doctor. The usual dose is 2 to 6 mg per kg (0.9 to 2.7 mg per pound) of body weight one or two hours before surgery. However, the dose is usually not more than 100 mg. For injection dosage form: For trouble in sleeping: Adults-100 to 200 mg injected into a muscle, or 50 to 250 mg injected into a vein. Children-Dose is based on body weight or size and must be determined by your doctor. The usual dose is 3 to 5 mg per kg (1.4 to 2.3 mg per pound) of body weight, injected into a muscle. However, the dose is usually not more than 100 mg. For sedation before dental procedures: Adults-Dose is based on body weight and must be determined by your doctor. The usual dose is 1.1 to 2.2 mg per kg (0.5 to 1 mg per pound) of body weight, injected into a muscle ten to fifteen minutes before the procedure. Children-Dose must be determined by your dentist. For sedation before a nerve block: Adults-100 to 150 mg, injected into a vein. For sedation before surgery: Children-Dose is based on body weight and must be determined by your doctor. The usual dose is 4 to 5 mg per kg (1.8 to 2.3 mg per pound) of body weight, injected into a muscle. |
| | | TALBUTAL (Lotusate ®), also called 5-allyl-5-sec-butylbarbituric acid. | MRTD (Maximum Recommended Therapeutic Dose) in mg/kg-body weight (bw)/day based upon an average adult weighing 60 kg - 3.30000 |
| | | THIOBARBITAL | N.A. |
| | | THIOPENTAL Pentothal (Thiopental Sodium for Injection, USP). | Use in Anesthesia: Moderately slow induction can usually be accomplished in the "average" adult by injection of 50 to 75 mg (2 to 3 mL of a 2.5% solution) at intervals of 20 to 40 seconds, depending on the reaction of the patient. Once anesthesia is established, additional injections of 25 to 50 mg can be given whenever the patient moves. Use in Convulsive States: For the control of convulsive states following anesthesia (inhalation or local) or other causes, 75 to 125 mg (3 to 5 mL of a 2.5% solution) should be given as soon as possible after the convulsion begins. Convulsions following the use of a local anesthetic may require 125 to 250 mg of Pentothal given over a ten minute period. Use in Psychiatric Disorders: For narcoanalysis and narcosynthesis in psychiatric disorders, premedication with an anticholinergic agent may precede administration of Pentothal. After a test dose, Pentothal (Thiopental Sodium for Injection, USP) is injected at a slow rate of 100 mg/mm (4 mL/min of a 2.5% solution) with the patient counting backwards from 100. Shortly after counting becomes confused but before actual sleep is produced, the injection is discontinued. Allow the patient to return to a semidrowsy state where conversation is coherent. Alternatively, Pentothal may be administered by rapid I.V. drip using a 0.2% concentration in 5% dextrose and water. At this concentration, the rate of administration should not exceed 50 mL/min. |
| | | VINBARBITAL Vinbarbital (5-Ethyl-5-(1-methyl-1-butenyl)barbituric acid). | MRTD (Maximum Recommended Therapeutic Dose) in mg/kg-body weight (bw)/day based upon an average adult weighing 60 kg - 3.33000 |
| | | VINYLBITAL Butylvinyl | Defined Daily Dose - 0.15 g, No data available from FDA. |
| BENZODIAZEPINES | | ALPRAZOLAM | Dosage Depends on Disorder: Oral (For anxiety or nervous tension): Start: 0.25 mg to 0.5 mg 3 times daily. Maximum: 4 mg in 24 hours. Oral (For panic disorder): Start: 0.5 mg 3 times daily. Increases: 1 mg daily in 3 to 4 day intervals. Maximum: 10 mg in 24 hours. |
| | | BROMAZEPAM | Not commercially available in the U.S. |
| | | BROTIZOLAM | Brotizolam is not approved for sale in the United States or Canada. |
| | | CAMAZEPAM | Defined Daily Dose - 30 mg, No data available from FDA. |
| | | CHLORDIAZEPOXIDE | For relief of mild and moderate anxiety disorders and symptoms of anxiety: 5 mg or 10 mg, 3 or 4 times daily. For relief of server anxiety disorders and symptoms of anxiety: 20 mg or 25 mg, 3 or 4 times daily. Geriatric patients or in the presence of debilitating disease: 5 mg, 2 to 4 times daily. |
| | | CLONAZEPAM | Seizure Disorders: Adults: The initial dose for adults with seizure disorders should not exceed 1.5 mg/day divided into three doses. Dosage may be increased in increments of 0.5 to 1 mg every 3 days until seizures are adequately controlled or until side effects preclude any further increase. Maintenance dosage must be individualized for each patient depending upon response. Maximum recommended |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | daily dose is 20 mg.<br>Pediatric Patients: Klonopin is administered orally. In order to minimize drowsiness, the initial dose for infants and children (up to 10 years of age or 30 kg of body weight) should be between 0.01 and 0.03 mg/kg/day but not to exceed 0.05 mg/kg/day given in two or three divided doses. Dosage should be increased by no more than 0.25 to 0.5 mg every third day until a daily maintenance dose of 0.1 to 0.2 mg/kg of body weight has been reached, unless seizures are controlled or side effects preclude further increase. Whenever possible, the daily dose should be divided into three equal doses. If doses are not equally divided, the largest dose should be given before retiring.<br>Panic Disorder: Adults: The initial dose for adults with panic disorder is 0.25 mg bid. An increase to the target dose for most patients of 1 mg/day may be made after 3 days. The recommended dose of 1 mg/day is based on the results from a fixed dose study in which the optimal effect was seen at 1 mg/day. Higher doses of 2, 3 and 4 mg/day in that study were less effective than the 1 mg/day dose and were associated with more adverse effects. Nevertheless, it is possible that some individual patients may benefit from doses of up to a maximum dose of 4 mg/day, and in those instances, the dose may be increased in increments of 0.125 to 0.25 mg bid every 3 days until panic disorder is controlled or until side effects make further increases undesired. To reduce the inconvenience of somnolence, administration of one dose at bedtime may be desirable.<br>Treatment should be discontinued gradually, with a decrease of 0.125 mg bid every 3 days, until the drug is completely withdrawn. |
| | | CLOTIAZEPAM | Clotiazepam is not approved for sale in the United States or Canada |
| | | CLORAZEPATE | ORAL:<br>START: 15 mg/daily<br>INCREASES: As needed.<br>MAXIMUM: 60 mg in 24 hours |
| | | CLOXAZOLAM | Cloxazolam is not approved for sale in the United States or Canada. |
| | | DELORAZEPAM | Defined Daily Dose - 3 mg, No data available from FDA. |
| | | DIAZEPAM | Management of Anxiety Disorders and Relief of Symptoms of Anxiety: Depending upon severity of symptoms - 2 mg to 10 mg, 2 to 4 times daily.<br>Symptomatic Relief in Acute Alcohol Withdrawal: 10 mg, 3 or 4 times during the first 24 hours, reducing to 5 mg, 3 or 4 times daily as needed.<br>Adjunctively for Relief of Skeletal Muscle Spasm: 2 mg to 10 mg, 3 or 4 times daily.<br>Adjunctively in Convulsive Disorders. 2 mg to 10 mg, 2 to 4 times daily.<br>Geriatric Patients, or in the presence of debilitating disease: 2 mg to 2.5 mg, 1 or 2 times daily initially; increase gradually as needed and tolerated.<br>Pediatric patients: Because of varied responses to CNS-acting drugs, initiate therapy with lowest dose and increase as required. Not for use in pediatric patients under 6 months. 1 mg to 2.5 mg, 3 or 4 times daily initially; increase gradually as needed and tolerated. |
| | | ESTAZOLAM | The recommended initial dose for adults is 1 mg at bedtime; however, some patients may need a 2 mg dose. In healthy elderly patients, 1 mg is also the appropriate starting dose, but increases should be initiated with particular care. In small or debilitated older patients, a starting dose of 0.5 mg, while only marginally effective in the overall elderly population, should be considered. |
| | | ETIZOLAM | Etizolam is not approved for sale in the United States or Canada. |
| | | FLUDIAZEPAM | Defined Daily Dose - 0.75 mg, No data available from FDA. |
| | | FLUNITRAZEPAM | Flunitrazepam has not been approved by the Food and Drug Administration for medical use in the United States. It is available only by private prescription in the United Kingdom |
| | | FLURAZEPAM | Dosage should be individualized for maximal beneficial effects. The usual adult dosage is 30 mg before retiring. In some patients, 15 mg may suffice. In elderly and/or debilitated patients, 15 mg is usually sufficient for a therapeutic response |
| | | HALAZEPAM | For oral dosage form (tablets):<br>For anxiety: Adults-20 to 40 milligrams (mg) three or four times a day. Children younger than 18 years of age-Use and dose must be determined by your doctor.<br>Older adults-20 mg one or two times a day. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | HALOXAZOLAM | Defined Daily Dose - 7.50 mg, No data available from FDA. |
| | | LOPRAZOLAM | It is available in 1 mg tablets.<br>The usual adult dose is 1-2 mg at bedtime, the higher dose being recommended for patients who have previously been treated with benzodiazepines for severe persistent insomnia. An initial dose of 0.5 mg-1.0 mg is recommended in elderly and debilitated patients. |
| | | LOREZEPAM | The usual range is 2 to 6 mg/day given in divided doses, the largest dose being taken before bedtime, but the daily dosage may vary from 1 to 10 mg/day.<br>For anxiety, most patients require an initial dose of 2 to 3 mg/day given b.i.d. or t.i.d.<br>For insomnia due to anxiety or transient situational stress, a single daily dose of 2 to 4 mg may be given, usually at bedtime.<br>For elderly or debilitated patients, an initial dosage of 1 to 2 mg/day in divided doses is recommended, to be adjusted as needed and tolerated. |
| | | MEDAZEPAM | Defined daily dose as used in the Nordic Statistics on Medicines - 20 mg; No data available from FDA. |
| | | MIDAZOLAM | For preoperative sedation/anxiolysis/amnesia.<br>Intramuscular - The recommended premedication dose of VERSED for good risk (ASA Physical Status I & II) adult patients below the age of 60 years is 0.07 to 0.08 mg/kg IM (approximately 5 mg IM) administered up to 1 hour before surgery.<br>The dose must be individualized and reduced when IM VERSED is administered to patients with chronic obstructive pulmonary disease, other higher risk surgical patients, patients 60 or more years of age, and patients who have received concomitant narcotics or other CNS depressants. In a study of patients 60 years or older, who did not receive concomitant administration of narcotics, 2 to 3 mg (0.02 to 0.05 mg/kg) of VERSED produced adequate sedation during the preoperative period. The dose of 1 mg IM VERSED may suffice for some older patients if the anticipated intensity and duration of sedation is less critical.<br>Intravenous - VERSED 1 mg/mL formulation is recommended for sedation/anxiolysis/amnesia for procedures to facilitate slower injection. Both the 1 mg/mL and the 5 mg/mL formulations may be diluted with 0.9% sodium chloride or 5% dextrose in water. 1. Healthy Adults Below the Age of 60: Titrate slowly to the desired effect (eg, the initiation of slurred speech). Some patients may respond to as little as 1 mg. No more than 2.5 mg should be given over a period of at least 2 minutes. A total dose greater than 5 mg is not usually necessary to reach the desired endpoint.<br>If narcotic premedication or other CNS depressants are used, patients will require approximately 30% less VERSED than unpremedicated patients.<br>2. Patients Age 60 or Older, and Debilitated or Chronically Ill Patients: Titrate slowly to the desired effect (eg, the initiation of slurred speech). Some patients may respond to as little as 1 mg. No more than 1.5 mg should be given over a period of no less than 2 minutes. If additional titration is necessary, it should be given at a rate of no more than 1 mg over a period of 2 minutes, waiting an additional 2 or more minutes each time to fully evaluate the sedative effect. Total doses greater than 3.5 mg are not usually necessary.<br>Epileptic fit: 10 mg intranasally or as buccal. |
| | | NIMETAZEPAN | MRTD (Maximum Recommended Therapeutic Dose) in mg/kg-body weight (bw)/day based upon an average adult weighing 60 kg 0.08330 |
| | | NITRAZEPAM | Nitrazepam shortens the time required to fall asleep and lengthens the duration of this sleep. Typically, it may work within an hour and allow the individual to maintain sleep for 4 to 6 hours. It is no longer available in the United States. |
| | | NORDAZEPAM | Defined Daily Dose - 15 mg, No data available from FDA. |
| | | OXAZEPAM | Mild to moderate anxiety, with associated tension, irritability, agitation or related symptoms of functional origin or secondary to organic disease: 10 to 15 mg, 3 or 4 times daily.<br>Severe anxiety syndromes, agitation, or anxiety associated with depression: 15 to 30 mg, 3 or 4 times daily.<br>Older patients with anxiety, tension, irritability, and agitation: Initial dosage - 10 mg, 3 times daily. If necessary, increase cautiously to 15 mg, 3 or 4 times daily.<br>Alcoholics with acute inebriation, tremulousness, or anxiety on withdrawal: 15 to 30 mg, 3 or 4 times daily. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | OXAZOLAM | 20 mg is equivalent to 10 mg of Diazepam. MRTD (Maximum Recommended Therapeutic Dose) in mg/kg-body weight (bw)/day based upon an average adult weighing 60 kg 1.0000 |
| | | PINAZEPAM | MRTD (Maximum Recommended Therapeutic Dose) in mg/kg-body weight (bw)/day based upon an average adult weighing 60 kg 0.33300 |
| | | PRAZEPAM | MRTD (Maximum Recommended Therapeutic Dose) in mg/kg-body weight (bw)/day based upon an average adult weighing 60 kg 1.00000 |
| | | QUAZEPAM | The recommended initial dose is 15 milligrams daily. Your doctor may later reduce this dosage to 7.5 milligrams. |
| | | TEMAZEPAM | While the recommended usual adult dose is 15 mg before retiring, 7.5 mg may be sufficient for some patients, and others may need 30 mg. In transient insomnia, a 7.5 mg dose may be sufficient to improve sleep latency. In elderly and/or debilitated patients it is recommended that therapy be initiated with 7.5 mg until individual responses are determined. |
| | | TETRAZEPAM | Defined Daily Dose - 100 mg, No data available from FDA. |
| | | TOFISOPAM | Tofisopam is not approved for sale in the US or Canada. However, Vela Pharmaceuticals of New Jersey is developing the D-enantiomer (dextofisopam) as a treatment for IBS. |
| | | TRIAZOLAM | The recommended dose for most adults is 0.25 mg before retiring. dose of 0.125 mg may be found to be sufficient for some patients (e.g., low body weight). A dose of 0.5 mg should be used only for exceptional patients who do not respond adequately to a trial of a lower dose since the risk of several adverse reactions increases with the size of the dose administered. A dose of 0.5 mg should not be exceeded. In geriatric and/or debilitated patients the recommended dosage range is 0.125 mg to 0.25 mg. Therapy should be initiated at 0.125 mg in this group and the 0.25 mg dose should be used only for exceptional patients who do not respond to a trial of the lower dose. A dose of 0.25 mg should not be exceeded in these patients. |
| HORMONES/ CONTRACEPTIVES | ESTROGENS include: ethinyl estradiol and mestranol. PROGESTERONES include: Norethynodrel, norethindrone, norethindrone acetate, norgestimate, desogestrel, ethyndiol diacetate, norgestrel, levonorgestrel, drospirenone. | See other columns. | Hormone-Containing Contraceptives General Dosing Information: Combination contraceptives are those containing both estrogen and progesterone. Several types of combination birth control pills exist, including monophasic pills, biphasic pills, triphasic pils, and 91-day cycle pills. USE: Starting at the beginning of the pill pack, take one each day a approximately the same time every day to increase efficacy. WHEN TO BEGIN: The following regimens may be used when first starting on birth control pills: Taking one pill each day, starting on the fifth day after the onset of menses and continuing for 21 or 28 days. Beginning pills on the first day of the menstrual period. Beginning on the first Sunday after the menstrual period starts. 21-DAY PILL CONTAINER: Take one pill daily for 21 days, stop for 7 days, then resume taking the pills with a new container of pills 28-DAY PILL CONTAINER: Start with the first pill in the container and swallow one daily for 28 days. Do not stop taking the pills. The last 7 ae usually placebos. 91-DAY PILL CONTAINER: One pill is taken daily for 12 weeks, followed by one week of inactive pills. A menstrual period occurs during the week of inactive pills, so women on this regimen have a period only once every three months. Monophasic Pills: Alesse, Brevicon, Demulen, Desogen, Levlen, Levlite, Loestrin, Microgestin, Modicon, Necon, Nelova, Nordette, Norinyl, Ortho-Cept, Ortho-Cyclen, Ortho-Novum, Ovcon, Ovral, Yasmin, Zovia. Monophasic pills have a constant dose of estrogen and progestin in each of the hormonally active pills through the entire cycle (21 day of ingesting active pills). Several of the brands listed above may be available in several strengths of estrogen or progesterone, from which doctors choose according to a woman's individual needs. Biphasic Pills: Jenest, Mircette, Necon 10/11, Nelova 10/11, and Ortho-Novum 10/11 Biphasic Pills typically contain two different progesterone doses. The progesterone dose is increased about halfway through the cycle. Triphasic Pills: Cyclessa, Estrostep, Ortho-Novum 7/7/7, Ortho Tri Cyclen, Ortho Tri-Cyclen LO, Tri-Levlen, Tri-Norinyl, Triphasil, Trivora |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | Triphasic pills gradually increase the dose of estrogen during the cycle (some pills also increase the progesterone dose). Three different increasing pill doses are contained in each cycle.<br>Ninety-One Day BCP: Levonorgestrel/ethynl estradiol (Seasonale)<br>These pills are monophasic birth control pills that have been approved for use on a daily basis for 84 days without interruption. Users have fewer schedules menstrual cycles (only 1 period every 3 months).<br>Topical Contraceptive Patch: Norelgestromin/ethinyl estradiol (Ortho Evra)<br>A new patch is applied on the same day of the week, each week for three weeks in a row. The first patch is applied on either the first day of the menstrual period or on the Sunday following menses. Or the fourth week, no patch is applied. Another 4-week cycle is started by applying a new patch following the 7-day patch free period.<br>Long-Acting, Injectable, Progesterone-Only Contraceptives: Medroxyprogesterone acetate (Depo-Provera)<br>The first injection is given within five days following the onset of menstruation. After that, an injection is needed every 11-13 weeks. Unlike pills, the injection works right away.<br>Progesterone-Only Pills: Norethindrone (Nor-QD)<br>Progesterone-only pills, also known as mini-pills, are not used widely in the US. POPs are ingested once daily, every day. They may be started on any day, and there are no pill-free days or different colored pills to track. Since progesterone is the only hormonal ingredient, estrogen-related side effects are avoided.<br>Vaginal Ring:<br>Etonogestrel/ethinyl estradiol (NuvaRing)<br>The ring is self-inserted into the vagina. Exact positioning is not required for it to be effective. The vaginal ring must be inserted within 5 days of the onset of the menstrual period, even if bleeding is still occurring. During the first cycle, an additional method of contraception is recommended. The ring remains in place continuously for three weeks. It is removed for one week. The nex ring is then inserted one week after the last ring was removed. |
| NON-BENZODIAZEPINE ANXIOLYTICS SEDATIVES HYPNOTICS TRANQUILIZERS | | CHLORAL HYDRATE | The usual hypnotic dose is 500 mg to 1 g, taken 15 to 30 minutes before bedtime or ½ hour before surgery. The usual sedative dose i 250 mg three times daily after meals. Generally, single doses or daily dosage should not exceed 2 g. |
| | | CHLORAL BETAINE | Chloral betaine 707 mg (chloral hydrate 414 mg)<br>Dose: 1-2 tablets with water or milk at bedtime, max. 5 tablets (2 g chloral hydrate) daily |
| | | CLOMETHIAZOLE (or CHLOMETHIAZOLE) | MRTD (Maximum Recommended Therapeutic Dose) in mg/kg-body weight (bw)/day based upon an average adult weighing 60 kg 6.40000 |
| | | DIPHENHYDRAMINE | Adults: 25 to 50 mg three or four times daily.<br>Children (over 20 lb): 12.5 to 25 mg three to four times daily.<br>Maximum daily dosage not to exceed 300 mg. |
| | | ETHCHLORVYNOL | Due to the problems it can cause, it is unusual for ethchlorvynol to be prescribed for periods exceeding seven days. |
| | | PROMETHIAZINE. | Administration of 12.5 to 25 mg Phenergan by the oral route or by rectal suppository at bedtime will provide sedation in children. Adults usually require 25 to 50 mg for nighttime, presurgical, or obstetrical sedation. |
| | | ZALPELON (imidazopyridine) | The recommended dose of Sonata for most nonelderly adults is 10 mg. For certain low weight individuals, 5 mg may be a sufficient dose. Although the risk of certain adverse events associated with the use of Sonata appears to be dose dependent, the 20 mg dose has been shown to be adequately tolerated and may be considered for the occasional patient who does not benefit from a trial of a lower dose. |
| | | ZOLPIDEM (pyrazolopyrimidine) | The recommended dose for adults is 10 mg immediately before bedtime, indicated for the short-term treatment of insomnia. |
| | | ZOPICLONE | The usual dose is 7.5 mg at bedtime. This dose should not be exceeded. Depending on clinical response and tolerance, the dose may be lowered to 3.75 mg.<br>Geriatrics:<br>In the elderly and/or debilitated patient an initial dose of 3.75 mg at bedtime is recommended. The dose may be increased to 7.5 mg if the starting dose does not offer adequate therapeutic effect. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| STIMULANTS | | CAFFEINE | Caffeine Oral is used to treat the following: Absence of Breathing in the Newborn Caffeine Oral may also be used to treat: Drowsiness, Low Energy Caffeine citrate is indicated for the short term treatment of apnea of prematurity in infants between 28 and <33 weeks gestational age. Caffeine Citrate: Loading Dose - 20 mg/kg Maintenance Dose - 5 mg/kg |
| | | NICOTINE | NICOTROL Inhaler is indicated as an aid to smoking cessation for the relief of nicotine withdrawal symptoms. NICOTROL Inhaler therapy is recommended for use as proof of a comprehensive behavioral smoking cessation program. It it supplied as 42 cartridges each containing 10 mg (4 mg is delivered) nicotine. Initial Treatment: Up to 12 Weeks: 6-16 cartridges/day Gradual Reduction (if needed) - 6-12 Weeks: No tapering strategy has been shown to be superior to any other in clinical studies. |
| OTC MEDICATIONS | | DEXTROMETHORPHAN | Now prescription only in the United States. MRTD (Maximum Recommended Therapeutic Dose) in mg/kg-body weight (bw)/day based upon an average adult weighing 60 kg 2.00000 |
| MISCELLANEOUS | | GHB Gamma-hydroxybutyrate | It has been used as a general anesthetic, and a hypnotic in the treatment of insomnia. GHB has also been used to treat clinical depression, and improve athletic performance. In the US, the FDA permits the use of GHB to reduce the number of cataplexy attacks in patients with narcolepsy. In Italy, GHB is used for the treatment of alcoholism (50 to 100 mg per kg per day, in 3 or more divided doses), both for acute alcohol withdrawal and medium to long term detoxification. LD50 of GHB is estimated to be between 1100 mg/kg and 2000 mg/kg in rodents and is almost certainly lower in humans. |
| | | MEPROBROMATE | Meprobromate is available in 200 mg and 400 mg tablets for oral administration. Symptoms of meprobromate overdose include coma, drowsiness, loss of muscle control, severly impaired breathing, shock, sluggishness, and unresponsiveness. Death has been reported with ingestion of as little as 12 g of meprobromate and survival with as much as 40 g. |
| | | METHQUALONE | In the United States, the marketing of methaqualone pharmaceutical products stopped in 1984, and methaqualone was transferred to Schedule I of the CSA. |
| | | NITROUS OXIDE | Nitrous Oxide is a weak general anesthetic, and is generally not used alone. It has a very low short-term toxicity and is an excellent analgesic. In general anesthesia it is often used in a 2:1 ratio with oxygen in addition to more powerful general anesthetic agents. Possession of nitrous oxide is illegal in most localities in the United States for the purposes of inhaling or ingesting if not under the care of a physician or dentist. |
| | | PCP Phencyclidine | Not available for medicinal use. |
| HERBAL MEDICINALS | | VALERIAN ROOT (*Valeriana officinalis*, Valerianaceae) | Dosing not regulated/approved by FDA. Large doses are known to cause withdrawal symptoms when stopped, as it is mildly addictive. Those with liver disease are advised not to use valerian. Valerian is the source of valeric acid. |
| | | SALVINORIN A Salvinorin A is the main active psychotropic constituent of the plant *Salvia divinorum* (diviner's sage, Mexican mint). | N.A. Salvinorin A is a dissociative hallucinogenic compound that is active at the extremely low doses of 0.2-0.5 mg, second only to LSD in quantitative potency, making it the most potent naturally occurring drug known to date. A dose of 200 to 500 micrograms produces profound hallucinations when smoked. Its' effects in the open field test in mice and loco motor activity tests in rats are similar to mescaline. |
| | | ST. JOHN'S WORT Refers to the species *Hypericum perforatum*. | The dosage of St John's wort preparations vary greatly between formulations, due to variability in the plant source and preparation processes. The doses of St. John's wort extract used in clinical trials generally range from 350 to 1800 mg daily (equivalent to 0.4 to 2.7 mg hypericin depending on the preparation). The recommended dosage for various forms of St John's wort as recommended by the British Herbal Medicine Association Scientific Committee (1983) are as follows: dried herb: |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| ANTI-DEPRESSION DRUGS | | CITALOPRAM HBR (CELEXA) | 2-4 g or by infusion three times daily<br>liquid extract 2-4 mL (1:1 in 25% alcohol) three times daily<br>tincture 2-4 mL (1:10 in 45% alcohol) three times daily<br>Celexa (citalopram HBr) is indicated for the treatment of depression.<br>Celexa (citalopram HBr) should be administered at an initial dose of 20 mg once daily, generally with an increase to a dose of 40 mg/day. Dose increases should usually occur in increments of 20 mg at intervals of no less than one week |
| | | ESCITALOPRAM OXALATE LEXAPRO ™ | LEXAPRO (escitalopram) is indicated for the treatment of major depressive disorder and Generalized Anxiety Disorder (GAD).<br>The recommended dose of LEXAPRO is 10 mg once daily. |
| | | FLUOXETINE HYDROCHLORIDE | Prozac is indicated for the treatment of: Major Depressive Disorder: a dose of 20 mg/day, administered in the morning, is recommended as the initial dose. The maximum fluoxetine dose should not exceed 80 mg/day. Obsessive Compulsive Disorder: a dose of 20 mg/day administered in the morning, is recommended as the initial dose. The maximum fluoxetine dose should not exceed 80 mg/day. Bulimia Nervosa: the recommended dose is 60 mg/day, administered in the morning. Panic Disorder: Treatment should be initiated with a dose of 10 mg/day. After 1 week, the dose should be increased to 20 mg/day. |
| | | PAROXETINE HYDROCHLORIDE | Major Depressive Disorder: The recommended initial dose is 20 mg/day. Some patients not responding to a 20-mg dose may benefit from dose increases, in 10-mg/day increments, up to a maximum of 50 mg/day. Obsessive Compulsive Disorder: The recommended dose of PAXIL in the treatment of OCD is 40 mg daily. Patients should be started on 20 mg/day and the dose can be increased in 10-mg/day increments. The maximum dosage should not exceed 60 mg/day. Panic Disorder: The target dose of PAXIL in the treatment of panic disorder is 40 mg/day. The maximum dosage should not exceed 60 mg/day. Social Anxiety Disorder: The recommended and initial dosage is 20 mg/day. Generalized Anxiety Disorder: The recommended starting dosage and the established effective dosage is 20 mg/day. Posttraumatic Stress Disorder: The recommended starting dosage and the established effective dosage is 20 mg/day. |
| | | FLUVOXAMINE MALEATE (LUVOX). | Fluvoxamine is indicated in the treatment of depression and for Obsessive Compulsive Disorder (OCD).<br>The recommended starting dose for LUVOX Tablets in adult patients is 50 mg, administered as a single daily dose at bed time. The maximum therapeutic dose should not to exceed 300 mg per day. |
| | | SERTRALINE HYDROCHLORIDE | Major Depressive Disorder and Obsessive-Compulsive Disorder: ZOLOFT treatment should be administered at a dose of 50 mg once daily. Panic Disorder, Posttraumatic Stress Disorder and Social Anxiety Disorder: ZOLOFT treatment should be initiated with a dose of 25 mg once daily. After one week, the dose should be increased to 50 mg once daily. Premenstrual Dysphoric Disorder: ZOLOFT treatment should be initiated with a dose of 50 mg/day, either daily throughout the menstrual cycle or limited to the luteal phase of the menstrual cycle, depending on physician assessment. |
| | | AMITRIPTYLINE | For the relief of symptoms of depression. Endogenous depression is more likely to be alleviated than are other depressive states.<br>Oral Dosage: 75 mg of amitriptyline HCl a day in divided doses. If necessary, this may be increased to a total of 150 mg per day.<br>Intramuscular Dosage: Initially, 20 to 30 mg (2 to 3 ml) four times a day. |
| | | DESIPRAMINE HYDROCHLORIDE | Desipramine hydrochloride is indicated for relief of symptoms in various depressive syndromes, especially endogenous depression. The usual adult dose is 100 to 200 mg per day. Dosages above 300 mg/day are not recommended. Not recommended for use in children. |
| | | NORTRIPTYLINE | Nortriptyline HCl is indicated for the relief of symptoms of depression. Endogenous depressions are more likely to be alleviated than are other depressive states. It is not recommended for children<br>Usual Adult Dose - 25 mg three or four times daily. Doses above 150 mg/day are not recommended. Elderly and Adolescent Patients - 30 to 50 mg/day, in divided doses, or the total daily dosage may be given once a day. |
| | | DULOXETINE HYDROCHLORIDE | Cymbalta is indicated for the treatment of major depressive disorder (MDD) and pain associated with diabetic peripheral neuropathy.<br>Major Depressive Disorder: Cymbalta should be administered at a total dose of 40 mg/day |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | VENLAFAXINE Effexor | Diabetic Peripheral Neuropathic Pain: Cymbalta should be administered at a total dose of 60 mg/day given once a day Effexor (venlafaxine hydrochloride) is indicated for the treatment of major depressive disorder. The recommended starting dose for Effexor is 75 mg/day, up to a maximum of 375 mg/day, generally in three divided doses |
| | | PHENELZINE SULFATE | The usual starting dose of Nardil is one tablet (15 mg) three times a day. Maintenance dose may be as low as one tablet, 15 mg, a day or every other day, and should be continued for as long as is required. |
| | | TRANYLCYPROMINE (Parnate) | For the treatment of Major Depressive Episode Without Melancholia. The usual effective dosage is 30 mg per day, usually given in divided doses; may be extended to a maximum of 60 mg per day. When tranylcypromine is withdrawn, monoamine oxidase activity is recovered in 3 to 5 days, although the drug is excreted in 24 hours. |
| | | MIRTAZEPINE | Indicated for the treatment of major depressive disorder. The recommended starting dose for REMERON ® (mirtazapine) Tablets is 15 mg/day, up to a maximum of 45 mg/day. |
| | | NEFAZODONE HYDROCHLORIDE SERZONE ® | SERZONE (nefazodone hydrochloride) is indicated for the treatment of depression. When deciding among the alternative treatments available for this condition, the prescriber should consider the risk of hepatic failure associated with SERZONE treatment. The recommended starting dose for SERZONE (nefazodone hydrochloride) is 200 mg/day |
| | | TRAZODONE HYDROCHLORIDE DESYREL | DESYREL is indicated for the treatment of depression. An initial dose of 150 mg/day in divided doses is suggested, up to but not in excess of 600 mg/day in divided doses. |
| | | BUPROPION HYDROCHLORIDE WELLBUTRIN (bupropion hydrochloride) | WELLBUTRIN is indicated for the treatment of depression. The usual adult dose is 300 mg/day, given 3 times daily. WELLBUTRIN should be discontinued in patients who do not demonstrate an adequate response after an appropriate period of treatment at 450 mg/day. When Wellbutrin is used in combination with an SSRI to offset sexual side effects, the usual dose is 75 mg per day. |
| | | Isocarboxazid | The maximum daily dose of isocarboxazid is 60 mg. |
| | | Moclobemide | Depression: The initial dose is 300 mg daily in 2 or 3 divided doses. Social Phobia: The recommended dose is 600 mg daily in 2 or 3 divided doses. A single 300 mg dose of moclobemide inhibits 80% of monoamine oxidase A (MAO-A) and 30% of monoamine oxidase B (MAO-B), blocking the decomposition of norepinephrine, serotonin and, to a lesser extent, dopamine. No reuptake inhibition on any of the neurotransmitters occurs. |
| | | Selegiline | 10 mg per day administered as divided doses of 5 mg each. |
| NEUROSTEROID INHIBITORS | 5-ALPHA-REDUCTASE INHIBITORS | FINASTERIDE | The recommended dosage is 1 mg orally once per day. It may be administered with or without meals. An alternate dosage of 5 mg orally once per day is also included. It may be administered with or without meals. In general, daily use for three months or more is necessary before benefit is observed. Continued use is recommended to sustain benefit, which should be re-evaluated periodically. Withdrawal of treatment leads to reversal of effect within 12 months. In clinical studies, single doses of finasteride up to 400 mg and multiple doses of finasteride up to 80 mg/day for three months did not result in adverse reactions. |
| | | DUTASTERIDE | The recommended therapeutic dose of dutasteride is 0.5 mg taken orally once per day. Dutasteride pharmacokinetics has not been investigated in subjects less than 18 years of age. No dose adjustment is necessary in the elderly. In volunteer studies, single doses of dutasteride up to 40 mg (80 times the therapeutic dose) for 7 days have been administered without significant safety concerns. In a clinical study, daily doses of 5 mg (10 times the therapeutic dose) were administered to 60 subjects for 6 months with no additional adverse effects to those seen at therapeutic does of 0.5 mg. |
| | | SAW PALMETTO | Tablets/Capsules. A dose of 160 mg twice daily or 320 milligrams daily (containing 80% to 90% liposterolic content) for up to 11 months has been taken by mouth. Higher doses may be used under medical supervision. Berries. A dose of one to two grams of ground, dried, or whole berries daily has been taken by mouth. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | Tincture. A dose of two to four milliliters (1:4) three times daily has been taken by mouth. |
| | | | Fluid Extract of Berry Pulp. A dose of one to two milliliters (1:1) three times daily has been taken by mouth. |
| | | | Rectal Suppositories. A dose of 640 milligrams once daily has been used. Rectal use of saw palmetto is no better than taking saw palmetto by mouth. |
| | | | Tea. Tea made from berries may not be effective because the proposed active ingredient does not dissolve in water. |
| | | SPIRONOLACTONE | Treatment protocols may involve continuous spironolactone use at 50 mg to 200 mg per day or cyclic use; for example, 50 mg or 100 mg twice daily from the $4^{th}$ to the $22^{nd}$ day of the menstrual cycle. Numerous treatment protocols involving spironolactone have been used in different studies, but no particular treatment approach has been shown to be significantly superior. |
| | 3-ALPHA REDUCTASE INHIBITORS | INDOMETHACIN | Indomethacin can be administered in the form of capsules (25 mg and 50 mg); sustained-release capsules (75 mg); a suspension (25 mg/ml); or a suppository (50 mg). The recommended dose for adults is 50-200 mg per day split into 2-3 doses. |
| CLASS OF COMPOUNDS THAT SELECTIVELY MODULATES $GABA_A$ RECEPTORS | | FLUMAZENIL (Romazicon) | ROMAZICON is indicated for the complete or partial reversal of the sedative effects of benzodiazepines in cases where general anesthesia has been induced and/or maintained with benzodiazepines, where sedation has been produced with benzodiazepines for diagnostic and therapeutic procedures, and for the management of benzodiazepine overdose. Reversal of Conscious Sedation: The recommended initial dose of ROMAZICON is 0.2 mg (2 mL) administered intravenously over 15 seconds. If the desired level of consciousness is not obtained after waiting an additional 45 seconds, a second dose of 0.2 mg (2 mL) can be injected and repeated at 60-second intervals where necessary (up to a maximum of 4 additional times) to a maximum total dose of 1 mg (10 mL). Reversal of General Anesthesia in Adult Patients: The recommended initial dose of ROMAZICON is 0.2 mg (2 mL) administered intravenously over 15 seconds. If the desired level of consciousness is not obtained after waiting an additional 45 seconds, a further dose of 0.2 mg (2 mL) can be injected and repeated at 60-second intervals where necessary (up to a maximum of 4 additional times) to a maximum total dose of 1 mg (10 mL). Management of Suspected Benzodiazepine Overdose in Adult Patients: the recommended initial dose of ROMAZICON is 0.2 mg (2 mL) administered intravenously over 30 seconds. If the desired level of consciousness is not obtained after waiting 30 seconds, a further dose of 0.3 mg (3 mL) can be administered over another 30 seconds. Further doses of 0.5 mg (5 mL) can be administered over 30 seconds at 1-minute intervals up to a cumulative dose of 3 mg. |
| | | MILTIRONE | The below doses are based on scientific research, publications, traditional use, or expert opinion. Many herbs and supplements have not been thoroughly tested, and safety and effectiveness may not be proven. You should read product labels, and discuss doses with a qualified healthcare provider before starting therapy. Standardization: There is no widely accepted standardization or well-studied dosing of miltirone, and many different doses are used traditionally. Adults (18 years and older): By mouth. Oral dosing has not been studied in well-conducted trials in humans, and therefore no specific dose can be recommended. By injection: In research from the 1970s, an 8 milliliter injection of miltirone (16 grams of the herb) was given intravenously (diluted in 500 milliliters of a 10% glucose solution) for up to four weeks for ischemic stroke. Safety and effectiveness have not been established for this route of administration and it cannot not recommended at his time. Children (younger than 18 years): There is not enough scientific evidence to recommend the safe use of danshen in children, and it should be avoided due to potentially serious side effects. |
| | FLAVONOIDS | They have been classified according to their chemical structure, and are usually subdivided into 6 subgroups: Flavonols, including Quercetin, Kaempferol, Myricetin, Isorhamnetin Flavones, including Luteolin, Apigenin | N.A. |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | Flavanones, including Hesperetin, Naringenin, Eriodictyol Flavan-3-ols, including (+)-Catechin, (+)-Gallocatechin, (−)-Epicatechin, (−)-*Epigallocatechin, (−)-Epicatechin 3-gallate, (−)-Epigallocatechin 3-gallate, Theaflavin, Theaflavin 3-gallate, Theaflavin 3'-gallate, Theaflavin 3,3' digallate, Thearubigins Isoflavones, including Genistein, Daidzein, Glycitein Anthocyanidins, including Cyanidin, Delphinidin, Malvidin, Pelargonidin, Peonidin, Petunidin | |
| DOPAMINE AGONISTS | ERGOT ALKALOIDS | | The dose of bromocriptine will be different for different patients. Follow your doctor's orders or the directions on the label. The following information includes only the average doses of bromocriptine. If your dose is different, do not change it unless your doctor tells you to do so. The number of capsules or tablets that you take depends on the strength of the medicine. Also, the number of doses you take each day, the time allowed between doses, and the length of time you take the medicine depend on the medical problem for which you are taking bromocriptine.<br>For oral dosage forms (capsules and tablets): For infertility, male hormone problem (male hypogonadism), starting the menstrual cycle (amenorrhea), or stopping abnormal milk secretion from nipples (galactorrhea): Adults and teenagers 15 years of age or older - At first, 1.25 to 2.5 milligrams (mg) once a day taken at bedtime with a snack. Then your doctor may change your dose by 2.5 mg every three to seven days as needed. Doses greater than 5 mg a day are taken in divided doses with meals or at bedtime with a snack. Teenagers less than 15 years of age and children - Use and dose must be determined by your doctor.<br>For lowering growth hormone (acromegaly): Adults and teenagers 15 years of age or older - At first, 1.25 to 2.5 milligrams (mg) once a day taken at bedtime with a snack for three days. Then your doctor may change your dose by 1.25 or 2.5 mg every three to seven days as needed. Doses greater than 5 mg are divided into smaller doses and taken with meals or at bedtime with a snack. Teenagers less than 15 years of age and children - Use and dose must be determined by your doctor.<br>For Parkinson's disease: Adults and teenagers 15 years of age or older - At first, 1.25 milligrams (mg) one or two times a day taken with meals or at bedtime with a snack. Then your doctor may change your dose over several weeks as needed. Teenagers less than 15 years of age and children - Use and dose must be determined by your doctor.<br>For pituitary tumors: Adults and teenagers 15 years of age or older - At first, 1.25 milligrams (mg) two or three times a day taken with meals. Then your doctor may change your dose over several weeks as needed. Teenagers less than 15 years of age and children - Use and dose must be determined by your doctor. |
| PRESCRIPTION STIMULANTS | | METHYLPHENIDATE | Methylphendiate comes in 5 mg, 10 mg and 20 mg tablets.<br>ADULTS<br>Tablets: Administer in divided doses, 2 or 3 times daily, preferably 30 to 45 minutes before meals.<br>Average dosage is 20 to 30 mg daily. Some patient may require 40 to 60 mg daily. In others, 10 to 15 mg daily will be adequate.<br>FOR CHILDREN, DOSAGES SHOULD BE INITIATED IN INCREMENTS<br>Days 1-3: One 5 mg tablet per day<br>Days 4-6: Two 5 mg tablets per day<br>Add one pill every fourth day until a dosage of 20 mg per day is achieved.<br>Daily dosage above 60 mg is not recommended. |
| | | ADDERALL. | Attention Deficit Disorder with Hyperactivity: Not recommended for children under 3 years of age. In children from 3 to 5 years of age, start with 2.5 mg daily; daily dosage may be raised in increments of 2.5 mg at weekly intervals until optimal response is |

TABLE 1-continued

EXEMPLARY LISTING OF PHARMACOLOGICAL COMPOUNDS AND SUGGESTED DOSAGES FOR USE WITH THE PRESENT INVENTION

| DRUG CLASS | SECONDARY DRUG CLASS | EXEMPLARY DRUG LISTING | DOSAGE |
|---|---|---|---|
| | | | obtained. In children 6 years of age and older, start with 5 mg once or twice daily; daily dosage may be raised in increments of 5 mg at weekly intervals until optimal response is obtained. Only in rare cases will it be necessary to exceed a total of 40 mg per day. Give first dose on awakening; additional doses (1 or 2) at intervals of 4 to 6 hours. Where possible, drug administration should be interrupted occasionally to determine if there is a recurrence of behavioral symptoms sufficient to require continued therapy.<br>Narcolepsy: Usual dose 5 mg to 60 mg per day in divided doses, depending on the individual patient response. Narcolepsy seldom occurs in children under 12 years of age; however, when it does, dextroamphetamine sulfate may be used. The suggested initial dose for patients aged 6-12 is 5 mg daily; daily dose may be raised in increments of 5 mg at weekly intervals until optimal response is obtained. In patients 12 years of age and older, start with 10 mg daily; daily dosage may be raised in increments of 10 mg at weekly intervals until optimal response is obtained. If bothersome adverse reactions appear (e.g., insomnia or anorexia), dosage should be reduced. Give first dose on awakening; additional doses (1 or 2) at intervals of 4 to 6 hours. |
| | | DEXEDRINE | Narcolepsy. Usual dose 5 to 60 mg per day in divided doses, depending on the individual patient response. Narcolepsy seldom occurs in children under 12 years of age; however, when it does Dexedrine (dextroamphetamine sulfate) may be used. The suggested initial dose for patients aged 6 to 12 is 5 mg daily; daily dose may be raised in increments of 5 mg at weekly intervals until optimal response is obtained. In patients 12 years of age and older, start with 10 mg daily; daily dosage may be raised in increments of 10 mg at weekly intervals until optimal response is obtained. If bothersome adverse reactions appear (e.g. insomnia or anorexia), dosage should be reduced. Spansule capsules may be used for once-a-day dosage wherever appropriate. With tablets give first dose on awakening, additional doses (1 or 2) at intervals of 4 to 6 hours.<br>Attention Deficit Disorder with Hyperactivity. Not recommended for pediatric patients under 3 years of age. In pediatric patients from 3 to 5 years of age, start with 2.5 mg daily, by tablet daily dosage may be raised in increments of 2.5 mg at weekly intervals until optimal response is obtained. In pediatric patients 6 years of age and older, start with 5 mg once or twice daily, daily dosage may be raised in increments of 5 mg at weekly intervals until optimal response is obtained. Only in rare cases will it be necessary to exceed a total of 40 mg per day. Spansule capsules may be used for once-a-day dosage wherever appropriate. With tablets, give first dose on awakening additional doses (1 or 2) at intervals of 4 to 6 hours. |

We claim:

1. A method of treating an obsessive compulsive disorder in a patient comprising administering to the patient a composition comprising flumazenil in a pharmaceutically acceptable carrier, wherein the flumazenil is administered in a therapeutically effective quantity.

2. The method of claim 1, wherein the therapeutically effective quantity of flumazenil is between 0.5 mg/day and 10 mg/day.

3. The method of claim 1, wherein the flumazenil is administered at a rate of between 0.1 and 0.3 mg over predetermined time intervals for a total administration of between 0.5 mg/day and 10 mg/day.

4. The method of claim 3, wherein the predetermined time interval is in the range of 1 and 15 minutes.

5. The method of claim 1, wherein the flumazenil is administered at a rate of between 0.1 and 0.3 mg over predetermined time intervals for a total administration of between 1.0 mg/day and 3.0 mg/day.

* * * * *